US006281354B1

(12) United States Patent
Boger

(10) Patent No.: US 6,281,354 B1
(45) Date of Patent: Aug. 28, 2001

(54) ANALOGS OF DUOCARMYCIN AND CC-1065

(75) Inventor: Dale L. Boger, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/423,576

(22) Filed: Nov. 9, 1999

Related U.S. Application Data

(60) Provisional application No. 60/048,505, filed on May 22, 1997.

(51) Int. Cl.[7] .................. C07D 223/32; C07D 487/04

(52) U.S. Cl. ..................... 540/576; 548/421; 548/429

(58) Field of Search .............................. 540/576, 586; 546/67; 548/421, 429

(56) References Cited

PUBLICATIONS

Boger et al., J. Am. Chem. Soc. (1994), vol. 116, No. 25, pp. 11335–11348, 1994.*
Chidester, et al., "The Structure of CC–1065, a Potent Antitumor Agent, and Its binding to DNA", *J. Am. Chem. Soc. 103*: 7629–7635 (1981).
Takahashi, et al., "Duocarmycin A, A New Antitumor Antibiotic from Streptomyces", *J. Antibiot. 41*: 1915–1917 (1988).
Boger, et al., "Synthesis and Evaluation of Aborted and Extended CC–1065 Functional Analogues: (+)–and (–)–CPI–PDE–$I_1$, (+)—and (–)–CPI–$CDPI_1$, and (±)–, (+)–, and (–)–CPI–$CDPI_3$. Preparation of Key Partial Structures and Definition of an Additional Functional Role of the CC–1065 Central and Right–Hand Subunits", *J. Am. Chem. Soc. 112*: 4623–4632 (1990).
Ichimura, et al., "Duocarmycin SA, A New Antitumor Antibiotic from Streptomyces Sp.", *J. Antibiotics 43*: 1037–1038 (1990).
Boger, et al., "An Alternative and Convenient Strategy for Generation of Substantial Quantities of Singly 5'–$^{32}$P–End–Labeled Double–Stranded DNA for Binding Studies: Development of a Protocol for Examination of Functional features of (+)–CC–1065 and the Duocarmycins that Contribute to their Sequence–Selective DNA Alkylation Properties", *Tetrahedron 47*: 2661–2682 (1991).
Boger, "Duocarmycins: A New Class of Sequences Selective DNA Minor Groove Alkylating Agents", *Chemtracts–Organic Chemistry 4*: 329–349 (1991).
Boger, et al., "Design, Synthesis, and Evaluation of Functional Analogs of CC–1065 and the Duocarmycins", *Proc. Robert A. Welch Found. Conf. Chem. Res. (Chem. Front. Med.) 35*: 137–179 (1991).
Boger, et al., "Total Synthesis and Preliminary Evaluation of (+)—and ent–(–)–Duocarmycin SA", *J. Am. Chem. Soc. 115*: 9025–9036 (1993).

Boger, et al., "Molecular Basis for Sequence Selective DNA Alkylation by (+)—and ent–(–)–CC–1065 and Related Agents: Alkylation Site Models that Accomodate the Offset AT–Rich Adenine N3 Alkylation Selectivity", *Bioorg. Med. chem. 2*: 115–135 (1994).
Boger, et al., "(+)—and ent–(–)–Duocarmycin SA and (+)–and ent–(–)–N–BOC–DSA DNA Alkylation Properties. Alkylation Site Models That Accomodate the Offset AT–Rich Adenine N3 Alkylation Selectivity of the Enantiomeric Agents", *J. Am. Chem. Soc. 116*: 1635–1656 (1994).
Boger, et al., "Role of the CC–1065 and Duocarmycin $N^2$ Substituent: Validation of a Direct Relationship between Solvolysis Chemical Stability and in Vitro Biological Potency", *J. Am. Chem. Soc. 116*: 5523–5524 (1994).
Boger, et al., "Chemical and Structural Comparison of N–BOC–CBQ and N–BOC–CBI: Identification and Structural Origin of an Unappreciated but Productive Stability of the CC–1065 and Duocarmycin SA Alkylation Subunits", *J. Am. Chem. Soc. 116*: 6461–6462 (19940.
Warpehoski, et al., "Acid–Dependent Electrophilicity of Cyclopropylpyrroloindoles. Nature's Masking Strategy for a Potent DNA Alkylator", *J. Am. Chem. Soc. 116*: 7573–7580 (1994).
Boger, et al., "Design Synthesis, and Evaluation of CC–1065 and Duocarmycin Analogs Incorporating the 2,3,10, 10a–Tetrahydro–1 H–cyclopropa–[d]benzo[f]quinol–5–one (CBQ) Alkylation Subunit: Identification and Structural Origin of Subtle Stereoelectronic Features that Govern Reactivity and Regioselectivity", *J. Am. Chem. Soc. 116*: 11335–11348 (1994).
Boger, "The Duocarmycins: Synthetics and Mechanistic Studies", *Acc. Chem. Res. 28*: 20–29 (1995).
Warpehoski, et al., "Enzyme–like Rate Acceleration in the DNA Minor Groove. Cyclopropylpyrroloindoles as Mechanism–Based Inactivators of DNA", *J. Am. Chem. Soc. 117*: 2951–2952 (1995).
Boger, et al., "CC–1065 and the duocarmycins: Unraveling the keys to a new class of naturally derived DNA alkylating agents", *Proc. Natl. Acad. Sci. USA 92*: 3642–3649 (1995).
Yasuzawa, et al., "Duocarmycins, Potent Antitumor Antibiotics Produced by Streptomyces sp. Structures and Chemistry", *Chem. Pharm. Bull. 43*: 378–391 (1995).
Boger, et al., "DNA Alkylation Properties of CC–1065 and Duocarmycin Analogs Incorporating the 2,3,10,10a–Tetrahydrocyclopropa[d]benzo[f]–quinol–5–one Alkylation Subunit: Identification of Subtle Structural Features that Contribute to the Regioselectivity of the Adenine N3 Alkylation Reaction", *J. Am. Chem. Soc. 117*: 11647–11655 (19950.
Boger, et al., "Examination of the role of the Duocarmycin SA Methoxy Substituents: Identification of the Minimum, Fully Potent DNA Binding Subunit", *Bioorg. Med. Chem. Lett. 6*: 2207–2210 (1996).

(List continued on next page.)

Primary Examiner—Taofiq A Solola
(74) Attorney, Agent, or Firm—Thomas E. Northrup

(57) ABSTRACT

The field of this invention is antitumor antibiotics. More particularly, the present invention relates to analogs of duocarmycin and CC-1065, which analogs have antitumor antibiotics activity.

5 Claims, 19 Drawing Sheets

OTHER PUBLICATIONS

Boger, et al., "CC–1065 and the Duocarmycins: Understanding their Biological Function through Mechanistic Studies", *Angew. Chem. Int. Ed. Engl. 35*: 1438–1474 (1996).

Boger, et al., "Total Synthesis of (+)–Duocarmycin A, epi–(+)–Duocarmycin A and Their Unnatural Enantiomers: Assessment of Chemical and Biological Properties", *J. Am. Chem. Soc. 119*: 311–325 (1997).

* cited by examiner

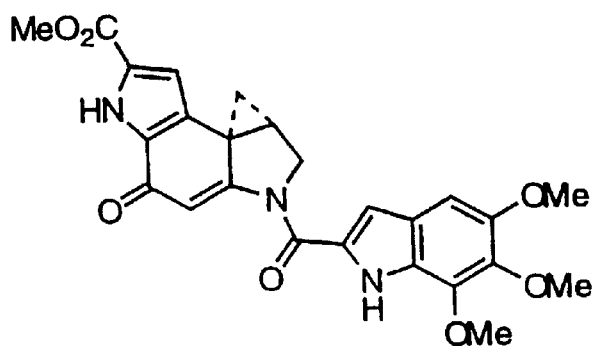
1, (+)-duocarmycin SA
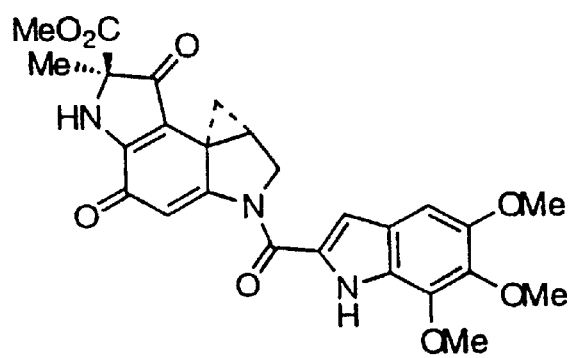
2, (+)-duocarmycin A
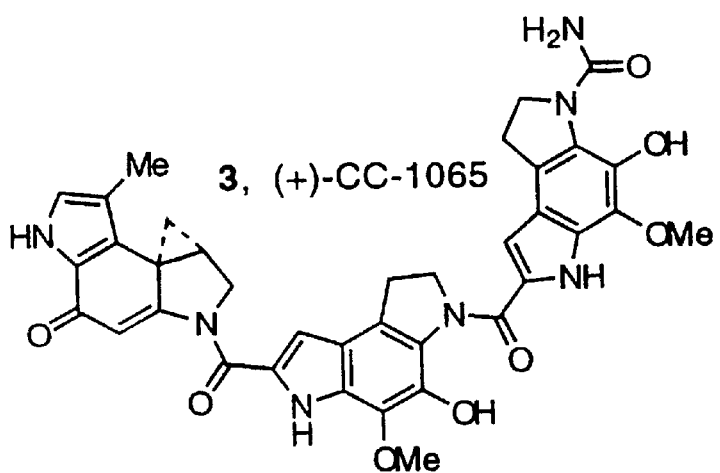
3, (+)-CC-1065
FIG. 1

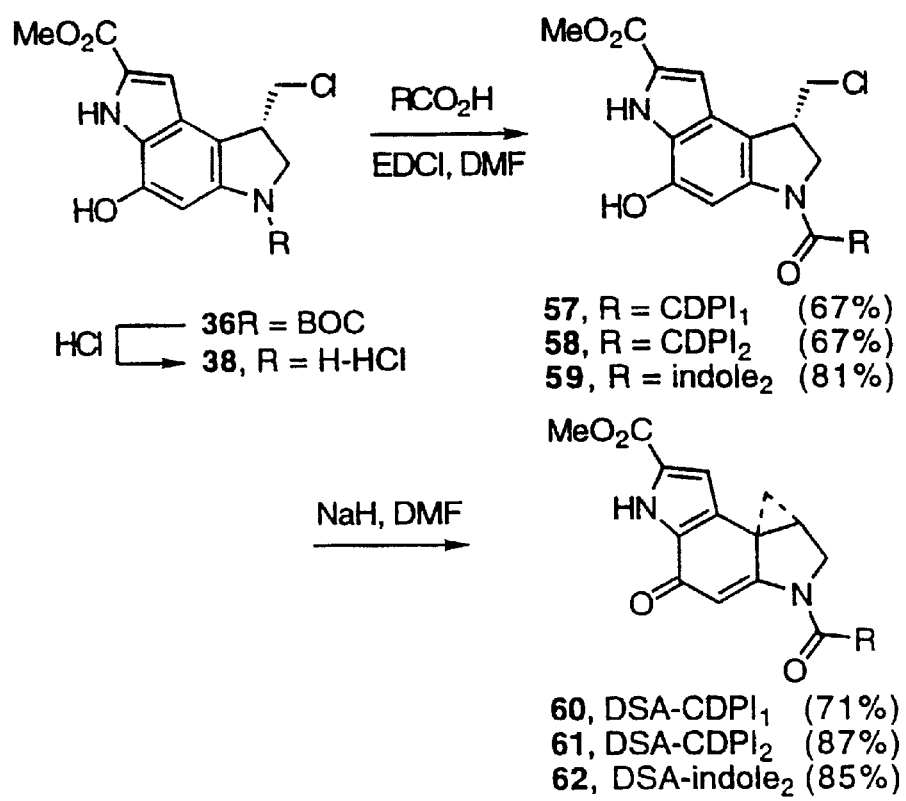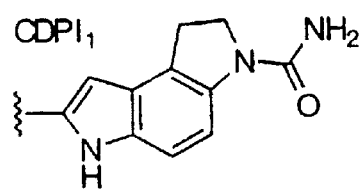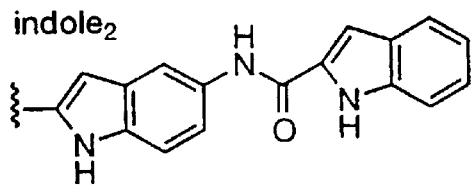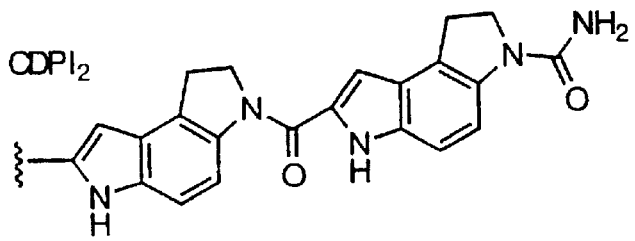
FIG. 8

Consensus DNA Alkylation Sequences

| Agent | base[a] | 5′ 4 | 3 | 2 | 1 | 0 | -1 | -2 | -3 | -4 3′ |
|---|---|---|---|---|---|---|---|---|---|---|
| Typical Agents: Natural Enantiomers | | | | | | | | | | |
| (+)-CC-1065 (3) | A/T (56)[b] Consensus | 67 A/T>G/C | 78 A/T>G/C | 94 A/T | 98 A/T | 100 A | 55 Pu≥Py | -- | -- | -- |
| (+)-DSA-CDPI$_2$ | A/T (56) Consensus | 71 A/T > G/C | 85 A/T>G/C | 100 A/T | 100 A/T | 100 A | 63 Pu>Py | -- | -- | -- |
| (+)-DSA-CDPI$_1$ | A/T (56) Consensus | -- | 65 A/T≥G/C | 100 A/T | 100 A/T | 100 A | 58 Pu≥Py | -- | -- | -- |
| (+)-duocarmyc in SA (1) | A/T (56) Consensus | -- | 79 A/T>G/C | 100 A/T | 100 A/T | 100 A | 69 Pu>Py | -- | -- | -- |
| (+)-N-BOC-DSA (4) | A/T (56) Consensus | -- | -- | -- | 95 A/T | 100 A | 65 Pu>Py | -- | -- | -- |
| Typical Agents: Unnatural Enantiomers | | | | | | | | | | |
| (−)-N-BOC-DSA (4) | A/T (56) Consensus | -- | -- | -- | 95 A/T | 100 A | 65 Pu>Py | -- | -- | -- |
| (−)-duocarmyc in SA (1) | A/T (56) Consensus | -- | -- | -- | 93 A/T | 100 A | 96 A/T | 73 A/T>G/C | 56 N | -- |
| (−)-DSA-CDPI$_2$ | A/T (56) Consensus | -- | -- | -- | 100 A/T | 100 A | 100 A/T | 90 A/T>G/C | 73 A/T>G/C | 58 N |
| (−)-CC-1065 (3) | A/T (56) Consensus | -- | -- | -- | 88 A/T | 100 A | 93 A/T | 82 A/T>G/C | 73 A/T>G/C | 56 N |

FIG. 11a

Reversed Analogs: Natural Enantiomers

| | | | | | | | | |
|---|---|---|---|---|---|---|---|---|
| (+)-CDPI$_2$-DSA (20) | A/T (56) Consensus | -- | -- | 95 A/T | 100 A | 98 A/T | 85 A/T>G/C | 70 A/T>G/C | 55 N |
| (+)-CDPI$_1$-DSA (19) | A/T (56) Consensus | -- | -- | 92 A/T | 100 A | 94 A/T | 73 A/T>G/C | 60 N | |

Reversed Analogs: Unnatural Enantiomers

| | | | | | | | | |
|---|---|---|---|---|---|---|---|---|
| (−)-CDPI$_1$-DSA (19) | A/T (56) Consensus | -- | 70 A/T>G/C | 98 A/T | 98 A/T | 100 A | 53 Pu>Py | -- | -- |
| (−)-CDPI$_2$-DSA (20) | A/T (56) Consensus | 69 A/T>G/C | 81 A/T>G/C | 98 A/T | 98 A/T | 100 A | 59 Pu>Py | -- | -- |

Sandwiched Analogs: Natural Enantiomers

| | | | | | | | | |
|---|---|---|---|---|---|---|---|---|
| (+)-CDPI-DSA-CDPI (30) | A/T (56) Consensus | -- | 68 | 87 A/T>G/C | 95 A/T | 100 A | 95 A/T | 74 A/T>G/C | 68 |

Sandwiched Analogs: Unnatural Enantiomers

| | | | | | | | | |
|---|---|---|---|---|---|---|---|---|
| (−)-CDPI-DSA-CDPI (30) | A/T (56) Consensus | -- | 64 | 86 A/T>G/C | 94 A/T | 100 A | 94 A/T | 78 A/T>G/C | 68 | a Percentage of the indicated base located at the designated position relative to the adenine-N3 alkylation site.

b Percentage composition within the DNA examined.

FIG. 11b

Detailed summary of the Consensus Alkylation Sequence of (+)- and *ent*-(−)-CDPI-DSA-CDPI.

| base[a] | +2 | +1 | A | −1 | −2 | 3' |
|---|---|---|---|---|---|---|
| (+)-CDPI-DSA-CDPI (natural enantiomer) | | | | | | |
| A (30)[b] | 66 | 84 | 100 | 74 | 53 | |
| T (26)[b] | 21 | 11 | 0 | 21 | 21 | |
| G (21)[b] | 11 | 3 | 0 | 5 | 21 | |
| C (23)[b] | 3 | 3 | 0 | 0 | 5 | |
| A/T (56)[b] | 87 | 95 | 100 | 95 | 74 | |
| composite | A/T > G/C | A/T | A | A/T | A/T > G/C | |
| *ent*-(−)-CDPI-DSA-CDPI (unnatural enantiomer) | | | | | | |
| A (30)[b] | 64 | 83 | 100 | 78 | 56 | |
| T (26)[b] | 23 | 11 | 0 | 17 | 23 | |
| G (21)[b] | 11 | 3 | 0 | 6 | 19 | |
| C (23)[b] | 3 | 3 | 0 | 0 | 3 | |
| A/T (56)[b] | 86 | 94 | 100 | 94 | 78 | |
| composite | A/T > G/C | A/T | A | A/T | A/T > G/C | |

[a] Percentage of the indicated base at the designated position at the adenine N3 alkylation sites.
[b] Percentage composition in the DNA examined.

FIG. 12

Sequence Preferences

| (+)- and ent-(−) N-BOC-DSA | (+)-DSA-CDPI$_2$ and ent-(−)-CDPI$_2$-DSA | ent-(−)-DSA-CDPI$_2$ and (+)-CDPI$_2$-DSA | (+)-CDPI-DSA-CDPI and ent-(−)-CDPI-DSA-CDPI |
|---|---|---|---|
| 5'-AA (75%)$^a$ | 5'-AAA (62%, 74%) | 5'-AAA (72%, 67%) | 5'-AAA (59%, 59%) |
| 5'-TA (40%) | 5'-TTA (53%, 21%) | 5'-AAT (40%, 28%) | 5'-AAT (43%, 38%) |
|  | 5'-TAA (22%, 39%) | 5'-TAA (39%, 33%) | 5'-TAA (28%, 28%) |
|  | 5'-ATA (22%, 06%) | 5'-TAT (13%, 13%) | 5'-TAT (00%, 00%) |

$^a$% Frequency of alkylation, e.g. 75% of all available 5'-AA sites were alkylated by (+)- and ent-(−)-N-BOC-DSA.

FIG. 13

*In vitro* cytotoxic activity of indole$_2$ derivatives.

| Agent | Configuration | IC$_{50}$(pM, L1210) |
|---|---|---|
| (+)-DSA-indole$_2$ | natural | 3 |
| (+)-CCBI-indole$_2$ | natural | 7 |
| (+)-CBI-indole$_2$ | natural | 10 |
| (+)-MCBI-indole$_2$ | natural | 10 |
| (+)-CPI-indole$_2$ | natural | 40 |
| (±)-CBQ-indole$_2$ | racemic | 4000 |
| (−)-DSA-indole$_2$ | unnatural | 150 |
| (−)-CCBI-indole$_2$ | unnatural | 400 |
| (−)-CBI-indole$_2$ | unnatural | 3900 |
| (−)-MCBI-indole$_2$ | unnatural | 30 |

FIG. 14

| Agent | IC$_{50}$(pM, L1210) | Rel. DNA Alkyl. Efficiency[a] | Agent | IC$_{50}$(pM, L1210) | Rel. DNA Alkyl. Efficiency[a] |
|---|---|---|---|---|---|
| natural enantiomers | | | unnatural enantiomers | | |
| (+)-1 | 10 | 1.0 | (−)-1 | 100 | 0.1 (1.0)[a] |
| (+)-54 | 10–12 | 1.0 | (−)-54 | 200 | 0.07 (0.7) |
| (+)-55 | 25 | 0.2 | (−)-55 | 1300 | 0.04 (0.4) |
| (+)-56 | 60 | 0.1 | (−)-56 | 1800 | 0.05 (0.5) |
| (+)-57 | 65 | 0.05 | (−)-57 | 1700 | 0.03 (0.3) |

[a]Within w794 DNA, 25 °C. The values in parenthesis are relative to *ent*-(−)-duocarmycin SA.

FIG. 15

Consensus Sequences for DNA Alkylation by Key Substructures and Analogs of Duocarmycin SA.[a]

| Agent | base[b] | 5' 4 | 3 | 2 | 1 | 0 | -1 | -2 | -3 | -4 3' |
|---|---|---|---|---|---|---|---|---|---|---|
| Natural Enantiomers | | | | | | | | | | |
| (+)-CC-1065 | A/T (56) Consensus | 67 A/T≥G/C | 78 A/T>G/C | 94 A/T | 98 A/T | 100 A | 55 Pu≥Py | -- | -- | -- |
| (+)-DSA-CDPI₂ | A/T (56) Consensus | 71 A/T> G/C | 85 A/T>G/C | 100 A/T | 100 A/T | 100 A | 63 Pu≥Py | -- | -- | -- |
| (+)-duocarmycin SA | A/T (56) Consensus | -- | 79 A/T>G/C | 100 A/T | 100 A/T | 100 A | 69 Pu>Py | -- | -- | -- |
| (+)-N-BOC-DSA | A/T (56) Consensus | -- | -- | -- | 95 A/T | 100 A | 65 Pu≥Py | -- | -- | -- |
| Unnatural Enantiomers | | | | | | | | | | |
| (-)-N-BOC-DSA | A/T (56) Consensus | -- | -- | -- | 95 A/T | 100 A | 65 Pu>Py | -- | -- | -- |
| (-)-duocarmycin SA | A/T (56) Consensus | -- | -- | -- | 93 A/T | 100 A | 96 A/T | 73 A/T>G/C | 56 N | -- |
| (-)-DSA-CDPI₂ | A/T (56) Consensus | -- | -- | -- | 100 A/T | 100 A | 100 A/T | 90 A/T>G/C | 73 A/T>G/C | 58 N |
| (-)-CC-1065 | A/T (56) Consensus | -- | -- | -- | 88 A/T | 100 A | 93 A/T | 82 A/T>G/C | 73 A/T>G/C | 56 N |

[a] Percentage of the indicated base located at the designated position relative to the adenine-N3 alkylation site. [b] Percentage composition within the DNA examined

FIG. 16

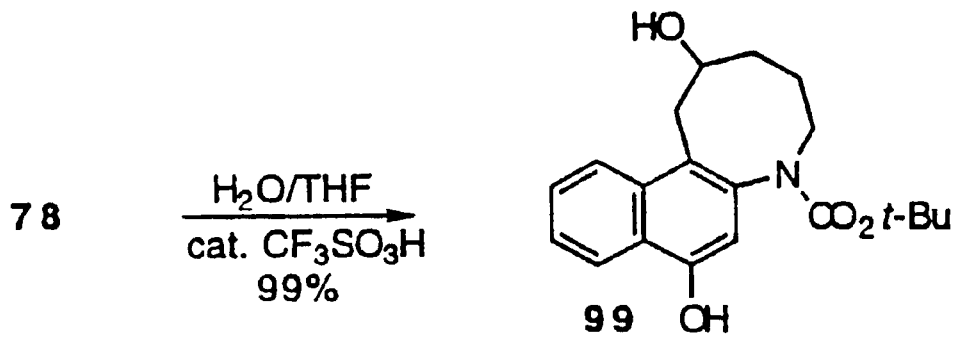
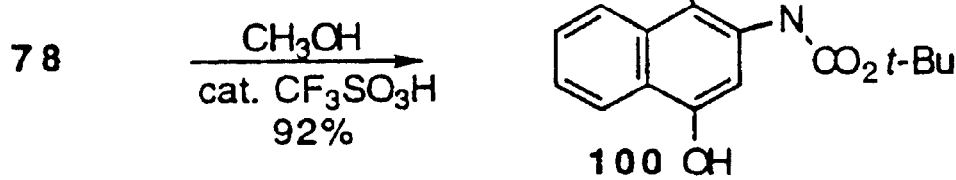
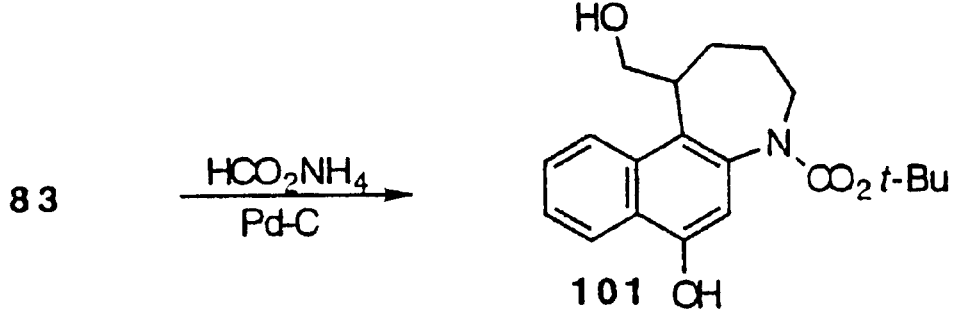
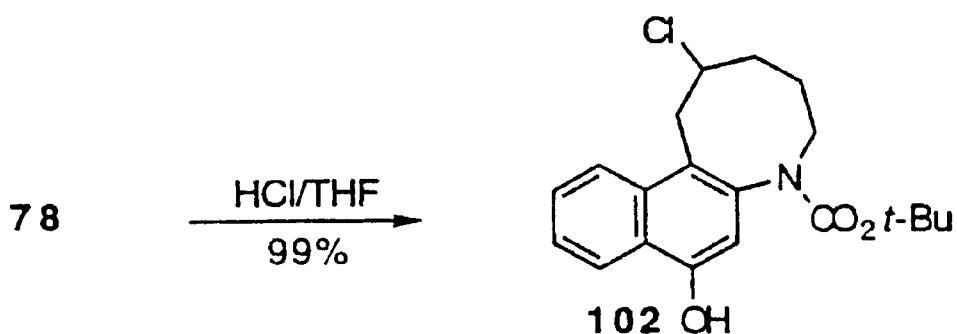
FIG. 17

*In vitro* cytotoxic activitiy of BOC derivatives.

| Agent | Configuration | IC$_{50}$ (µM, L1210) |
|---|---|---|
| (+)-N-BOC-DSA | natural | 0.006 |
| (+)-N-BOC-CCBI | natural | 0.02 |
| (+)-N-BOC-CBI | natural | 0.08 |
| (+)-N-BOC-MCBI | natural | 0.09 |
| (+)-N-BOC-CPI | natural | 0.3 |
| (+)-N-BOC-DA | natural | 2 |
| epi-(+)-N-BOC-DA | natural | 9 |
| (−)-N-BOC-CBQ | natural | 2 |
| (±)-N-BOC-F$_2$CBI | racemic | 110 |
| (+)-N-BOC-CI | natural | 18 |
| (−)-N-BOC-DSA | unnatural | 0.06 |
| (−)-N-BOC-CCBI | unnatural | 0.08 |
| (−)-N-BOC-CBI | unnatural | 0.9 |
| (−)-N-BOC-MCBI | unnatural | 0.2 |
| (−)-N-BOC-DA | unnatural | 100 |
| epi-(−)-N-BOC-DA | unnatural | >100 |
| (+)-N-BOC-CBQ | unnatural | 11 |
| (−)-N-BOC-CI | unnatural | 18 |

FIG. 19

*In vitro* cytotoxic activity of TMI (trimethyloxyindole) derivatives.

| Agent | Configuration | IC$_{50}$ (pM, L1210) |
|---|---|---|
| (+)-duocarmycin SA | natural | 10 |
| (+)-CCBI-TMI | natural | 7 |
| (+)-CBI-TMI | natural | 30 |
| (+)-MCBI-TMI | natural | 200 |
| (+)-duocarmycin A | natural | 1600 |
| *epi*-(+)-duocarmycin A | natural | 4000 |
| (−)-CBQ-TMI | natural | 36000 |
| (±)-F$_2$CBI-TMI | racemic | 26000 |
| (+)-CI-TMI | natural | |
| (−)-duocarmycin SA | unnatural | 100 |
| (−)-CCBI-TMI | unnatural | 450 |
| (−)-CBI-TMI | unnatural | 2000 |
| (−)-MCBI-TMI | unnatural | 400 |
| (−)-duocarmycin A | unnatural | 23000 |
| *epi*-(−)-duocarmycin A | unnatural | 14000 |
| (+)-CBQ-TMI | unnatural | 35000 |
| (−)-CI-TMI | unnatural | 26000 |

FIG. 20

ANALOGS OF DUOCARMYCIN AND CC-1065

This is a 371 of PCT/US98/10535 May 22, 1988 which claims the benefit of PROVISIONAL APPLICATION No. 60/048,505 filed May 22, 1997.

UNITED STATES GOVERNMENT RIGHTS IN THE INVENTION

Funds used to support some of the studies reported herein were provided by the United States Government (National Institutes of Health Grant, Calif. 55276.) The United States Government, therefore, may have certain rights in the invention disclosed herein.

TECHNICAL FIELD OF THE INVENTION

The field of this invention is antitumor antibiotics. More particularly, the present invention relates to analogs of duocarmycin and CC-1065, which analogs have antitumor antibiotics activity.

BACKGROUND OF THE INVENTION

Duocarmycin SA(1) and duocarmycin A(2) constitute the parent members of a class of potent antitumor antibiotics related to CC-1065 (3) that derive their properties through a sequence selective alkylation of duplex DNA (FIG. 1). Since their disclosure, substantial efforts have been devoted to defining the characteristics of their DNA alkylation reactions, to determining the origin of their DNA alkylation selectivity, and to defining fundamental relationships between structure, functional reactivity, and biological properties.

Three models have been advanced to account for the DNA alkylation sequence selectivity. One model proposes a sequence-dependent phosphate protonation of the C4 carbonyl which activates the agent for DNA alkylation. (Warpehoski, M. A.; Hurley, L. H. *Chem. Res. Toxicol.* 1988, 1, 315; Hurley, L. H.; Reynolds, V. L.; Swenson, D. H.; Petzold, G. L.; Scahill, T. A. *Science* 1984, 226, 843. Reynolds, V. L.; Molineux, I. J.; Kaplan, D. J.; Swedson, D. H.; Hurley, L. H. *Biochemistry* 1985, 24, 6228. Hurley, L. H.; Lee, C.-S.; McGovren, J. P.; Warpehoski, M. A.; Mitchell, M. A.; Kelly, R. C.; Aristoff, P. A. *Biochemistry* 1988, 27, 3886. Scahill, T. A.; Jensen, R. M.; Swenson, D. H.; Hatzenbuhler, N. T.; Petzold, G.; Wierenga, W.; Brahme, N. D. *Biochemistry* 1990, 29, 2852; Hurley, L. H.; Warpehoski, M. A.; Lee, C.-S.; McGovren, J. P.; Scahill, T. A.; Kelly, R. C.; Mitchell, M. A.; Wicnienski, N. A.; Gebhard, I.; Johnson, P. D.; Bradford, V. S. *J. Am. Chem. Soc.* 1990, 112, 4633; Lin, C. H.; Beale, J. M.; Hurley, L. H. *Biochemistry* 1991, 30, 3597.) Another invokes alkylation at junctions of bent DNA without addressing the source of catalysis. (Lin, C. H.; Sun, D.; Hurley, L. H. *Chem. Res. Toxicol.* 1991, 4, 21. Lee, C.-S.; Sun, D.; Kizu, R.; Hurley, L. H. *Chem. Res. Toxicol.* 1991, 4, 203. Lin, C. H.; Hill, G. C.; Hurley, L. H. *Chem. Res. Toxicol.* 1992, 5, 167. Ding, Z.-M.; Harshey, R. M.; Hurley, L. H. *Nucl. Acids. Res.* 1993, 21, 4281. Sun, D.; Lin, C. H.; Hurley, L. H. *Biochemistry* 1993, 32, 4487. Thompson, A. S.; Sun, D.; Hurley, L. H. *J. Am. Chem. Soc.* 1995, 117, 2371.) A third model is based on the premise that distinct alkylation selectivities are controlled by the AT-rich noncovalent binding selectivity of the agents and their steric accessibility to the adenine N3 alkylation site. (Boger, D. L.; Johnson, D. S. *Angew Chem., Int. Ed. Engl.* 1996, 35, 1439. Boger, D. L.; Johnson, D. S. *Proc. Natl. Acad. Sci., U.S.A.* 1995, 92, 3642. Boger, D. L. *Acc. Chem. Res.* 1995, 28, 20. Boger, D. L. *In Advances in Heterocyclic Natural Product Synthesis*; Pearson, W. H., Ed.; JAI: Greenwich, 1992; Vol. 2, 1. Boger, D. L. *Chemtracts: Org. Chem.* 1991, 4, 329. Boger, D. L. In *Proc. R. A. Welch Found. Conf. Chem. Res.*, XXXV, *Chem. Frontiers Med.* 1991, 35, 137. Boger, D. L. In *Heterocycles in Bioorganic Chemistry*; Bergman, J.; van der Plas, H. C.; Simonyl, M., Eds.; Royal Soc. of Chem.: Cambridge, 1991; 103. Coleman, R. S.; Boger, D. L. In *Studies in Natural Product Chemistry*; Rahman, A.-u.-, Ed.; Elsevier: Amsterdam, 1989; Vol. 3, 301; Boger, D. L.; Johnson, D. S.; Yun, W.; Tarby, C. M. *Bioorg. Med. Chem.* 1994, 2, 115. Boger, D. L.; Munk, S. A.; Zarrinmayeh, H.; Ishizaki, T.; Haught, J.; Bina, M. *Tetrahedron* 1991, 47, 2661. Boger, D. L.; Coleman, R. S.; Invergo, B. J .; Sakya, S. M.; Ishizaki, T.; Munk, S. A.; Zarrinmayeh, H.; Kitos, P. A.; Thompson, S. C. *J. Am. Chem. Soc.* 1990, 112, 4623.) This latter proposal accommodates and explains the reverse and offset 5 or 3.5 base-pair AT-rich adenine N3 alkylation selectivities of natural and unnatural enantiomers of duocarmycin and CC-1065 and offers a beautiful explanation for the identical alkylation selectivities of both enantiomers or simple derivatives thereof. Further support for this model includes the demonstrated AT-rich noncovalent binding of the agents, their preferential noncovalent binding coincidental with DNA alkylation, the demonstration that the characteristic DNA alkylation is also observed with isomeric alkylation subunits (e.g., iso-CI and iso-CBI), and that it does not require the presence of the C4 carbonyl or even the activated cyclopropane.

In previous studies, the issue of catalysis with the noncovalent binding model has not been addressed. The chemical stability of duocarmycin and CC-1065 and the acid-catalysis requirement for addition of typical nucleophiles has led to the assumption that the DNA alkylation must also be an acid-catalyzed reaction. Although efforts have gone into supporting the extent and role of this acid catalysis, it remains largely undocumented for the DNA alkylation reaction. At pH 7.4, the DNA phosphate backbone is fully ionized (0.0001–0.00004% protonated). Consequently, it is unlikely that catalysis is derived from a phosphate backbone delivery of a proton to the C4 carbonyl as advanced in the alkylation site model. Consistent with this, the rate of the DNA alkylation reaction for duocarmycin SA exhibits only a very modest pH dependence below pH 7 and essentially no dependence in the more relevant pH 7–8 range.

BRIEF SUMMARY OF THE INVENTION

In one aspect, the present invention provides analog compounds of duocarmycin SA, duocarmycin A and CC-1065. An analog compound of the invention is represented by the following structure:

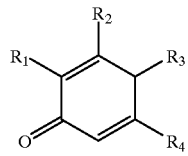

where said compound is fused to a first ring having a first vinylene group $V_1$ between $R_1$ and $R_2$, said first ring being one of the following structures, A, B, or C:

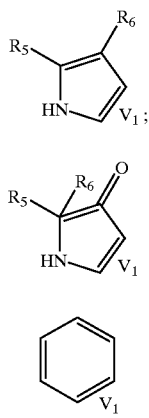

A

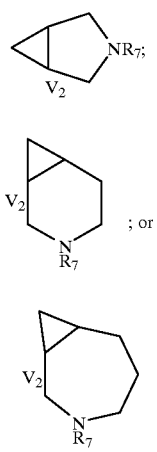

B

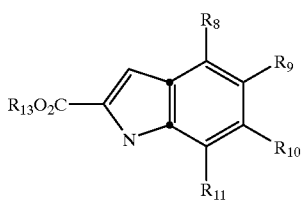

C where said compound is also fused to a second ring having a second vinylene group $V_2$ between $R_3$ and $R_4$, said second ring being one of the following structures, D, E, or F:

D

E; or

F wherein $R_5$ is a hydrogen, —$CO_2(C_1$–$C_6(alkyl))$ or a radical represented by the following structure, G:

G where $R_6$ is hydrogen or $C_1$–$C_6$(alkyl); $R_7$ is —H, —$CO_2$($C_1$–$C_6$(alkyl)), —$CO(C_1$–$C_6$(alkyl)), —$CO_2$-tert-butyl, or —$COR_{14}$; $R_8$ is hydrogen or a first N-substituted pyrrolidine ring being fused at a third vinylene group $V_3$ between $R_8$ and $R_9$ represented by the following structure, H:

where $R_9$ is: —NH—C(O)—; $R_{10}$ and $R_{11}$ are each independently hydrogen, —O—$C_1$–$C_6$(alkyl) or —$C_1$–$C_6$(alkyl), wherein the —NH group is directly attached to G at the $R_9$ position and the C(O)— group is directly attached to the first ring at the $R_5$ position, if $R_8$, $R_{10}$ and $R_{11}$ are each hydrogen; said first N-substituted pyrolidine ring radical, H, being fused at the third vinylene group $V_3$ between $R_8$ and $R_9$; and a radical represented by the structure, I:

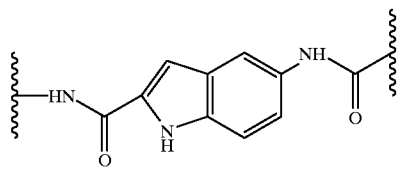

I wherein the —NH group is directly attached to G at the $R_9$ position and the C(O)— group is directly attached to the first ring at the $R_5$ position, if $R_8$, $R_{10}$ and $R_{11}$ are each hydrogen; with the following provisos:

if $R_8$ participates in the first N-substituted pyrrolidine ring, then $R_9$ also participates in the first N-substituted pyrrolidine ring;

if $R_9$ participates in the first N-substituted pyrrolidine ring, then $R_8$ also participates in the first N-substituted pyrrolidine ring;

if $R_8$ and $R_9$ participate in the first N-substituted pyrrolidine ring, then $R_{10}$ and $R_{11}$ are hydrogen; $R_{12}$ is —C(O)— and a diradical represented by the following structure, J:

J wherein the —C(O) group is directly attached to H at the $R_{12}$ position and the N—C(O)— group is directly attached to the first ring at the $R_5$ position; $R_{13}$ is hydrogen or $C_1$–$C_6$(alkyl); $R_{14}$ is hydrogen, $C_1$–$C_6$(alkyl), —O—($C_1$–$C_6$(alkyl)), or a radical represented by the structure, K:

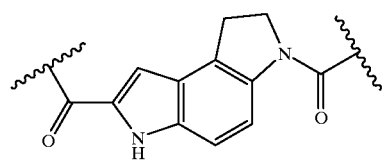

K where $R_{15}$ is hydrogen or a second N-substituted pyrolidine ring being fused at a fourth vinylene group $V_4$ between $R_{15}$ and $R_{16}$ represented by the following structure, L:

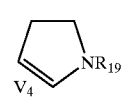

L where $R_{16}$ is:

—O—($C_1$–$C_6$(alkyl)), $C_1$–$C_6$(alkyl), $NH_2$ or said second N-substituted pyrolidine ring radical, L, being fused at a fourth vinylene group $V_4$ between $R_{15}$ and $R_{16}$; or a radical represented by the following structure, M:

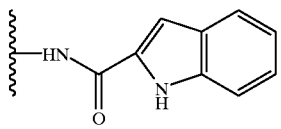

wherein the —NH group is directly attached to K at the $R_{16}$ position if $R_{15}$, $R_{17}$ and $R_{18}$ are each hydrogen; with the following provisos:
  if $R_{15}$ participates in the first N-substituted pyrrolidine ring, then $R_{16}$ also participates in the first N-substituted pyrrolidine ring;
  if $R_{16}$ participates in the first N-substituted pyrrolidine ring, then $R_{15}$ also participates in the first N-substituted pyrrolidine ring;
  if $R_{15}$ and $R_{16}$ participate in the first N-substituted pyrrolidine ring, then $R_{17}$ and $R_{18}$ are hydrogen;
  where $R_{17}$ and $R_{18}$ are independently hydrogen, —O—$C_1$–$C_6$(alkyl) or —$C_1$–$C_6$(alkyl); $R_{19}$ is —C(O)—$R_{20}$ or a radical represented by the following structure, N:

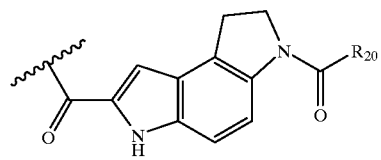

wherein the —C(O) group is directly attached to the second N-substituted pyrrolidine ring, L, at the $R_{19}$ position; and $R_{20}$ is $NH_2$ or —O-tert-butyl; the compound not being (+)-CC-1065, (+)-duocarmnycin SA, or (+)-duocarmnycin A. Compounds are shown herein with a particular enantiomer configuration. One of skill in the art will readily appreciate that all enantiomers of the compounds are contemplated as being a part of this invention.

In a preferred embodiment, a compound has A as the first ring. A preferred second ring is D. Exemplary and preferred compounds have the structures set forth hereinafter as reversed, sandwiched, shortened, simplified, and extended analogs. Further preferred compounds have a six- or seven member heterocyclic ring as part of the alkylation subunit.

In another aspect, the present invention provides a pharmaceutical composition containing a compound of formula I together with a physiologically acceptable diluent.

Still further, the present invention provides a process of alkylating DNA, the process including the step of exposing DNA to a compound or composition of this invention.

BRIEF DESCRIPTION OF THE DRAWINGS

In the Drawings, which form a portion of the specification:

FIG. 1 shows the structures of duocarmycin SA, duocarmycin A and CC-1065.

FIG. 8 shows the structure and synthetic scheme for making analog compounds 60–62.

FIG. 11, shown in two panels as FIGS. 11a and 11b, shows the summary results of consensus DNA alkylation sequences alkylated by compounds of the present invention.

FIG. 12 shows summary data of the consensus alkylation sequence alkylated by further compounds of this invention.

FIG. 13 shows sequence preferences for analog compounds of the invention.

FIG. 14 shows in vitro cytotoxic activity of analog compounds of the invention containing indole derivatives.

FIG. 15 shows summary data of DNA alkylating efficiency of analog compounds of the invention.

FIG. 16 shows consensus sequences for DNA alkylation by key components in analog compounds of the present invention.

FIG. 17 shows the structure and synthetic scheme for making analog compounds 99–102.

FIG. 19 shows the in vitro cytotoxic activity of BOC derivatives analogs of the invention.

FIG. 20 shows the in vitro cytotoxic activity of trimethyloxyindole derivatives analogs of the invention.

DETAILED DESCRIPTION OF THE INVENTION

I. The Invention

The present invention provides compounds that are analogs or derivatives of duocarmycin A, duocarmycin SA and CC-1065, compositions containing those compounds and the use of those compounds and compositions for alkylating DNA.

II. Compounds

A. Reversed and Sandwiched Analogs

Duocarmycin SA (1) contains a C6 methyl ester that complements the right-hand side linking amide. This provides the opportunity to introduce DNA binding subunits on either side of the alkylation subunit. Thus, coupling of a DNA binding subunit through the C6 carboxylate provides a novel class of agents referred to herein as reversed analogs. The reversed compounds (17–20, 23, 24 FIG. 2–3) exhibit an AT-rich alkylation selectivity that extends in the atypical reverse direction from an alkylation site. The predicted alkylation sites for the natural enantiomers coincide with those of the unnatural enantiomers of the typical extended agents. The predicted alkylation sites for the unnatural enantiomers of the reversed agents coincide with those of the natural enantiomers of the extended agents. Thus, a complete switch in the enantiomeric alkylation selectivity would be observed with the reversed analogs if it is controlled by the AT-rich binding selectivity. In contrast, the alkylation site model would require that natural enantiomers of both the extended and reversed agents alkylate the same sites rather than exhibit this switch.

Figure 2:
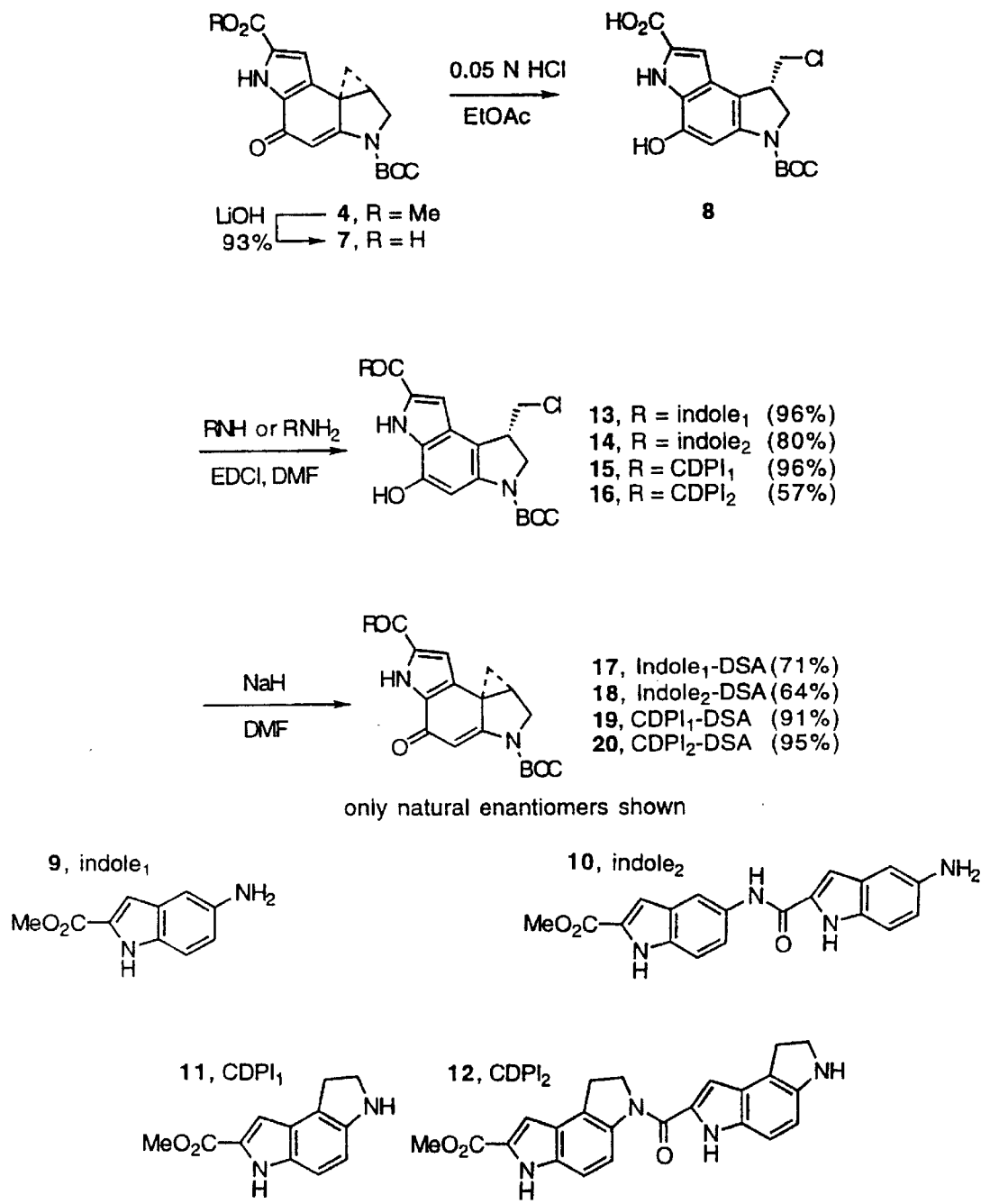
FIG. 2 shows the structure and method of making analog compounds 17–20.

Synthesis of the Reversed Analogs of Duocarmycin SA. The preparation of 17–20 was accomplished through coupling of the free amine of 9–12 (0.9 equiv, 2–4 h, 25° C.) with the C6 carboxylic acid of 8 (FIG. 2). While this was conducted as outlined in FIG. 2, the manner in which this could be accomplished was not straightforward. Hydrolysis (1–1.3 equiv LiOH) of N—BOC-DSA (4) cleanly provided 7 (93%) without competitive hydrolysis of the carbamate or addition to the cyclopropane. Prolonged reaction times (72 h) at 25° C. under typical conditions (LiOH, THF—CH$_3$OH—H$_2$O) provided predominately recovered starting material and the conversion to 7 was observed only upon warming (60° C.). Even under these conditions, only methyl ester hydrolysis was observed. Both the direct coupling of 7 (DCC, EDCI, DEPC) in the presence or absence of added NaHCO$_3$ or the use of preformed active esters (e.g, imidazolide) provided only low yields (10–30%) of the desired agent with the more soluble coupling partners and failed altogether with the insoluble CDPI$_2$. Consequently, the preparation of 17–20 was more effectively accomplished in an indirect manner. Treatment of 7 with dilute HCl (0.05 N HCl-EtOAc, 25° C., 30 min) provided 8 without N—BOC deprotection and no trace of the ring expansion HCl addition product was detected. Subsequent coupling of 8 with the 9–12 (0.9 equiv, 2 equiv EDCI, DMF, 2–4 h, 25° C.) proceeded in high yields (57–96%) and spirocyclization was effected by NaH (DMF, 0° C., 30 min, 64–95%).

Figure 3:
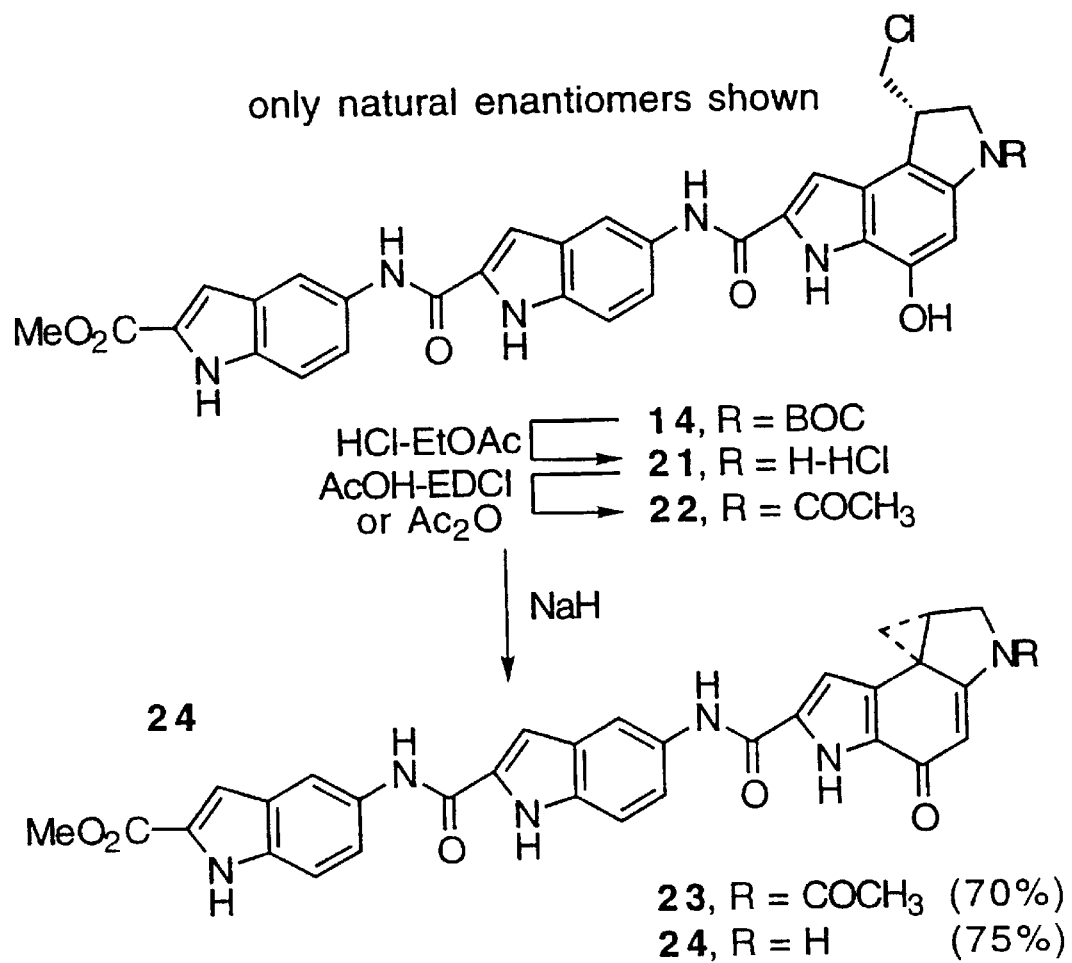
FIG. 3 shows the structure and synthetic scheme for making analog compounds 23 and 24.

Modifications in the Terminal N$^2$ Acyl Substituent of the Reversed Analogs. To insure that the behavior of 17–20 was not substantially influenced by the nature of the N$^2$ substituent, both enantiomers of 23 and 24 terminating with a N$^2$-acetyl group or the free amine were prepared (FIG. 3). Thus, N—BOC deprotection of 14 (3.4 N HCl-EtOAc, 25° C., 30 min) followed by spirocyclization or N$^2$ acetylation and spirocyclization afforded 24 and 23, respectively.

Figure 4:
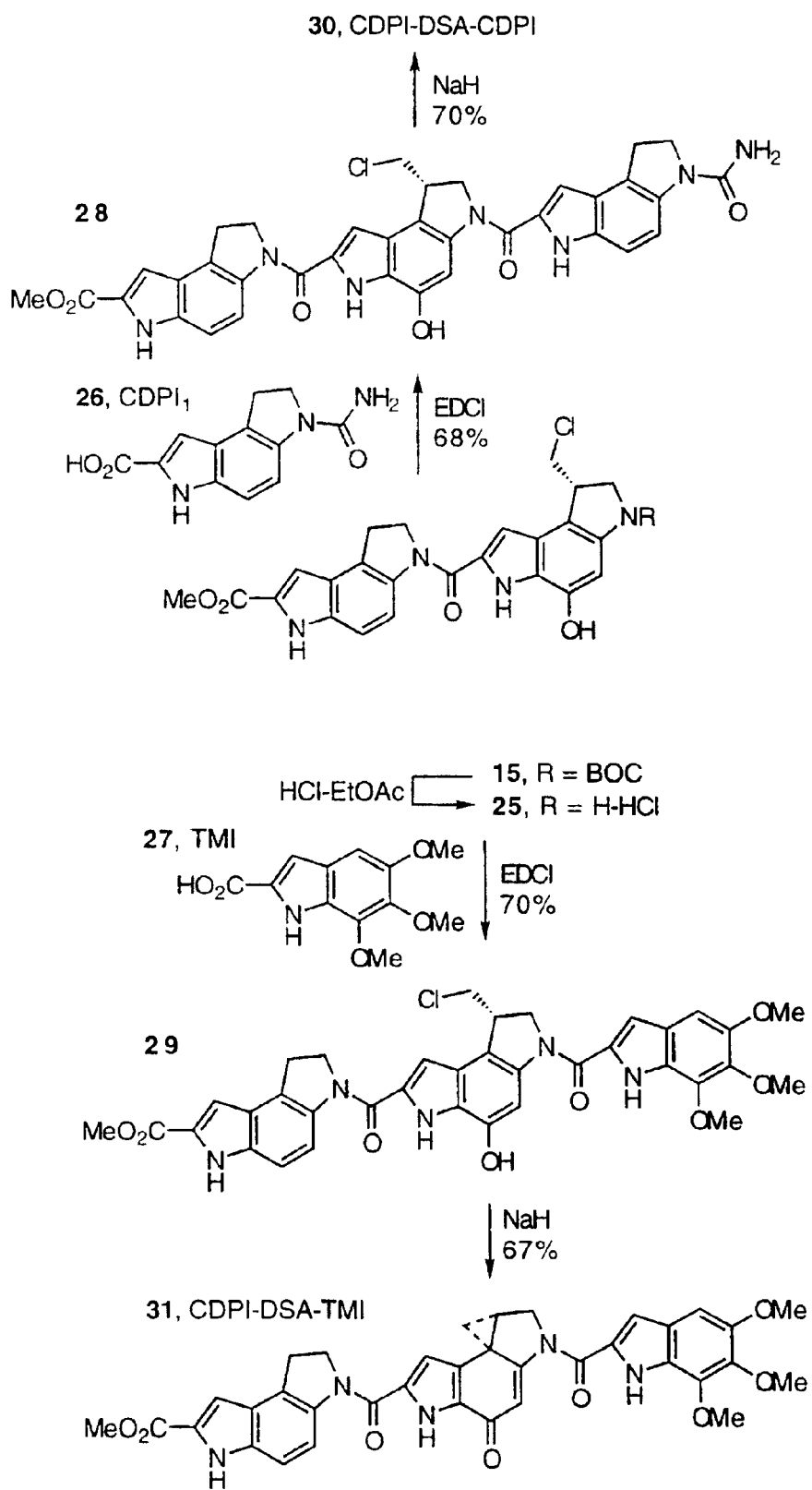
FIG. 4 shows the structure and synthetic scheme for making analog compounds 30 and 31.

Synthesis of the Sandwiched Analogs of Duocarmycin SA. An important complement to the extended and reversed analogs are the agents 30 (CDPI-DSA-CDPI) and 31 (CDPI-DSA-TMI) (FIG. X) referred to herein as sandwiched analogs (FIG. 4). Their examination was more informative than their initial consideration might suggest. The noncovalent binding model led us to predict that both enantiomers of 30 and 31 would alkylate the same sites independent of their absolute configuration and that their sites of DNA alkylation would be distinct from either enantiomer of both the extended and reversed analogs. Such a demonstration would further distinguish the noncovalent binding model from the alkylation site model which would require that the natural enantiomers of the sandwiched analogs alkylate the same sites as (+)-1–6. Compounds 30 and 31 were prepared using N—BOC deprotection of 15 (4 N HCl-EtOAc, 25° C., 30 min) followed by coupling of 25 with CDPI$_1$ (26, 68%) or 27 (0.95 equiv, 2 equiv EDCI, DMF, 25° C., 6–15 h, 70%) and spirocyclization (NaH, DMF, 0° C., 30 min) cleanly provided 30 (70%) and 31 (67%) (FIG. 4).

B. Shortened Simplified and Extended Analogs

Figure 5:
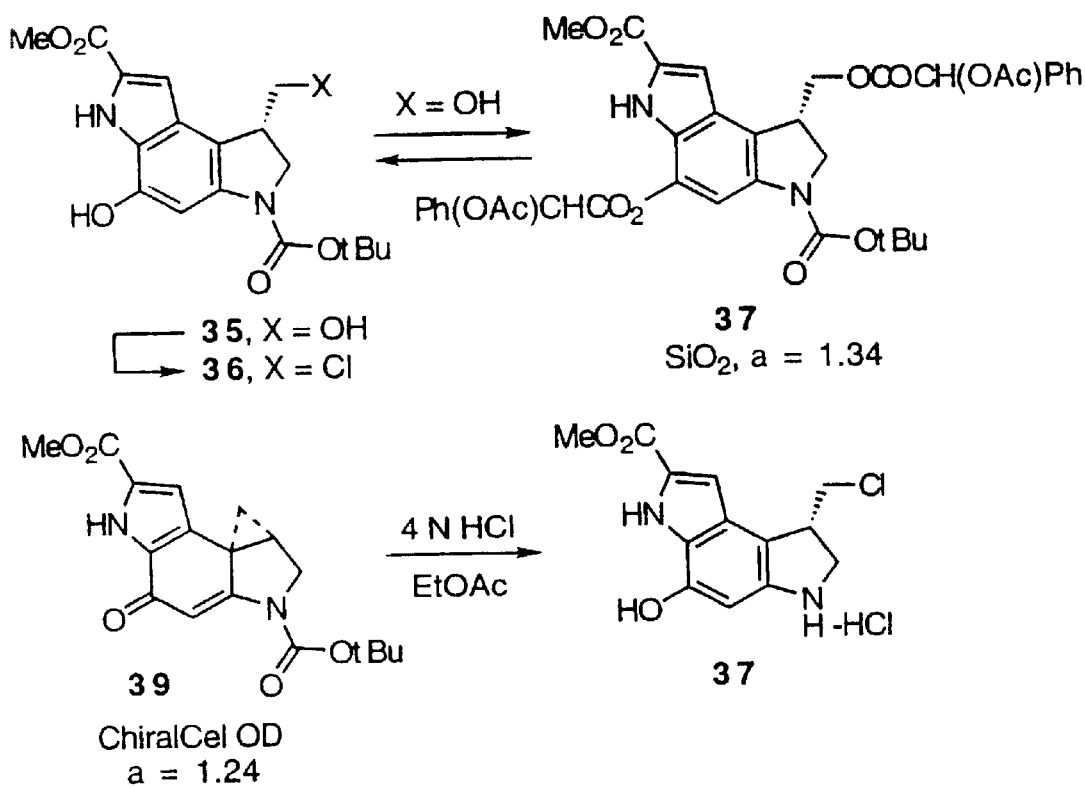
FIG. 5 shows the synthetic scheme for making analog compound 37 and the structure of that compound.

Resolution of N—BOC-DSA. Optically active agents were prepared through chromatographic resolution of the bis-(R)—O-acetylmandelate ester of 37 or, more conveniently, through a new protocol of direct chromatographic resolution of N—BOC-DSA (39). Although the immediate precursors to 39 including 35 and 36 were not resolved by direct chromatographic means, the enantiomers of N—BOC-DSA were effectively separated on a semi-preparative ChiralCel OD HPLC column (10 μm 2×25 cm, 30% 2-propanol/hexane, 7 mL/min, α=1.24, ≧99.9% ee). Acid-catalyzed deprotection of 39 (4 N HCl-EtOAc, 25° C., 30 min, 95–100%) was accompanied by clean addition of HCl to the cyclopropane and provided 33 (FIG. 5). Notably, no trace of the ring expansion product derived from addition of chloride to the more substituted C8a cyclopropane carbon was detected.

Figure 6:
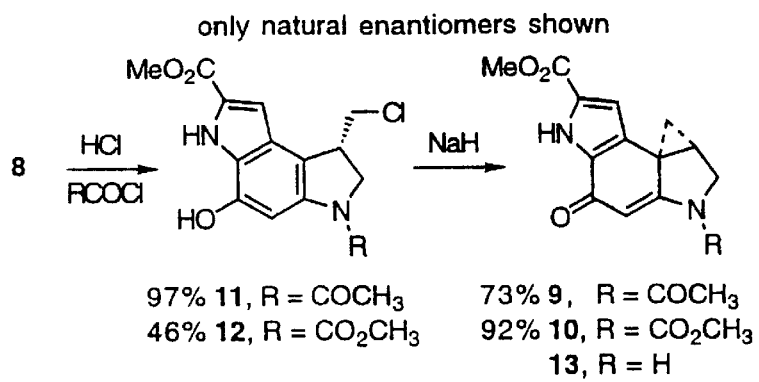
FIG. 6 shows the structure and synthetic scheme for making analog compounds 40 and 41.

Simple Derivatives of the Alkylation Subunit. In studies that culminated in the total synthesis of (+)- and ent-(−)-1, we detailed the synthesis and examination of both enantiomers of N—BOC-DSA (39) and 44. To generalize the properties of such simple derivatives, both enantiomers of 40 and 38 were prepared (FIG. 6). Treatment of 39 with 4 N HCl-EtOAc (25° C., 30 min) followed by acylation with acetyl chloride or methyl chloroformate (2.0 equiv, 3.0 equiv NaHCO$_3$, THF, 25° C., 1 h) provided 42 (97%) and 43 (46%). Spirocyclization to provide 40 (73%) and 41 (92%) was effected by treatment with NaH.

Figure 7:
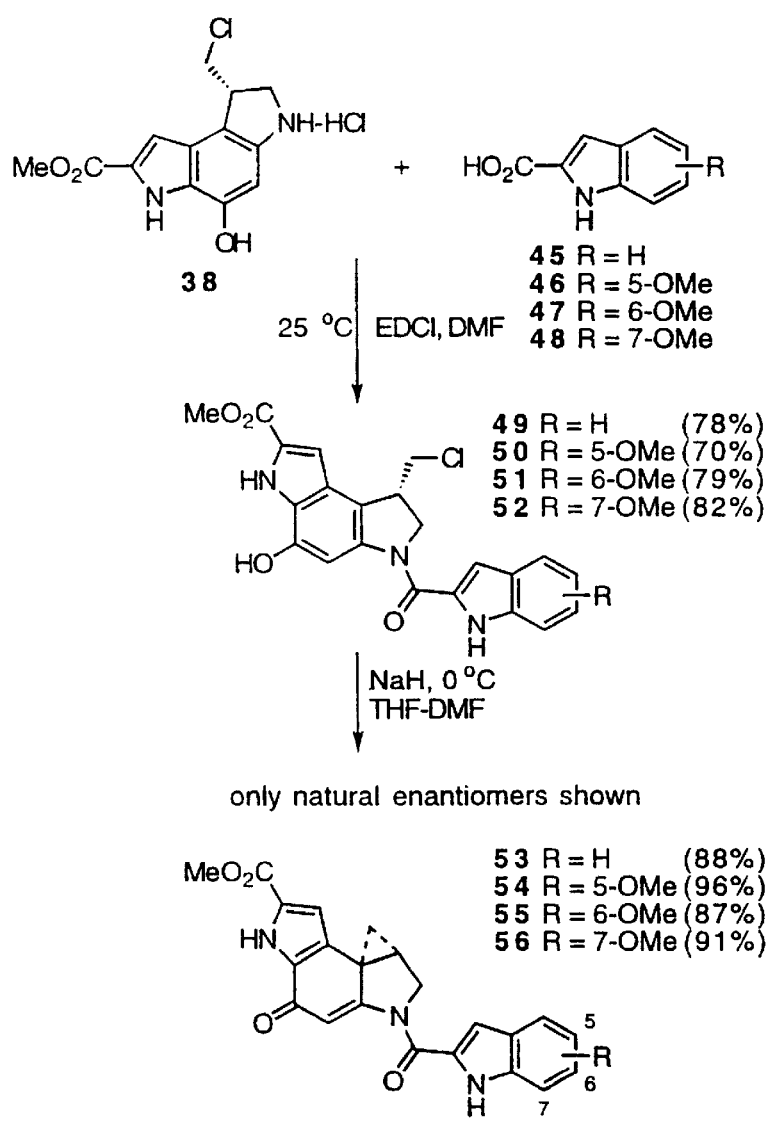
FIG. 7 shows the structure and synthetic scheme for making analog compounds 53–56.

Modifications in the Right-hand Subunit: Role of the Methoxy Substituents. Modifications in the trimethoxyindole subunit of duocarnycin SA were made with the intention of defining the role of each of the three methoxy substituents. Treatment of 39 with 4 N HCl-EtOAc (25° C., 30 min) followed by coupling (3 equiv EDCI, DMF, 25° C., 4–15 h) of 38 with 45–48 (1.1 equiv) in the absence of added base provided the precursors 49–52 (70–82%, FIG. 7). Spirocyclization was effected by treatment with NaH (3 equiv, THF-DMF 4–2:1, 0° C., 30 min) to provide of 53–56 (87–96%). Coupling of 38 in the presence of base including NaHCO$_3$ led to competitive spirocyclization and the presence of adventitious moisture in the spirocyclization reaction mixture led to subsequent hydrolysis of the linking N$^2$ amide.

Substitutions for the DNA Binding Subunit: Extended Analogs. Three additional DNA binding subunits have proven representative and important to examine. These include CDPI$_1$, CDPI$_2$, and indole$_2$. The former typically provides agents analogous to 1–2 while the latter two derivatives are representative of the larger agents which exhibit a more extended 5 base-pair AT-rich DNA alkylation selectivity analogous to CC-1065 (3). In addition, the indole$_2$ derivatives maintain the cytotoxic potency of 1–3, but typically exhibit more efficacious in vitro antitumor activity. The agents were prepared by acid-catalyzed deprotection of 39 (4 N HCl-EtOAc, 25° C., 15–20 min) followed by immediate coupling (3 equiv EDCI, DMF, 12–24 h, 25° C.) of 37 with CDPI$_1$ (67%), CDPI$_2$ (67%), and indole$_2$ (81%) conducted in the absence of added base (FIG. 8). Spirocyclization to provide 60–62 was effected by treatment with NaH.

C. Analogs Incorporating an Alkylation Subunit Containing a b or 7 Member Heterocycle Synthesis of N—BOC-CNA (78) and CNA (79). Attempts to extend the radical cyclization methodology employed for the five- and six-membered C-ring analogs in this class were unsuccessful. Reaction of the appropriately functionalized naphthalene with Bu$_3$SnH-AIBN (R=H, +TEMPO) resulted in simple reduction. The metal hydride reduction of the resulting aryl radical proved faster than the required 7-exo-trig radical cyclization even with substrates bearing an activated acceptor alkene.

Figure 9:
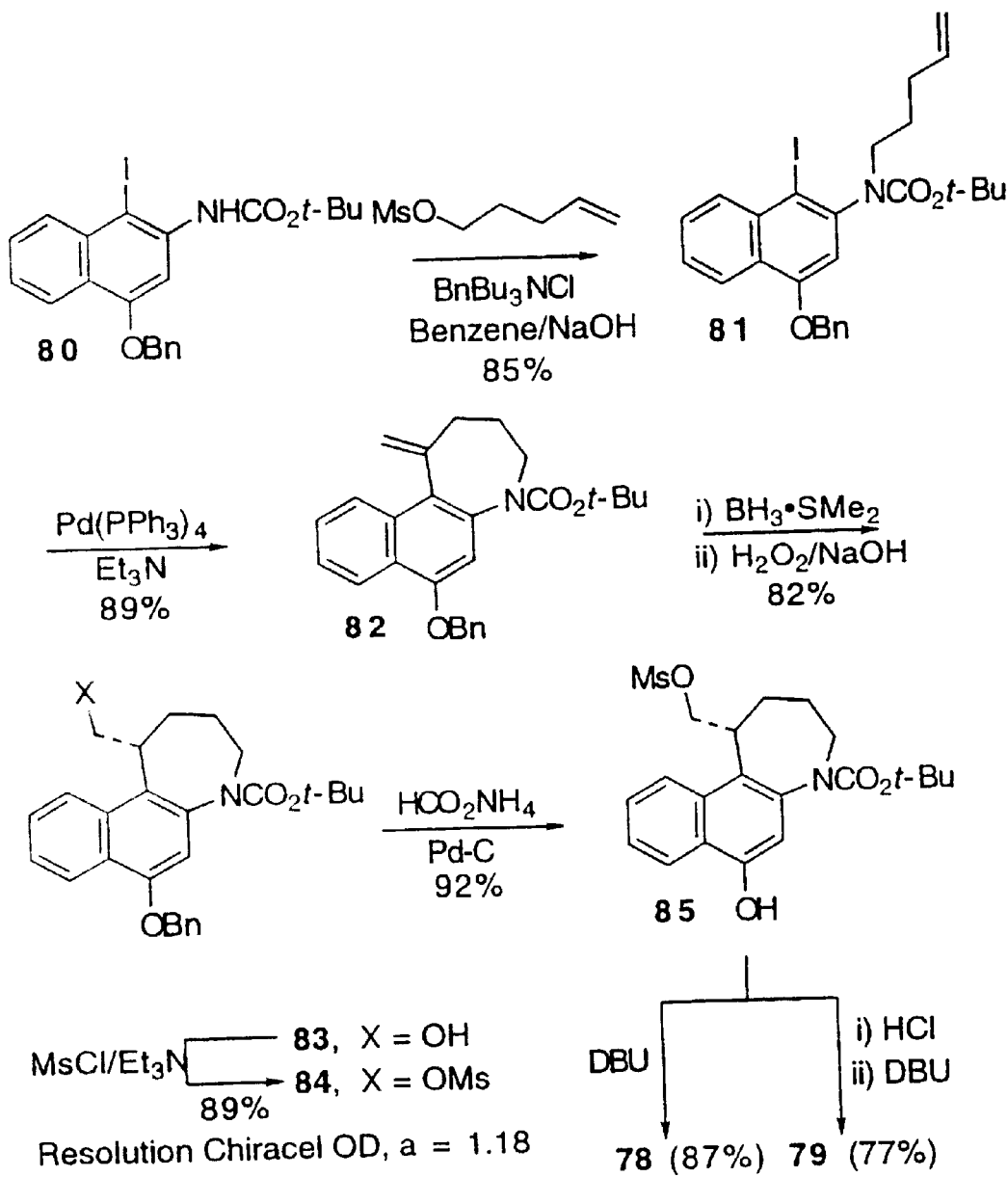
FIG. 9 shows the synthetic scheme for making analog compounds 78 and 79.

The successful approach to the preparation of the CNA nucleus rested on the implementation of an alternative intramolecular Heck reaction. The starting material for both the Heck reaction and the radical cyclization attempts was prepared by N-alkylation of N-(tert-butyloxy-carbonyl)-4-(benzyloxy)-1-iodo-2-naphthylamine (80), readily available in three steps (60% overall) from 1,3-dihydroxynaphthalene, with the mesylate of 4-penten-1-ol to provide 81 (FIG. 9). A full two molar equivalents of benzyltributylammonium chloride was required to provide high yields of the alkylated product using phase transfer conditions. An intramolecular Heck reaction conducted with 3 mole % of Pd[P(Ph$_3$)]$_4$ as catalyst furnished the desired cyclization product 82 in 89%. Careful removal of O$_2$ from the reaction mixture provided reproducible high yields and no palladium hydride induced isomerization of 83 to give the endocyclic olefin was detectable by $^1$H NMR of the crude reaction mixture.

Similar observations were made with the substrate (R=CO$_2$CH$_3$) bearing an activated electron-deficient acceptor alkene, but the reaction proved unsuccessful with the substrate (R=OTHP) bearing an electron-rich acceptor alkene. In principle, both successful cyclization products can be converted into appropriately C-1 substituted and functionalized tetrahydronaphtho[2,1-b]azepines for use in the preparation of 78–79.

Hydroboration followed by oxidative workup converted the exocyclic olefin into the desired alcohol 83. Efforts to convert this alcohol to the corresponding chloride upon treatment with Ph$_3$P—CCl$_4$ proceeded in modest yields (ca. 50%). Much higher conversions were realized by treatment of 83 with mesyl chloride in the presence of Et$_3$N to provide 84 in 89%. Removal of the benzyl group through transfer hydrogenolysis (4 wt. equiv of 10% Pd—C, aqueous HCO$_2$NH$_4$—THF, 25° C., 2 h, 89%) afforded 85 and set the stage for the final spirocyclization.

Winstein Ar-3' spirocyclization was effected by treatment of 85 with DBU (3 equiv, CH$_3$CN) and smoothly provided 78 (87%). Due to its unusual reactivity, careful chromatographic conditions were required and pretreatment of the chromatographic support (SiO$_2$) with Et$_3$N resulted in much higher yields (i.e., 87% versus 40–50%). Treatment of 85 with 3.9 M HCl-EtOAc removed the BOC group to afford the unstable amine hydrochloride which was taken directly into the subsequent cyclization step. Addition of 10 equiv of DBU as a dilute solution in CH$_3$CN resulted in good conversion to 79 (77%). Conventional chromatography provided the relatively stable CNA which gave crystals suitable for X-ray analysis (CH$_3$CN—CH$_3$OH).

Figure 10:
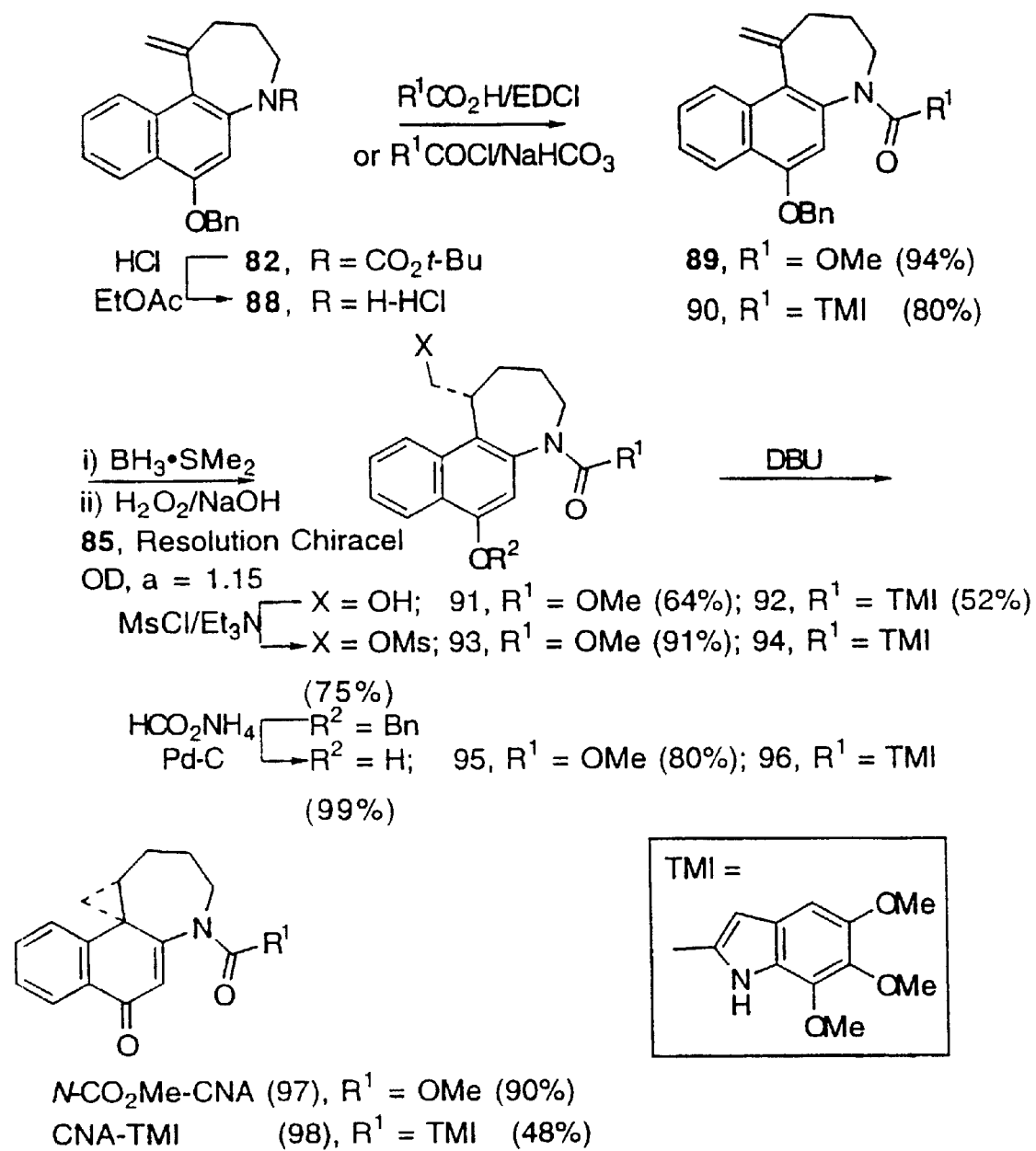
FIG. 10 shows the structure and synthetic scheme for preparing analog compounds 97 and 98.

Synthesis of N—CO$_2$Me-CNA (97) and CNA-TMI (98). Efforts to acylate the amine hydrochloride resulting from BOC deprotection of 85 at this late stage in the synthesis were unsuccessful. The only azepine amenable to N-acylation was the free amine derived from 83 which bore the exocyclic olefin. Incorporation of the sp$^2$ hybridized carbon presumably alters the conformation of the fused seven-membered ring in a manner that allows N-acylation. Synthesis of the amine hydrochloride 88 through treatment with 3.9 N HCl-EtOAc (25° C., 40 min) provided a relatively well-behaved solid amine salt that served as a short tenn storage intermediate for further acylations (FIG. X). Liberation of the free amine with NaHCO$_3$ followed by treatment with methyl chloroformate provided 89 in 94% yield. High yields (80%) were also realized for EDCI coupling of 88 and 5,6,7-trimethoxyindole-2-carboxylic acid to form the advanced analog 90. Exposure of the acylated products to the same sequence of synthetic transformations detailed for 78–79 gave good to excellent yields of the desired products 91–96. Unlike N—BOC-CNA (78), N—CO$_2$Me-CNA (97) proved to be a crystalline solid and recrystallization from 10% EtOAc-hexanes gave X-ray quality crystals. Spirocyclization of TMI derivative 96 gave a lower yield of ring closed product 96 (48%) due to its high reactivity and more challenging chromatography requirements for purification (FIG. 10).

Resolution. In order to obtain the separate enantiomers of both 78 and 96, various synthetic intermediates were subjected to direct chromatographic resolution on a semi-preparative chiracel OD column. The intermediates 84, 87 and 92 proved to have the greatest separation and were resolved (>99.9% ee) in sufficient quantities to be carried on to the respective final products. The assignment of the absolute configuration for (+)-78 was based initially on the relative cytotoxic potencies of (+)- and ent-(−)-N—BOC-CNA, with the former exhibiting more potent activity which is consistent with observations made for 1–3 and 76–77. Ultimately, the absolute configuration for (+)-78 was confirmed and unambiguously established by X-ray structure analysis[24] of the resolved seco-derivative (−)-(1R)-87 bearing a heavy atom and subsequent conversion to (+)-78.

A detailed description of the synthesis of compounds of this invention is set forth hereinafter in the Examples. The present invention further contemplates intermediates formed during synthesis of those compounds. This invention still further contemplates compositions containing a compound of the invention as set forth above.

Preferably, the composition is an aqueous composition.

III. Uses

Compounds of this invention alkylate selective sequences in DNA target molecules. The compounds thus have cytotoxic activity and can be used as antitumor antibiotics. Details of the activity of particular compounds are set forth below.

A. Reversed and Sandwiched Analogs

DNA Alkylation Studies. The DNA alkylation properties of the reversed and sandwiched agents were examined within five segments of duplex DNA. With both enantiomers of the reversed analogs CDPI$_2$DSA (20) in hand, their comparison with the enantiomers of DSA-CDPI$_2$ was addressed. The key question was whether the enantiomeric alkylation selectivity of 20 would switch with the simple reversal of the orientation of the DNA binding subunits (noncovalent binding model) or whether the two natural enantiomers would behave in an identical or comparable manner (alkylation site model).

The natural enantiomer of the reversed agent, (+)-CDPI$_2$-DSA (20), was found to alkylate the same sites and to exhibit the same sequence selectivity as the unnatural enantiomer of CC-1065 and the extended agent, ent-(−)-DSA-CDPI$_2$. Thus, a complete reversal of the enantiomeric alkylation selectivity was observed with (+)-20 and these results are only consistent with the noncovalent binding model. The natural enantiomer of the reversed analog (+)-CDPI$_2$-DSA (20) alkylated the same, single high affinity site in w794 (5'-A<u>A</u>TTT) as the unnatural enantiomers (-CC-1065 and (−)-DSA-CDPI$_2$ without detectable alkylation at the single, high affinity site observed with the natural enantiomers (+)-CC-1065 and (+)-DSA-CDPI$_2$ (5'-AATT<u>A</u>).

Within the six-base A-rich sequence of w836 DNA (+)-duocarmyein SA alkylated each of the four 3' adenines (5'-AA<u>AAAA</u>) corresponding nicely to 3'→5' binding across a 3.5 base-pair AT-rich site. The natural enantiomer of the extended analog (+)-DSA-CDPI$_2$ also alkylates only the 3' adenines (5'-AAA<u>AAA</u>) in this sequence corresponding to the same 3'→5' binding but across a more extended 5 base-pair AT-rich sequence restricting alkylation to the first three versus four 3' adenines. In this same sequence, the unnatural enantiomer of the extended agent, ent-(−)-DSA-CDPI$_2$, alkylates the 5' terminal adenines in accordance with 5'→3' binding across a 5 base-pair AT-rich binding site (5'-A<u>AAAA</u>A). Consistent with the offset AT-rich binding site of the unnatural enantiomers due to the diastereomeric nature of the adducts, ent-(−)-DSA-CDPI$_2$ does not alkylate the terminal 5' adenine, but does alkylate the following four 5' adenines. Indicative of the complete switch in the enantiomeric alkylation selectivity of the reversed agents, the natural enantiomer of 20 alkylated the same sites as ent-(−)-DSA-CDPI$_2$ while the unnatural enantiomer of 20 alkylated the same sites as the natural enantiomer (+)-DSA-CDPI$_2$. In addition to establishing that the noncovalent binding selectivity of the agents is controlling the DNA alkylation selectivity, the comparisons also establish that the two enantiomers are subject to the same polynucleotide recognition features. In related studies, it is maintained that the two enantiomers are subject to different polynucleotide recognition elements.

The consensus alkylation sequence of (+)-CDPI$_2$-DSA (20) is summarized in FIGS. 11b and 11b. All alkylation sites were found to be adenine and essentially each adenine N3 alkylation site was flanked by a 5' and 3' A or T base. The preference for this three-base sequence followed the order: 5'-AAA>5'-AAT≧5'-TAA>5'-TAT). There was also a strong preference for the second and third 3' base to be A or T and the preferences distinguished the high affinity versus lower affinity alkylation sites. Thus, (+)-CDPI$_2$-DSA exhibits a 5 base-pair AT-rich alkylation selectivity that corresponds to 5'→3' binding in the minor groove starting at the 5' base preceding the alkylation site and extending over the alkylated adenine in the 3' direction covering the three adjacent 3' bases, e.g. 5'-AAAAA.

The consensus alkylation selectivity of (−)-CDPI$_2$-DSA is also summarized in FIGS. 11a and 11b. All alkylation sites were found to be adenine and essentially each adenine N3 alkylation site was flanked by two 5' A or T bases. The preference for this three-base sequence followed the order: 5'-AAA>5'-TAA>5'-TTA>5'-ATA. There was also a preference for the third and fourth 5' bases to be A or T and this distinguished the high affinity versus low affinity sites. Thus, (−)-CDPI$_2$-DSA exhibits a 5 base-pair AT-rich alkylation selectivity starting at the alkylated adenine and extending in the 3'→5' direction across the four adjacent 5' bases, e.g. 5'-AAAAA.

Examination of 17–19 revealed the same characteristics except that they exhibited either a 5 (18) or 3.5 (17 and 19) base-pair AT-rich selectivity corresponding to their sizes and lengths. CDPI$_1$-DSA (19) was found to behave analogous to duocarmycin SA albeit with the reversed enantiomeric alkylation selectivity. With w794 DNA, the natural enantiomers of 17–20 preferentially alkylate the single high affinity site of the unnatural enantiomers of 1–3 and do not alkylate the typical natural enantiomer site. The smaller and shorter reversed analogs also proved less efficient at alkylating DNA. This efficiency followed the predictable trends of 20>18>19>17 and was more sensitive to the size of the agents than the typical extended agents. Moreover, the full set of reversed analogs 17–20 alkylated DNA at substantially slower rates and ultimately with lower efficiencies. Typically, the reactions for the reversed analogs were conducted at 37° C. for 5 days (versus 25° C., <12 h) and even then were 10–1000× less efficient than 1–3 and related agents. In fact, their behavior proved more similar to the simple derivatives 4–6 than 1–3.

DNA Alkylation Properties of Agents Containing Modifications in the Terminal N$^2$ Substituent of the Reversed Analogs. The agents 23 and 24 were examined in efforts to determine whether the terminal N$^2$-BOC group of the reversed analogs was contributing to their reduced rate and efficiency of DNA alkylation. The three agents exhibited no differences in their DNA alkylation selectivity and only small differences in both the rate and efficiency of DNA alkylation. Moreover, the magnitude of these differences was much smaller than might be anticipated. The acetyl derivative 23 was found to be 2–5× more efficient than the BOC derivative 18, and the terminal NH agent 24 was about an order of magnitude less efficient than 18. While these trends nicely follow the expected relative reactivities of the agents (23>18>>24), all three were still substantially slower (ca. 1000×) and much less efficient (ca. 100×) at alkylating DNA than the typical extended analog DSA-indole$_2$. The unnatural enantiomers of 23 and 24, like that of 18, were approximately 10× less effective than the natural enantiomers.

DNA Alkylation Properties of the Sandwiched Analogs of Duocarmycin SA. Consistent with the noncovalent binding model, both enantiomers of CDPI-DSA-CDPI (30) alkylated the same sites and their selectivity proved distinct from either enantiomer of the extended or reversed agents DSA-CDPI$_2$ or CDPI$_2$-DSA (20). The consensus alkylation sequence for (+)- and ent-(−)-30 is summarized in FIG. 12. All alkylation sites were found to be adenine and essentially all adenine N3 alkylation sites were flanked by a 5' and 3' A or T base. The preference for this three-base sequence follows the order: 5'-AAA>5'-AAT≧5'TAA>5 TAT. In addition, there was a very strong preference for both of the second 5' and 3' bases to be A or T. Exceptions typically involved one but not both of these locations and the preference was strongest on the 5' side of the alkylation site, e.g. 5'-AAAG>5'-CAAAA. Thus, alkylation was observed at adenines central to a 5 base-pair AT-rich sequence, e.g. 5'-AAAAA. With w836 DNA, (+)- and ent-(−)-30 exhibited identical alkylation profiles within the stretch of six adenines and alkylated those central to the sequence rather than the 3' or 5' terminal adenines characteristic of (+)- or ent-(−)-DSA-CDPI$_2$. Very few of the alkylation sites overlap with those of either enantiomer of the extended or reversed analogs and those that do are typically found in a long stretch of A's containing multiple alkylation sites for all agents.

Models of the DNA Alkylation Reactions. Both enantiomers of N—BOC-DSA exhibit an identical 2 base-pair alkylation selectivity (5'-AA>5'-TA) with a requirement for a single 5' A or T base adjacent to the adenine N3 alkylation site. For the natural enantiomer, this involves 3' adenine N3 alkylation with agent binding in the 3'→5' direction relative to the alkylated strand across the adjacent 5' base. For the unnatural enantiomer, this similarly involves adenine N3 alkylation but with a reversed 5'→3' binding orientation. As a consequence of the diastereomeric relationship of the adducts and in spite of the reversed 5'→3' binding orientation, ent-(−)-N—BOC-DSA covers the same adjacent 5' base as (+)-N—BOC-DSA. Thus, both enantiomers occupy the same binding site surrounding the alkylated adenine.

Models of alkylation at the high affinity w794 DNA site by the natural enantiomer of the extended agent (+)-DSA-CDPI$_2$ and the unnatural enantiomer of the reversed agent ent-(−)-CDPI$_2$-DSA highlight the origin of the switch in the inherent enantiomeric alkylation selectivity with the reversed analogs. The natural enantiomer, (+)-DSA-CDPI$_2$, alkylates the 3' adenine and extends in the typical 3'→5' direction over the adjacent four 5' bases (5'-AATTA). The unnatural enantiomer of the reversed analog, ent-(−)-CDPI$_2$-DSA, also alkylates the 3' adenine albeit with the reversed orientation of the alkylation subunit but with the DNA binding subunits extending in the atypical 3'→5' direction over the same adjacent four 5' bases (5'-AATTA). Thus, the natural enantiomer of DSA-CDPI$_2$ and the unnatural enantiomer of the reversed analog CDPI$_2$-DSA bind and cover the exact same AT-rich 5 base-pair region surrounding the adenine N3 alkylation site.

The unnatural enantiomer of the typical agent alkylates adenine N3 and binds across a 5 base region in the 5'→3' direction in the minor groove which is opposite that of the typical natural enantiomers. Because of the diastereomeric nature of the adducts and analogous to ent-(−)-N—BOC-DSA, the binding site starts at the 5' site adjacent to the alkylation site and extends in the 5'→3' direction covering the adenine N3 alkylation site and the following three 3' bases (5'-A<u>A</u>TTT). Consequently, the 5 base-pair AT-rich binding site surrounding the alkylation site for ent-(−)-DSA-CDPI$_2$ is analogous to that of the natural enantiomer except that it extends in the reverse direction in the minor groove relative to the alkylated adenine and is offset by one base-pair. The natural enantiomer of the reversed analog, (+)-CDPI$_2$-DSA, covers the same 5 base-pair AT-rich region surrounding the alkylated adenine but with the reversed orientation of the alkylation subunit and with the DNA binding subunits extending in the atypical 5'→3 direction.

The natural enantiomer CDPI-DSA-CDPI (30) binds in the minor groove with the alkylation subunit extending in the 3'→5' direction with the binding subunits covering 2 base-pairs on both the 5' and 3' side of the alkylation site. The binding extends slightly farther to the 5' side (2.5 base-pairs) than the 3' side (2 base-pairs) and this accounts nicely for the stronger and slightly extended AT preference on the 5' side of the alkylation site. The unnatural enantiomer of 30 exhibits identical characteristics except that the alkylation subunit binds in the minor groove with the alkylation subunit extending in the reverse 5'→3' direction relative to the alkylation strand covering the same 5 base AT-rich site surrounding the central alkylated adenine. This unusual feature of the two enantiomers binding and alkylating the same 5 base-pair AT-rich sites is analogous to (+)- and ent-(−)-N—BOC-DSA except that the latter smaller agents only cover 2 base-pairs.

Sequence Preferences. Each of the classes of agents have been shown to exhibit an adenine N3 alkylation selectivity that contains a three-base AT sequence including and surrounding the alkylated adenine (FIG. 13). Although it is tempting to assign a special significance to the sequence preferences, the results are most consistent with a purely statistical preference. The most frequently alkylated sequence for each class is 5'-AAA and the extent of alkylation diminishes as the A content gets smaller. In contrast to 5'-AAA, the mixed sequences contain competitive alkylation sites on the complementary unlabeled strand which diminish the apparent alkylation efficiency on the labeled strand. It is likely that a majority of the apparent selectivity is simply a statistical preference exaggerated by competitive unlabeled strand alkylation rather than unique characteristics embodied in the individual sequences. The exception to this generalization is the unusually effective alkylation of 5'-TT<u>A</u> by (+)-DSA-CDPI$_2$ representative of the typical natural enantiomers including (+)-CC-1065 and (+)-duocarmycin SA and the under represented alkylation of 5'-AT<u>A</u> by the unnatural enantiomers of the reversed analogs including ent-(−)-CDPI$_2$-DSA. The significance of this is not yet known.

Rates and Efficiencies of DNA Alkylation. In the course of examining the reversed and sandwiched agents, substantial differences in the rates and efficiencies of DNA alkylation were observed. First and foremost, extraordinarily slow rates were observed for the reversed agents at sites that are alkylated rapidly by the typical agents and extraordinarily fast rates were observed by the sandwiched agents at new sites not previously observed. It is thus likely that the characteristics responsible for the effective alkylation are not uniquely imbedded in the DNA sites or associated with the alkylated adenine but with structural features of the agents and intimately related to the source of catalysis for the reaction.

Consequently, these differences were quantitated by establishing the relative rate constants ($\kappa_{rel}$, 5×10$^6$ M agent, 25° C.) for alkylation of the w836 high affinity alkylation sites within the six base A sequence (5'-AAAAAA) that both enantiomers of all three agent classes effectively alkylate. After just 1–5 min, the natural enantiomer of the typical extended agent, (+)-DSA-CDPI$_2$ (+E), and both enantiomers of the sandwiched analog 30, CDPI-DSA-CDPI (+and −S), exhibit extensive alkylation. In contrast, the unnatural enantiomer of the typical extended agent, ent-(−)-DSA-CDPI$_2$ (−E), requires 6 h to approach the same level of DNA alkylation and both enantiomers of the reversed analog, CDPI$_2$-DSA (+and −R), require 72 h to reach a detectable and diminished level of DNA alkylation. Although the reversed natural enantiomer was faster than the unnatural enantiomer, neither comes even close to the rates exhibited by (+)-DSA-CDPI$_2$ or (+)- and ent-(−)-CDPI-DSA-CDPI (30) and more closely approximate the rates of DNA alkylation observed with N—BOC-DSA (4) which lacks the DNA binding subunits altogether.

An Additional Structural Requirement for Catalysis of the DNA Alkylation Reaction and Source of Catalysis. The DNA alkylation rate of the extended as well as the sandwiched agents is exceptionally fast and typical of this class of agents while that of all reversed agents is exceptionally slow proceeding at rates similar to those of N—BOC-DSA (4). Although there are many potential explanations for this, it is not due to differences in the noncovalent binding affinity of the agent. In addition, the DNA alkylation selectivity of the reversed versus extended analogs simply reversed with these agents and no new sites were detected. Thus, it was the rates but not the sites that were altered.

Complementing these observations, the rapid rate of DNA alkylation by the sandwiched analogs was observed at a new set of alkylation sites independent of the absolute configuration of the agent indicating that the source of catalysis was not uniquely imbedded in the original DNA alkylation sites. Rather, the distinguishing feature between the extended or sandwiched analogs and the reversed analogs is the presence of the right-hand heteroaryl N$^2$ amide. Thus, a rigid extended N$^2$ amide substituent is required for rapid and effective alkylation of duplex DNA. With the sandwiched analogs, this effect is independent of the sites of DNA alkylation and the enantiomeric configuration of the alkylation subunit. We suggest that upon binding to DNA with the adoption of a helical bound conformation, the inherent twist of the alkylation subunit N$^2$ amide in the reversed analogs is not altered and, thus, not activated for nucleophilic addition. Consequently, they undergo DNA alkylation at rates comparable to those of the simple derivatives such as 4. The simple derivatives including 4 and the reversed agents 17–20 both require extended reaction times (2–7 days, 25–37° C.) for substantial or complete alkylation with 17–20 being only marginally faster and ultimately 10–100× more efficient. These small differences can be attributed to the more effective noncovalent minor groove binding properties of 17–20. The larger 10$^3$–10$^4$ rate differences between 1–3 and 17–20 may be attributed to the DNA binding-induced conformational change uniquely imposed on 1–3 and related agents. In the absence of the extended right-hand subunit, DNA minor groove binding no longer requires an induced twist in the $N^2$ amide linkage depriving the agent of this additional activation toward DNA alkylation.

Cytotoxic Activity. The in vitro cytotoxic activity of the agents is summarized in FIG. 14. Several important trends were observed which parallel the observations made in the DNA alkylation studies. Foremost, the natural enantiomers of the reversed analogs were 100–1000× less potent than the corresponding extended analogs while the two sandwiched analogs 30 and 31 were essentially equipotent with the typical agents. The reversed analogs proved essentially indistinguishable (17, 18, 23) or less than 10× more potent (19,20) than the simple derivatives, N—BOC-DSA (4) and N—Ac-DSA, that lack DNA binding subunits altogether. This is analogous to the observations made in the DNA alkylation studies where 17–20 and 23–24 were found to alkylate DNA with a rate and efficiency similar to those of 4 rather than 1–3. Consistent with the trends observed in the DNA alkylation studies, the unnatural enantiomers of the agents generally were approximately 10× less potent than the natural enantiomers. The exceptions to this generalization are DSA-CDPI$_2$, CDPI$_2$-DSA, and the sandwiched analogs where the two enantiomers proved nearly equipotent.

Like the natural enantiomers, the unnatural enantiomers of the reversed agents were also much less potent than the corresponding unnatural enantiomers of the extended analogs although the magnitude of the differences was somewhat smaller (20–100× versus 100–1000×). However, they proved to be even more comparable in potency to the unnatural enantiomers of N—BOC-DSA (4) and N—Ac-DSA lacking the attached DNA binding subunits. The nature of the terminal $N^2$ acyl substituent did not alter these observations in a substantial manner. The corresponding natural and unnatural enantiomers of 18 and 23 proved essentially indistinguishable while 24 was noticeably less potent. This latter effect could be anticipated given the remarkable stability of the alkylation subunits lacking a $N^2$ acyl substituent and the resulting less effective DNA alkylation. Thus, consistent with the trends observed in the rates and efficiencies of DNA alkylation and independent of the nature of the simple $N^2$ substituent, the reversed analogs proved comparable in cytotoxic potency to the simple derivatives 4 and N—Ac-DSA lacking the DNA binding subunits rather than 1–3 and the related extended analogs.

The potent cytotoxic activity of the sandwiched analogs is observed with a class of agents that exhibit a significantly different selectivity of DNA alkylation than preceding agents and one which is the same for both the natural and unnatural enantiomers. Since both enantiomers are essentially equipotent and exhibit the same DNA alkylation selectivity, this could permit the use of the more readily available racemic agents in the development of potential clinical candidates with confidence that both enantiomers contribute productively and equivalently to the expression of the resulting properties.

The cytotoxic activities of the more potent, extended derivatives plateau at 3–4 pM and closely follow established trends relating chemical stability and cytotoxic potency. Since the duocarmycin SA alkylation subunit is among the most stable examined to date, the cytotoxic activity of such analogs is among the most potent yet described.

The seco precursor agents, e.g. 13–16, 22, 28 and 29, exhibited cytotoxic activity that was not distinguishable from the corresponding cyclopropane containing agents 17–20, 23, 30 and 31, respectively, indicating that their spirocyclization to the biologically potent agents under the conditions of assay is not limiting.

Conclusions. A number of key features contribute to the sequence selective DNA alkylation by members of this class of agents. The reaction constitutes nucleophilic addition of the most sterically accessible of the two most nucleophilic sites in the minor groove (adenine N3 versus guanine N3). The clean regioselectivity for exclusive addition to the least substituted cyclopropane carbon represents the stereoelectronically-preferred site of attack which is further reinforced by the destabilizing torsional and steric interactions that would accompany addition to the more substituted carbon with ring expansion and is characteristic of $S_N2$ addition of a hindered nucleophile. Consistent with the noncovalent binding model, the length-dependent AT-rich alkylation selectivity is derived from the preferential noncovalent binding selectivity of the agents in the deeper, narrower AT-rich minor groove. The reverse and offset AT-rich alkylation selectivity of the enantiomers and the switch in the inherent enantiomeric alkylation selectivity of the reversed analogs establish that both enantiomers are subject to the same polynucleotide recognition features. Finally, a DNA binding-induced conformational change in the agent induces a twist in the linking $N^2$ amide resulting in loss of the alkylation subunit vinylogous amide stabilization catalyzing the DNA alkylation reaction. Since the binding-induced confoirmational change is greatest within the narrower, deeper AT-rich minor groove, this leads to selective catalysis within the preferred binding sites. An important ramification of the binding-induced substrate ground state destabilization is that it fuirther serves to stabilize the inherently reversible DNA alkylation reaction.

This alternative source of catalysis for the DNA alkylation reaction explains a number of observations. It is consistent with the lack of a substantial pH dependence on the rate of reaction and explains the growing number of instances where the rates of DNA alkylation were not found to follow the relative rates of acid-catalyzed reactivity. It explains the extraordinarily slow DNA alkylation rates of the reversed analogs and suggests that the small differences between the reversed analogs and simple derivatives such as 4 constitute those attributable to the enhanced minor groove binding. The remaining larger differences between the reversed analogs and the typical agents, and thus the bulk of the distinctions between 1–3 and 4–6, constitute the catalysis derived from the DNA binding-induced confortnational change in the agent. It is consistent with the well established view that the unusual stability of the agents is derived from the vinylogous amide conjugation and that its disruption should lead to significant increases in reactivity. Moreover, it offers new insights into the reversibility of the DNA alkylation reaction and suggests that both the rate of retroalkylation and the reaction equilibrium is shifted to favor adduct formation through a binding-induced destabilization of the substrate ground state. It explains the important effects of selected substituents that are located in the minor groove of the bound agents, e.g. duocarmycin SA C6-CO$_2$Me and C5'-OMe, and even offers a new insight into the origin of the distinctions between the enantiomers of the typical agents such as 1–3. This shape selective catalysis coincides within the preferred noncovalent binding sites. That the sequence selectivity is controlled by the noncovalent binding selectivity is defined by the fact that the identical selectivities are observed with agents not subject to this source of catalysis including the reversed analogs albeit with alkylation at much slower rates.

B. Shortened and Extended Analogs

DNA Alkylation Efficiency and Selectivity. The DNA alkylation properties of the agents were examined within five 145–155 base-pair segments of DNA. The five clones of phage M13mp10 contain SV40 nucleosomal DNA inserts: w794 (nucleotide no. 5238-138) and its complement w836 (nucleotide no. 5189-91), c988 (nucleotide no. 4359-4210) and its complement c820 (nucleotide no. 4196-4345), and c1346 (nucleotide no. 1632-1782). The alkylation site identification and the assessment of the relative selectivity among the available sites were obtained by thermally-induced strand cleavage of the singly 5' end-labeled duplex DNA after exposure to the agents. A statistical treatment of the alkylation sites proved more revealing than a conventional analysis that considers only the observed alkylation sites. This evaluation that includes the consideration of sites not alkylated helped define the composite consensus sequence and highlighted subtle features not apparent from a simple consideration only of the alkylated sites.

Simple Derivatives of the Alkylation Subunit. The consensus alkylation selectivity of both enantiomers of 40 and 41 alongside N—BOC-DSA (39) and (+)-duocarmycin SA is summarized in Table 3. First and foremost, the simple derivatives are much less efficient ($10^3$–$10^4\times$) and exhibit a different and less selective DNA alkylation selectivity than duocarmycin SA. Like 39, both enantiomers of 40 and 41 alkylate the same sites exhibiting an identical two base-pair AT-rich alkylation selectivity (5'-A<u>A</u>>5'-T<u>A</u>) although there are subtle differences in the relative efficiencies of alkylation at the individual sites. The apparent preference of 5'-A<u>A</u>>5'-T<u>A</u> is purely statistical and the complementary unlabeled strand for the mixed sequence contains an identical 5'-TA site whose competitive alkylation diminishes the apparent alkylation efficiency of the labeled strand. Importantly, significant distinctions in the alkylation selectivities of such simple derivatives (BOC=COCH$_3$=CO$_2$CH$_3$) were not seen: they are all much less selective than 1–3. The identical alkylation selectivity of both enantiomers of such simple derivatives is a natural consequence of the reversed binding orientations and the diastereomeric relationship of the adducts that result in the two enantiomers covering the exact same binding site surrounding the alkylated adenine. The factors controlling the alkylation selectivity are simply reaction at the sterically most accessible of the two most nucleophilic minor groove sites (adenine N3 versus guanine N3) and the depth of minor groove penetration available to the agent at the binding region surrounding the alkylation site. For simple derivatives including 39–41, this is possible only when the adjacent 5' base is A or T.

The distinctions between the agents lie in the efficiencies of DNA alkylation. The natural enantiomers of 40 and 41 alkylate DNA at $10^{-3}$ M and were approximately 10× more efficient than (+)-N—BOC-DSA. The similarities in 40 and 41 and the less effective DNA alkylation by N—BOC-DSA suggest that the differences simply may be due to the size of the substituent. The unnatural enantiomers of 40 and 41 were approximately 10× less effective at alkylating DNA while the relative distinctions between (+)- and ent-(−)-N—BOC-DSA were smaller. In addition to the much higher concentrations ($10^3$–$10^4\times$) required to detect alkylation with 39–41, it also requires much more vigorous reaction conditions (37° C., 24 h versus 4° C., 2–10 h). These data suggest that in the absence of the extended right-hand subunit, DNA minor groove binding does not induce a twist in the N$^2$ amide and deprives the agent of this activation toward DNA alkylation.

Modifications in the Trimethoxyindole Subunit: Role of the Methoxy Substituents. DNA alkylation by the natural enantiomers of 53–56 were compared with that of 1 in w794 DNA. All five agents exhibited identical DNA alkylation selectivities and the distinctions observed were in the rates and efficiencies. When the incubation was conducted at 25° C. for 24 h, 54 was found to be essentially indistinguishable from 1 itself, 55 and 56 (55>56) were 5–10× less efficient than 1, and 53 was 20× less efficient than 1 (Table 5). These trends in the efficiency of DNA alkylation were found to parallel the relative trends in cytotoxic potency. The relative rates of DNA alkylation for 1, 54, and 53 ($10^{-5}$ M, 25° C., 1–72 h) were also examined within w794 DNA at the single high affinity site of 5'-d(AATT<u>A</u>). (+)-Duocarmycin SA (1) and 54 were nearly indistinguishable with I exhibiting a slightly faster rate ($\kappa_{rel}$=1.3–2.3) and both were substantially faster than 53 ($\kappa_{rel}$=18–33).

Similar observations were made with the unnatural enantiomers (FIG. 15). Consistent with past observations, they all were found to alkylate DNA with a slower rate (ca. 50×)[7] and lower efficiency (ca. 10×) than the corresponding natural enantiomer. Detection of alkylation required both higher agent concentrations (10–50×) and longer reaction times (72 versus 24 h). The distinctions between enantiomeric pairs of agents diminished as the number of methoxy groups were reduced and were greatest when the C5 methoxy group was present.

Thus, the C7 and C6 methoxy groups, which lie on the outer face of the DNA-agent complex, individually contribute little (C6>C7) to the properties of duocarmycin SA. In contrast, the C5 methoxy group that is deeply imbedded in the minor groove contributes prominently to its properties. The agent containing a single C5 methoxy substituent proved essentially indistinguishable from duocarmycin SA indicating that it alone is sufficient for observation of the full potency of the natural product. This is consistent with a role in which the C5 methoxy group provides further noncovalent binding stabilization for the inherently reversible DNA alkylation reaction by virtue of its placement deep in the minor groove. More importantly, the C5 methoxy group of duocarmycin SA extends the rigid length of the DNA binding subunit. Its presence results in an increase in the inherent twist in the helical conformation of the DNA bound agent with the helical rise of the agent adjusted at the site of linking amide. This alters the vinylogous amide conjugation in the alkylation subunit and increases the inherent reactivity of the agent contributing to the catalysis of the DNA alkylation reaction. Removing the C5 methoxy substituent shortens the length of the right-hand subunit, decreases the inherent twist in the linking amide in the DNA bound conformation, and results in less effective activation of the agent for DNA alkylation.

Additional subtle features that were revealed include the unusual DNA alkylation efficiency of (+)-DSA-indole, (53). Although it proved to be 6–10× less effective than duocannycin SA, it is comparatively more effective than the indole derivative of CPI[20] or CBI.[7] Moreover, the relative DNA alkylation rates of the DSA-based agents substantially exceed those of the corresponding CPI-based agents despite their reduced reactivities. This is likely due to the presence of the C6 methyl ester which similarly extends the rigid length of the alkylation subunit. Consequently, even with a short suboptimal right-hand subunit, the presence of the C6 methyl ester insures more effective activation for DNA alkylation.

Extended Analogs: DSA-CDPI$_1$, DSA-CDPI$_2$, and DSA-indole$_2$. The examination of the agents 60–62 proved more important in our studies than anticipated.

Their side-by-side comparison with the reversed analogs detailed in the accompanying paper not only provided a definitive demonstration of the origin of the DNA alkylation selectivity, but also provided insights into the the source of catalysis. Under the conditions of the assay, 60–62 alkylated DNA at concentrations as low as $10^{-6}$–$10^{-7}$ M and did so with essentially the same efficiency. The consensus alkylation sequences for (+)- and ent-(−)-DSA-CDPI$_2$ are summarized in FIG. 16. Without exception, all alkylation sites proved to be adenine under the conditions of the assay. Each adenine alkylation site was flanked by at least two 5' A or T bases with a preference that follows the order of 5'-AA<u>A</u>>5'-TT<u>A</u>>5'-TA<u>A</u>≧5'-AT<u>A</u>. There was also a strong preference for the fourth and fifth 5' bases to be A or T, and this preference distinguished the high affinity versus low affinity alkylation sites. Consistent with expectations, (+)- and ent-(−)-DSA-CDPI$_2$ exhibited a 5 base-pair AT-rich DNA alkylation selectivity identical to those of (+)- and ent-(−)-CC-1065 and distinguishable from the shorter 3.5 base-pair AT-rich selectivity of duocarmycin SA. Similar observations were made with (+)-DSA-indole$_2$. The relative selectivity of alkylation among the available sites proved to be greater with (+)-DSA-CDPI$_2$ than (+)-DSA-CDPI$_1$. Characteristic of this enhanced selectivity, (+)-DSA-CDPI$_2$ failed to alkylate the minor w794 site (5'-CAA<u>A</u>G) while (+)-DSA-CDPI$_1$ prominently alkylates this minor site, requiring concentrations only 10xthat for alkylation at the major 5'-AATT<u>A</u> site.

The alkylation profiles of the unnatural enantiomers 60–62 are very distinct from those of the natural enantiomers. Without exception, all alkylation sites proved to be adenine under the conditions of the assay and nearly all of the 3' and 5' bases flanking the adenine N3 alkylation site proved to be A or T (FIG. 16). There proved to be a preference for the following three base-pair sequences: 5'-A<u>AA</u>>5'-A<u>A</u>T≧5'-T<u>AA</u>>5'-T<u>A</u>T. The high affinity alkylation sites, e.g. 5'-A<u>A</u>TTT, each proved consistent with 5' adenine alkylation, agent binding in the minor groove in the 5'→3' direction from the alkylation site covering 3.5 or 5 base-pairs across an AT-rich region. The unnatural enantiomer AT-rich alkylation selectivity relative to the adenine N3 alkylation site is reversed and offset from that observed with the natural enantiomers. Consistent with expectations, ent-)-)-DSA-CDPI$_2$ exhibited a 5 base-pair AT-rich alkylation selectivity identical to ent-(−)-CC-1065 readily distinguishable from the shorter 3.5 base-pair selectivity of ent-(−)-duocarmycin SA and related smaller agents (FIG. 16). The unnatural enantiomers also exhibited a slower rate and lower efficiency (10–100×) of DNA alkylation than the corresponding natural enantiomer.

Thus, the results show that the depth of minor groove penetration by the agent and steric accessibility to the alkylation site are likely important features contributing to the observed selectivity of DNA alkylation. For simple derivatives of the alkylation subunit, sufficient minor groove access to the reacting center is possible with a single 5' A or T base adjacent to the alkylation site. For the extended agents including 60–62, sufficient minor groove penetration may be possible only when two or more adjacent bases are A or T and this AT-rich selectivity nicely corresponds to the size of the agent (FIG. 16). Further contributing to this AT-rich alkylation selectivity of the longer agents is their preferential noncovalent binding within the narrower, deeper AT-rich groove.

Rate of DNA Alkylation: pH Dependence. The effects of pH on the DNA alkylation rate were studied by establishing the (+)-duocarmycin SA relative and first order rate constants ($\kappa_{obs}$) for alkylation of the single w794 high affinity alkylation site (5'-AATT<u>A</u>) at the pH of 6.0, 6.6, 7.1, 7.6, and 8.1 ($10^{-6}$ M, 25° C., 10 mM phosphate buffer, 0–3 h). Because this was conducted using w794 DNA additionally containing >7000 base-pairs and multiple binding sites within the unlabeled portion of the DNA, the comparisons were conducted at concentrations that provide saturated binding and restrict the kinetic analysis to the pseudo-first order rate constant for alkylation. Although the rate of DNA alkylation was found to increase with decreasing pH, the rate change was small (<2× over 2 pH units) and inconsistent with a first order dependence on acid concentration. Moreover, between pH 7 and 8 which may be considered the most relevant range, the rate dependence on pH essentially disappeared. Just as significant, comparison of the psuedo-first order rate constant for DNA alkylation at this site, $\kappa=1.69\times10^{-4}$ s$^{-1}$ (pH 7.1), with the calculated pseudo-first order rate constant for acid-catalyzed solvolysis ($\kappa=1.08\times10^{-10}$ s$^{-1}$) at pH 7 revealed that the bulk of catalysis for the DNA alkylation reaction cannot be accounted for by this source. Perhaps the magnitude of this difference is best recognized by simply stating that at pH 7, the $t_{1/2}$ for solvolysis is 202 years (7.4×10$^4$ days) while that of DNA alkylation is 1.1 h. The relative lack of dependence on the acid concentration (pH) especially in the most relevant pH range of 7–8 in conjunction with the observations made in the accompanying paper has led us to propose an alternative source of reaction catalysis.

Catalysis: DNA Binding Induced Conformational Change in the Agent Results in Activation. Studies of the extent and structural origin of the rate acceleration for the DNA alkylation reaction have led to the proposal that catalysis for the DNA alkylation reaction is derived from a DNA binding-induced conformational change in the agent that disrupts the vinylogous amide stabilization of the alkylation subunit and activates the agent for nucleophilic addition. This conformational change results from adoption of a helical bound conformation that follows the curvature and pitch of the DNA minor groove. The helical rise in the bound conformation of the rigid agents is adjusted by twisting the linking N$^2$ amide which is the only available flexible site. The twisting of the $_{\chi1}$ dihedral angle of the linking amide ($_{\chi2}$~0°) diminishes the N$^2$ lone pair conjugation with the cyclohexadienone, disrupts the vinylogous amide stabilization of the alkylation subunit, and increases its inherent reactivity. An alternative possibility involves a twisting of the $_{102\ 2}$ dihedral angle diminishing the amide conjugation and increasing the N$^2$ vinylogous amide conjugation. This would increase the basicity of the C4 carbonyl leading to more effective protonation. There is evidence to suggest this can result in both increased or decreased reactivity depending on the extent of the vinylogous amide conjugation and all studies concur that even subtle perturbations can result in large changes in reactivity.

N-Acylation of the nitrogen (e.g. N—CO$_2$Me-CNA versus CNA) reduces the vinylogous amide conjugation, lengthens bond c, and results in a substantial increase in inherent reactivity. Typically accompanying this reduction in the vinylogous amide conjugation is an increase in the length of the reacting cyclopropane bond. One interpretation of this is that both the cyclopropane conjugation and its inherent reactivity increase as the cross-conjugated vinylogous amide A-overlap is diminished. Additional features including the alignment of the cyclopropane may further contribute to the cyclopropane conjugation (CBQ aligned but CBI offset by 20°) and the cyclopropane bond lengths and reactivity of CBQ versus CBI also reflect this effect on the relative degree of conjugation. More importantly, within the series of N-acyl derivatives, both the length of bond c diagnostic of the extent of vinylogous amide conjugation and the reactivity smoothly increase as the $\chi_1$ dihedral angle increases. The reactivity of N—CO$_2$Me-CNA (or N—BOC-CNA) is extraordinary exhibiting a t$_{1/2}$ of only 2.1 h at pH 7 in the absence of deliberate added acid catalysis. It is 10$^3$–10$^4$× more reactive than N—BOC-DSA and represents an agent that benefits from little, if any, vinylogous amide stabilization. This level of reactivity is greater than that required. In fact, it is the reactivity and $\chi_1$ dihedral angle of N—BOC-CBQ that may more closely approximate that required for the DNA alkylation catalysis provided by the DNA binding induced conformational change in 1–3. Its inherent reactivity at pH 7 coupled with the rate enhancements afforded a bound species that might provide a further 10$^2$× rate acceleration approximates the rates observed with the DNA alkylation reaction.

This has important ramifications on the source of the DNA alkylation selectivity. The inherent twist and helical rise of the bound conformation of the agent is greatest within the narrower, deeper AT-rich minor groove. This leads to preferential activation of the agent for DNA alkylation within extended AT-rich minor groove sites and complements their preferential AT-rich noncovalent binding selectivity, Thus, both shape-selective recognition (preferential AT-rich noncovalent binding) and shape-dependent catalysis (extended AT-rich>GC-rich activation by twist in N$^2$ amide) combine to restrict S$_N$2 alkylation to accessible adenine N3 nucleophilic sites within the preferred binding sites. Importantly, this ground state destabilization of the substrate only activates the agent (e.g., arms the warhead) for a rate determining S$_N$2 nucleophilic addition and requires the subsequent proper positioning and accessibility to an adenine N3 site. Although a subtle point, this accounts nicely for the identical alkylation selectivities of CC-1065 (3) and 63–67 which lack both the C4 carbonyl and the activated cyclopropane but which alkylate DNA at substantially slower rates. Thus, the alkylation selectivity is controlled by the identical AT-rich noncovalent binding selectivity of the agents, but 63–67 react much slower in part because they lack the capabilities for activation by the DNA binding-induced conformation change.

This source of catalysis requires an extended and rigid N$^2$ amide substituent and the absence of such a substituent with 39–41 accounts nicely for their relatively slow and ineffective DNA alkylation. The noncovalent binding derived from the attached right-hand subunits accounts for a much smaller part of the difference in the rates of DNA alkylation between 39–41 and 1. More importantly, this source of catalysis would lead to distinctions, not similarities, in the DNA alkylation selectivities of 39–41 versus 1.

Reaction Regioselectivity and Stereochemistry: Subtle Features Contributing to the DNA Alkylation Regioselectivity. Studies of the inherent solvolysis regioselectivity and stereochemistry in conjunction with the structural studies have also provided important insights into the mechanism of nucleophilic addition and subtle features contributing to the regioselectivity of the DNA alkylation reaction. A study of the acid-catalyzed nucleophilic additions to N—BOC-DSA (39) established that solvolysis preferentially occurs with cleavage of the C7b-C8 bond with addition of a nucleophile to the least substituted C8 cyclopropane carbon versus cleavage of the C7b-C8a bond with ring expansion and addition to C8a. The latter cleavage would place a developing partial positive charge on a preferred secondary versus primary center and this preference was overridden by the inherent stereoelectronic control of the reaction regioselectivity. Preparative acid-catalyzed addition of CH$_3$OH to N—BOC-DSA (0.12 equiv CF$_3$SO$_3$H, 0.01 M in CH$_3$OH, 0 or 25° C., 1–3 h, 88–93%) cleanly provided two products 66 and 67 in a 6.5—4:1 ratio with the greater selectivity observed at 0 versus 25° C. (Scheme 5). Similarly, solvolysis of 39 (0.24 equiv CF$_3$SO$_3$H, 0.01 M in 20% H20—THF, 25° C., 48 h, 95–96%) provided a 6:1 ratio of 35 to 68. The mechanistic course of the reaction was established by subjecting both racemic and natural (+)-39 to the acid-catalyzed methanolysis or solvolysis. Resolution on a Diacel Chiral-Cel AD HPLC column separated both enantiomers of the two reaction products and those derived from optically active (+)-39 were found to consist of a single enantiomer. Although the generation of a single enantiomer of 66 would be consistent with either a S$_N$1 or S$_N$2 ring opening reaction, the generation of a single enantiomer of 67 establishes that the ring expansion proceeds with clean inversion of the reaction center stereochemistry in a S$_N$2 reaction. This is consistent with kinetic studies of the acid-catalyzed nucleophilic addition where the rate of reaction exhibits a first order dependence on both the acid concentration (pH) as well as the nucleophile indicative of a mechanism involving rapid and reversible C4 carbonyl protonation followed by a slow, rate determining S$_N$2 nucleophilic attack on the activated cyclopropane.

Important insights into the solvolysis regioselectivity may be derived from the structural studies. The distinguishing feature controlling the regioselectivity appears to be the relative stereoelectronic alignment of the two cyclopropane bonds available for cleavage. Within a class of agents whose cyclopropane alignment with the π-system would be expected to be similar due to structural constraints, the regioselectivity nicely follows the reactivity with the more stable agents providing the more selective reaction: e.g. N—BOC-DSA (6–4:1)>CPI (4:1)>N—BOC-DA (3:2). However, this fails to hold true when comparing between classes of agents: e.g. N—BOC-CBI ($\geq$20:1) versus N—BOC-DSA (6–4:1) versus N—BOC-CNA ($\leq$1:20). Thus, additional important factors contribute to this reaction regioselectivity. In the comparisons that can be made from the available X-ray structures, the selectivity more accurately reflects the relative degree of stereoelectronic alignment of the two available cyclopropane bonds and this alone accounts for the reaction regioselectivity. This is illustrated beautifully with the observation of the clean, smooth, and complete reversal of the reaction regioselectively as one progress through the series N—BOC-CBI ($\geq$20:1), N—BOC-CBQ (3:2), and N—BOC-CNA ($\leq$1:20).

The observation of exclusive adenine N3 addition to the C8 cyclopropane carbon in the DNA alkylation studies of 1 and related agents is not consistent with expectations that the inherent acid-catalyzed nucleophilic addition regioselectivity controls the DNA alkylation regioselectivity. This exclusive DNA alkylation regioselectivity was not only observed in our studies with 1 or 2 and their enantiomers but is general with all agents examined to date that undergo solvolysis with a mixed regioselectivity including the CPI-based agents and CC-1065 (4:1 regioselectivity) and the CBQ-based agents (3:2 regioselectivity). Examination of each of these agents has led only to detection of adducts derived from adenine N3 addition to the least substituted cyclopropane carbon. Moreover, each of these studies quantitated the adduct formation and, in the case of duocarnycin A (86–92%), duocarmycin SA (95–100%) CC-1065 (>85%), and the CBQ-based agents (>75%), established that the regioselectivity of the DNA alkylation reaction is greater than that of solvolysis. Although several explanations may be advanced for these observations, the three most prominent are preferential adoption of binding orientations that favor normal adenine N3 addition (proximity effects), the adoption of DNA bound conformations that impose full stereoelectronic control on the reaction, and the significant destabilizing torsional strain and steric interactions that accompany the abnormal addition. The data reported herein show that the latter subtle effect of preferential $S_N2$ addition of a large nucleophile to the least substituted carbon is likely most substantial. Consequently, the clean regioselectivity of the characteristic adenine N3 alkylation reaction benefits not only from stereoelectronic control but additional important subtle effects characteristic of the $S_N2$ addition of a large nucleophile that further enhance the normally observed regioselectivity.

Reversibility. The cyclopropane ring of the duocarmycins is very easily introduced through Ar-3' spirocyclization. This occurs so readily that the precursor agents will often close upon formation or upon exposure to chromatography supports (e.g., $SiO_2$). Although the reactions are usually conducted with strong base (NaH, DBU, $Et_3N$), the most stable of the agents including 35 may be prepared by simple exposure to even aqueous 2–5% $NaHCO_3$. The present studies show that the adoption of the DNA bound and alkylated conformation no longer facilitates Ar-3' spirocyclization with reversal of the DNA alkylation reaction and that this further contributes to the unusual stability of the DNA adducts. Not only does this ground state destabilization of the substrate account for the rate acceleration for formation of adduct by lowering the apparent activation energy but it contributes to a shift in the equilibrium to favor adduct formation since the product does not contain the vinylogous amide and is not similarly destabilized by adopting a helical conformnation. This subtle feature is likely more important to the expression of the biological properties than even the role in catalysis.

DNA Alkylation Studies: Selectivity and Efficiency. Eppendorf tubes containing singly $^{32}P$ 5'-end-labeled double-stranded DNA (9 µL) in TE buffer (10 mM Tris, 1 mM EDTA, pH 7.5) were treated with the agents in DMSO (1 µL, at the specified concentrations). The solutions were mixed by vortexing and brief centrifugation and subsequently incubated at 4° C., 25° C. or 37° C. for 24–72 h. The covalently modified DNA was separated from unbound agent by EtOH precipitation of the DNA. The EtOH precipitations were carried out by adding t-RNA as a carrier (1 µL, 10 µg/µL), 3 M NaOAc (0.1 volume) and –20° C. EtOH (2.5 volumes). The solutions were mixed and chilled at –78° C. in a REVCO freezer for 1 h or longer. The DNA was reduced to a pellet by centrifugation at 4° C. for 15 min and washed with –20 ° C. 70% EtOH (in TE containing 0.2 M NaCl). The pellets were dried in a Savant Speed Vac concentrator and resuspended in TE buffer (10 µL). The solutions of alkylated DNA were warmed at 100° C. for 30 min to induce cleavage at the adenine N3 alkylation sites. After brief centrifugation, formamide dye solution (5 µL) was added. Prior to electrophoresis, the samples were denatured by warming at 100° C. for 5 min, placed in an ice bath, centrifuged briefly, and the supernatant (2.8 µL) was loaded onto a gel. Sanger dideoxynucleotide sequencing reactions were run as standards adjacent to the agent treated DNA reaction samples. Polyacrylamide gel electrophoresis (PAGE) was run on an 8% sequencing gel under denaturing conditions (19:1 acrylamide: N,N-methylenebisacrylamide, 8 M urea) in TBE buffer (100 mM Tris, 100 mM boric acid, 0.2 mM $Na_2EDTA$). PAGE was pre-run for 30 min with formamide dye solution prior to loading the samples. Autoradiography of dried gels was carried out at –78° C. using Kodak X-Omat AR film and a Picker Spectra™ intensifying screen.

Relative Rates of DNA Alkylation for (+)-1, 53, and 54. Following the procedure detailed above, Eppendorf tubes containing 5' end-labeled w794 DNA (9 µL) in TE buffer (pH 7.5) were treated with (+)-duocarmnycin SA, 53, or 54 (1 µL, $10^{-5}$ M in DMSO). At these concentrations ($10^{-4}$–$10^{-6}$ M), the rate of DNA alkylation was independent of agent concentration indicating saturated binding. The solutions were mixed and incubated at 25° C. for 1, 3, 6, 12, 24, 48, and 72 h, respectively. Subsequent isolation of the alkylated DNA by EtOH precipitation, resuspension in TE buffer (10 µL, pH 7.5), thermolysis (30 min, 100° C.), concurrent PAGE, and autoradiography were conducted as detailed above. The relative rate for the alkylation at the 5'-AATT$\underline{A}$ site was derived from the slopes of the plots of percent integrated optical density (IOD) of the high affinity alkylation site cleavage bands versus time.

Relative Rates of DNA Alkylation for (+)-1 at pH 6–8. Eppendorf tubes containing 5' end-labeled w794 DNA (9 µL) in phosphate buffer (10 mM) at pH 6.0, 6.6, 7.1, 7.6, and 8.1 were prepared. The solutions at each pH were treated with (+)-duocarmycin SA (1µL, $10^{-6}$ M in DMSO), mixed and incubated at 25° C. for 0.5, 1.0, 1.5, 2.0 and 3.0 h. At this concentration ($10^{-4}$–$10^{-6}$ M), the rate of DNA alkylation was independent of agent concentration indicating saturated binding. The reactions were stopped at each time interval by EtOH precipitation of the DNA. The alkylated DNA was resuspended in TE buffer (10 µL, pH 7.5) and heated at 100° C. for 30 min follwed by PAGE and autoradiography as detailed above.

Conclusions. Of the naturally occurring agents, duocarmycin SA is chemically the most stable and biologically the most potent. It exhibits the greatest inherent reaction regioselectivity and participates most effectively in the characteristic DNA alkylation reaction. The comparison of six X-rays structures suggest that the relative degree of stereoelectronic alignment of the two available cyclopropane bonds alone may account for the solvolysis regioselectivity. The exclusive DNA alkylation regioselectivity of the adenine N3 addition reaction exceeds that of the typical acid-catalyzed reactions for all agents examined to date. Several explanations may account for the observations including the adoption of binding orientations that favor the normal addition, the adoption of DNA bound conformations that impose complete stereoelectronic control on the reaction, and the destabilizing torsional strain and steric interactions that accompany the abnormal addition. The latter effects are most significant and simply represent the expected preferential $S_N2$ addition of a large, hindered nucleophile to the least substituted 2° versus 3° carbon of the activated cyclopropane.

The DNA alkylation selectivity of both enantiomers of a series of analogs of 1 were examined and proved consistent with prior studies. Both enantiomers of simple derivatives of the alkylation subunit (39–41) behave comparably and alkylate the same sites in DNA (5'-A$\underline{A}$>5'-T$\underline{A}$). This unusual behavior of the enantiomeric agents is a natural consequence of the reversed binding orientations and the diastereomeric relationship of the adducts that result in the two enantiomers covering the exact same binding site surrounding the alkylated adenine. The advanced analogs of 1–3 exhibited a different and larger 3.5 or 5 base-pair AT-rich adenine N3 alkylation selectivity that corresponds nicely to the length or size of the agent. For the natural enantiomers, the alkylation sites correspond to 3' adenine N3 alkylation with agent binding in the 3'→5' direction across a 3.5 or 5 base-pair AT-rich sequence, e.g 5'-AAAA$\underline{A}$. For the unnatural enantiomers, the alkylation sites correspond to 5' adenine N3 alkylation with agent binding in the reverse 5'→3' direction across a 3.5 or 5 base-pair AT-rich sequence that starts with the 5' base that precedes the alkylated adenine and extends over the alkylation site to the adjacent 3' side, e.g. 5'-A AAAA.

A study of the pH dependence of the rate of DNA alkylation revealed little effect in the pH range of 7–8 and only a modest effect below pH 7. This proved consistent with recent observations that the rate of DNA alkylation does not necessarily follow the relative rates of acid-catalyzed nucleophilic addition. As a consequence of this and consistent with the emerging model of the origin of the DNA alkylation selectivity, an alternative mechanism of activating the agent for DNA alkylation was introduced based on a DNA binding-induced conformational change in the agent which twists the linking $N^2$ amide and disrupts the vinylogous amide stabilization of the alkylation subunit. Further support of this mechanism of activation is provided in the accompanying article. An important consequence of this source of activation is that it is expected to be greatest within the narrower, deeper AT-rich minor groove further complementing the noncovalent minor groove binding selectivity of the agents. Thus, the shape-selective binding selectivity and shape-dependent catalysis combine to restrict $S_N2$ alkylation to accessible adenine N3 nucleophilic sites within the preferred 3.5–5 base-pair AT-rich binding sites.

The study of analogs containing modifications in the trimethoxyindole subunit revealed that the C5 methoxy substituent is necessary and sufficient for observation of the full effectiveness of the natural product while the C6 and C7 (C6>C7) methoxy substituents contribute little to its properties. In addition to its contribution to the noncovalent binding stabilization derived from its imbedded minor groove location, its simple presence increases the rigid length of the right-hand subunit increasing the inherent twist in the DNA bound helical conformation. This more effectively disrupts the vinylogous amide stabilization in the alkylation subunit and fuirther increases the inherent reactivity of the DNA bound agent. A similar role is proposed for the C6 methyl ester which extends the rigid length of the left-hand alkylation subunit.

The agents exhibited cytotoxic potencies consistent with the trends observed in the relative DNA alkylation efficiencies and each of the analog classes was found to follow a well-established relationship between chemical stability and cytotoxic potency. Since the duocarmycin SA alkylation subunit is the most stable of the naturally occurring alkylation subunits, its derivative analogs are the most potent disclosed to date. These studies are summarized in the accompanying article.

C. Analogs Containing a Modified Heterocycle

Chemical Solvolysis: Reactivity. Both the study of the rate of acid-catalyzed solvolysis and the regioselectivity of cyclopropyl ring opening have proven to be key to understanding of the structural features that dictate the properties of the duocarmycin and CC-1065 alkylation subunits. Comparison of the rate of solvolysis allows for the identification of the functional features that contribute to the stabilization or activation of the cyclopropane while studies regarding the regioselectivity of the acid-catalyzed ring opening have proven key to understanding the mechanism of the DNA alkylation reaction. To date, the preferred nucleophilic addition sites appear to be dictated by the relative stereoelectronic alignment of the scissile cyclopropyl bonds with the cyclohexadienone π-system but may be influenced by the relative reactivity. Moreover, both $S_N2$ and $S_N1$ mechanisms have been advanced to account for the generation of the abnormal ring expansion solvolysis products. In instances of mixed reaction regioselectivity, the clean generation of single DNA alkylation products derived from adenine N3 addition exclusively to the least substituted cyclopropane carbon indicates that additional subtle features inherent in the reaction contribute to its regioselectivity.

The solvolysis reactivities of N—BOC-CNA (78) and CNA (79) were followed spectrophotometrically by UV at both pH 3 (50% $CH_3OH$-buffer, buffer=4:1:20 v/v/v 0.1 M citric acid, 0.2 M $Na_2HPO_4$, $H_2O$) and pH 7 (50% $CH_3OH$—$H_2O$). The react of both 78 ($t_{1/2}$=1.7 min at pH 3) and 79 ($t_{1/2}$=37 min at pH 3) proved remarkable. CNA (79) was considerably more stable than N—BOC-CNA (78). Both were sufficiently reactive to undergo rapid solvolysis even at pH 7. Comparison of the solvolytic reactivity of N—BOC-CNA with representative prior analogs reveal a reactivity that is between that of N—BOC-CBQ and the exceptionally reactive N—BOC-CI. Particularly informative are comparisons of the benzo series of agents that differ only in the C-ring size (i.e., 76–79). Solvolysis reactivity smoothly increases through the series CBI<CBQ<CNA with both the N—BOC derivatives and the free NH derivatives. The reactivity of both N—BOC-CNA and CNA proved to be 4750 and 1500× more reactive than the corresponding CBI derivatives. Moreover, N—BOC-CNA exhibited a first-order rate constant for the solvolysis at pH 7 which is of the same order of magnitude as the characteristically rapid DNA alkylation reactions of 1–3 without deliberate added catalysis. The agents containing the free NH, and thus the greatest degree of vinylogous amide conjugation, were 10–40× more stable to solvolysis than the corresponding N—BOC derivatives.

Chemical Solvolysis: Regioselectivity and Mechanism. Treatment of N13 BOC-CNA (78) with 0.12 equiv of $CF_3SO_3H$ in a mixture of $H_2O$ and THF resulted in clean solvolysis (>96%) to provide a single product (FIG. 17). No N—BOC deprotection or olefin formation was observed. Comparison of this single product to 101 that would result from $H_2O$ attack at the less substituted cyclopropyl carbon indicated that ring expansion had occurred exclusively to afford 99. None of the typical seven-membered ring solvolysis product 101 could be detected in the crude reaction mixture by $^1H$ NMR or HPLC. Treatment of 78 with $CH_3OH$ under similar conditions gave an analogous result, providing excellent conversion exclusively to the abnormal ring expansion product 100. Although minor amounts of the ring expansion solvolysis products have been observed with related systems, the solvolysis of N—BOC-CNA represents the first observation of either predominant or exclusive ring expansion derived from cleavage of the internal cyclopropane bond. Similarly, treatment of 78 with 1.5 equiv of HCl in THF (−78° C., 15 min) cleanly provided 102 (>20:1, 99%) and not 87. This observation is especially significant. In some, but not all, of the prior instances of mixed solvolysis regioselectivity, the addition of HCl still cleanly provided the typical addition product derived from attack at the least substituted carbon rather than the ring expansion addition observed with the generation of 102. The clean addition of HCl to 78 to provide the ring expansion product 102 illustrates that the stereoelectronic control of the addition directs even the larger nucleophiles to the more hindered cyclopropyl carbon.

In an effort that established the mechanistic course of the reaction, both racemic and optically active (+)-78 were subjected to acid-catalyzed solvolysis (0.12 equiv of $CF_3SO_3H$, $H_2O$—THF, 25° C., 5 min) to provide 99. Resolution on a Diacel Chiracel OG analytical HPLC column separated both enantiomers of the reaction product. The product derived from optically active (+)-78 provided one enantiomer of the ring expanded product. The generation of a single enantiomer of 99 establishes that the cleavage of the internal cyclopropane bond does not proceed with generation of a free carbocation ($S_N1$) but instead occurs with clean inversion of the reaction center stereochemistry in an $S_N2$ ring opening reaction. These results are in agreement with the similarly unambiguous results of solvolysis studies of N—BOC-CBQ, N—BOC-DSA, and N—BOC-DA which also afford a single enantiomer of the minor ring expansion products but contrasts the studies with a CPI-derivative where racemization is reported to occur. This growing set of observations and especially that of the exceptionally reactive N—BOC-CNA detailed herein suggest the latter CPI studies should be reexamined employing a more definitive basis for establishing the optical purity of the ring expansion solvolysis product.

X-ray Structural Correlations with Solvolysis Regioselectivity. The single-crystal X-ray structure determination of N—$CO_2$Me-CNA (97) and CNA (79) was conducted in expectations of providing structural insights into its reversed solvolysis regioselectivity and extraordinary reactivity. To insure the comparisons were accurately made between the appropriately acylated and nonacylated derivatives, we have also extended the efforts to secure a total of eight X-ray crystal structures including both a simple N-acyl and the free NH derivative of CNA, CBQ, and CBI, as well as two seco precursors.

Comparison of the X-ray structures allows for a confirmation of the conclusions that have been drawn between the relative stereoelectronic alignment of the reacting cyclopropane bonds and solvolysis regioselectivity. The newly obtained X-ray structure for N—$CO_2$Me-CBI containing the five-membered C-ring, like that of CBI itself, reveals that the bent orbital of the cyclopropane bond extending to the least substituted carbon is nearly perpendicular to the plane of the cyclohexadienone and consequently overlaps well with developing π-system of the phenol solvolysis product. In contrast, the cyclopropane bond extending to the more substituted carbon is less effectively aligned and nearly orthogonal to the π-system. Reflecting this relative alignment, the cleaved C8b-C9 bond is the longest (1.544 versus 1.521 Å) and weakest of these two bonds. Thus, the cyclopropane cleavage occurs under stereoelectronic control with preferential addition of the nucleophile at the least substituted carbon (>20:1). This stereoelectronic control overrides any intrinsic electronic preference for ring expansion ring opening with partial positive charge development on the more substituted cyclopropane carbon but may also benefit from the characteristic preference for $S_N2$ nucleophilic attack to occur at the least substituted carbon.

In contrast, the previously obtained X-ray structure for N—BOC-CBQ (77) containing the 6-membered C-ring revealed that the cyclopropane is ideally conjugated and aligned with the π-system and the two potential cyclopropane cleavage bonds are perfectly bisected by the cyclohexadienone π-system. Such a bond orientation is consistent with the loss of solvolytic regioselectivity for N—BOC-CBQ which shows only a slight preference for nucleophilic addition at the less substituted cyclopropane carbon (3:2). Given an inherent preference for partial positive charge delocalization onto a secondary versus primary center, one might have anticipated preferential cleavage of the C9b-C10a bond. However, the bond extending to the less substituted cyclopropyl carbon is weaker as judged by its longer bond length (1.543 Å versus 1.528 Å) suggesting that any inherent preference for cleavage of the C9b-C10a bond is offset by this lower bond strength of the C9b-C10 bond. In addition, $S_N2$ nucleophilic attack at the more substituted tertiary center is sterically disfavored. Given that the ring expansion solvolysis occurs with clean inversion of stereochemistry, the developing torsional strain that accompanies nucleophilic addition with ring expansion may be especially significant and also contributing to the small regioselectivity preference.

Inspection of the X-ray crystal structure of N—$CO_2$Me-CNA reveals that the cyclopropane possesses alignment features of both N—$CO_2$Me-CBI and N—BOC-CBQ. Like N—$CO_2$Me-CBI, the cyclopropane is nonideally conjugated with the π-system but rises above rather than dips below the plane of the cyclohexadienone such that now the bond to the more substituted cyclopropane carbon enjoys the better stereoelectronic alignment. Thus, the smooth reversal of solvolysis regioselectivity with N—BOC-CNA may be attributed to the relative stereoelectronic alignment of the breaking C10b-C11a bond combined with any intrinsic electronic stabilization inherent in its greater substitution. Notably, this combination of stereoelectronic and electronic features is sufficient to overcome the destabilizing steric interactions that must accompany $S_N2$ addition at the more substituted center. Diagnostic of the regioselectivity of nucleophilic addition, the cleaved C10b-C11a bond is longer (1.565 Å versus 1.525 Å) and weaker than the C10b-C11 bond extending to the less substituted cyclopropane carbon. Like the geometric alignment of N—BOC-CBQ but unlike N—BOC-CBI, N—$CO_2$Me-CNA possesses a near perfect geometric orientation with respect to the plane bisecting the cyclohexadienone, deviating little from a perfect backside alignment.

Thus, consistent with comparisons that can be made from all such structural studies to date, the solvolysis reaction regioselectivity accurately reflects the relative stereoelectronic alignment of the two available cyclopropane bonds. This is beautifuilly illustrated with the clean, smooth, and complete reversal of the reaction regioselectivity as one progresses through the series N—BOC-CBI (>20:1), N—BOC-CBQ (3:2), and N—BOC-CNA (<1:20).

X-ray Structural Correlations with Solvolysis Reactivity. The solvolysis reactivity increases that occur in the series CNA>CBQ>CBI are the consequence of a previously unappreciated structural feature of the CC-1065 and duocarmycin alkylation subunits. Although the alkylation subunit vinylogous amide has been recognized as a structural feature contributing to its unusual stability, the extent of this stabilization has not been established nor has the structural, chemical, and biological consequences of its presence or disruption been defined. We recently highlighted that one of the most prominent structural features of the alkylation subunits that is directly observable in their X-ray structures is the alternating shortened and lengthened bonds within the vinylogous amide with the most diagnostic feature being the shortened C—N bond length. This provides the opportunity to establish by X-ray the relative extent of the vinylogous amide conjugation that accompanies structural modifications within the alkylation subunit and, ultimately, the ability to correlate this with the properties and chemical reactivity of the agents. Such comparisons within the CBI, CBQ, and CNA series proved especially revealing.

The direct comparisons of the full set of X-ray structures in the series provide a superb assessment of the extent of vinylogous amide conjugation and ultimately, the relative reactivity of the agents. First, N-acylation (e.g., N—$CO_2$Me-CBI versus CBI) reduces the vinylogous amide conjugation, lengthens bond c, and results in a substantial increase in reactivity. This is observed with each of the three sets of agents. Typical C—N bond lengths for a fully conjugated vinylogous amide are 1.312–1.337 Å. Thus, that of CBI (bond c, 1.337 Å) is diagnostic of a fully engaged vinylogous amide while that of N—CO$_2$Me-CBI (1.390 Å) is substantially diminished. Accompanying this reduction in the vinylogous amide conjugation that results from N-acylation is an increase in length of the reacting cyclopropane bonds and a readjustment of the cyclopropane alignment to a more idealized conjugation with the cyclohexadienone π-system. This illustrates that both the cyclopropane conjugation and its inherent reactivity increase as the cross-conjugated vinylogous amide n-overlap is diminished. One of the more important conclusions that can be drawn from these correlations is that the pronounced solvolysis stability of the free NH derivatives is due to this cross-conjugated and fully engaged vinylogous amide. Despite their increased basicity which would facilitate C-4 carbonyl protonation, they are much less reactive than the corresponding N-acyl derivatives toward acid-catalyzed nucleophilic addition reactions.

More importantly, these same trends are observed within the N-acyl series. As one moves across the series of N—CO$_2$Me-CBI, N—BOC-CBQ, and N—CO$_2$Me-CNA, the length of bond c increases (1.390, 1.415, and 1.428 Å) diagnostic of the loss of the cross-conjugated vinylogous amide. Correspondingly, the length, conjugation, and reactivity of the scissile cyclopropane bonds increase tracking with the relative reactivity of the agents. Accompanying these changes and responsible for this loss of vinylogous amide conjugation is an increase in the $\chi_1$ dihedral angle. Notably, the $\chi_1$ dihedral angle of N—CO$_2$Me-CNA is so large that the acyl group is nearly perpendicular to the plane of the cyclohexadienone π-system and the agent benefits from little, if any, vinylogous amide conjugation. This is reflected in its bond c length of 1.428 Å. Throughout this series, the $\chi_2$ dihedral angle is maintained at ca. 0° illustrating the preferential maintenance of the N carbamate conjugation versus that of the vinylogous amide. However, N—BOC-CBQ exhibits a slightly larger $\chi_2$ dihedral angle suggesting some carbamate distortion in efforts to maintain the vinylogous amide conjugation. These observations have important implications on the source of catalysis for the DNA alkylation reaction which is discussed in the following section.

An additional and more subtle structural feature that contributes to reactivity is seen in the structural comparisons of the NH derivatives. This series does not exhibit a completely smooth correlation between the $\chi_1$ torsion angle, the length of bond c, and reactivity. CBI boasts a torsion angle of 15.70 but is significantly less reactive than CBQ which has a smaller torsion angle of 6.9°. In the case of the NH derivatives, the X-ray $\chi_1$ torsional angles reveal nothing about the pyramidalization of the nitrogen and the resulting orientation of its lone pair. Therefore, it is difficult to assess the relative extent of n-overlap simply by measuring the $\chi_1$ angle. However, the identical C—N bond lengths for CBI and CBQ suggest that both benefit from comparable vinylogous amide conjugation. The structural difference that accounts for their 10-fold different reactivities lies in the lengths of the scissile cyclopropyl bonds (FIG. 9). CBI has bond lengths of 1.508 Å and 1.532 Å for the C8b-C9a and C8b-C9 bonds, respectively, while those of CBQ are 1.525 A and 1.539 Å. In turn, this may be attributed to the perfect geometrical (backside) alignment of the CBQ cyclopropane not accessible to CBI. Presumably, this increases the CBQ cyclopropane conjugation, lengthens the scissile cyclopropane bonds and results in an increased reactivity. In contrast to CBI and CBQ which have similar c bond lengths but different cyclopropyl alignments, CBQ and CNA have similar cyclopropyl alignments but substantially different $\chi_1$ dihedral angles and different c bond lengths of 1.336 versus 1.376 Å, respectively. This difference, diagnostic of the extent of vinylogous amide conjugation, is accompanied by a large increase in the CNA scissile cyclopropane bond lengths indicative of a much greater degree of conjugation and accounts for over a hundred-fold difference in reactivity. Thus, the degree of cyclopropane conjugation and its resulting reactivity is not only related to its geometrical alignment but also to the extent of the cross-conjugated vinylogous amide stabilization.

Thus, the geometrical constraints imposed by the fused five-membered C-ring found in the natural products dictate the regioselectivity of cleavage of the cyclopropane ring. More importantly, the agents display a beautiful interplay between the cross-conjugated stability provided by the vinylogous amide and the extent of cyclopropane conjugation that is central to their functional reactivity. Structural perturbations that diminish the vinylogous amide conjugation, increase the cyclopropyl conjugation and its inherent reactivity. One particularly important structural perturbation is the $\chi_1$ dihedral angle of the linking amide of the N-acyl derivatives of the alkylation subunits. As the $\chi_1$ dihedral angle is increased, the nitrogen lone pair remains conjugated with the acyl group carbonyl disrupting the vinylogous amide conjugation resulting in very substantial increases in the cyclopropane reactivity. One fundamental insight gained from these comparisons is the extent of the vinylogous amide conjugation and the contribution it makes to the unusual stability of the CBI and DSA alkylation subunits.

Catalysis of the DNA Alkylation Reaction. The remarkable chemical stability of 1–3 and the acid-catalysis requirement for addition of typical nucleophiles have led to the assumption that the DNA alkylation must also be an acid-catalyzed reaction. Although efforts have gone into supporting the extent and role of this acid catalysis, it remains largely undocumented for the DNA alkylation reaction. At pH 7.4, the DNA phosphate backbone is fully ionized (0.0001–0.00004% protonated). Consequently, it is unlikely that the catalysis is derived from a phosphate backbone delivery of a proton to the C4 carbonyl as advanced in related efforts. Although increases in the local hydronium ion concentrations surrounding "acidic domains" of DNA have been invoked to explain DNA mediated acid-catalysis, nucleotide reactivity, and extrapolated in studies with 1 to alkylation site catalysis, the remarkable stability of 1–3 even at pH 5 suggests that it is unlikely to be the source of catalysis. Consistent with this, the rate of the DNA alkylation reaction exhibits only a very modest pH dependence below pH 7 and essentially no dependence in the more relevant pH 7–8 range.

In conjunction with the results of these studies which document the lack of pH dependence on the rate of DNA alkylation and related studies that demonstrated that a rigid N$^2$ amide substituent is required for catalysis, an alternative source of catalysis became apparent. The studies detailed herein along with a number of additional unrelated observations have led us to propose that catalysis for the DNA alkylation reaction is derived from a DNA binding-induced conformational change in the agent that disrupts the vinylogous amide stabilization of the alkylation subunit and activates the agent for nucleophilic addition. This conformational change results from adoption of a helical bound conformation that follows the curvature and pitch of the DNA minor groove. The helical rise in the bound conformation of the rigid agents is adjusted by twisting the linking $N^2$ amide which is the only available flexible site. The twisting of the $\chi_1$ dihedral angle of the linking amide ($\chi_2 \sim 0°$) diminishes the $N^2$ lone pair conjugation with the cyclohexadienone, disrupts the vinylogous amide stabilization of .the alkylation subunit, and increases its inherent reactivity. An alternative possibility involves a twisting of the $\chi_2$ dihedral angle diminishing the amide conjugation and increasing the $N^2$ vinylogous amide conjugation. This would increase the basicity of the C4 carbonyl leading to more effective protonation. Notably, both are consistent with the studies that demonstrate even subtle perturbations in the vinylogous amide have a remarkably large impact on reactivity ($\rho = -3.0$). Although our present studies do not directly distinguish between these two possibilities, the latter reflects changes that occur upon N-deacylation (e.g., N—BOC-CBI to CBI, decreased reactivity) while the former reflects the changes observed in going to the product of the reaction (fully engaged amide, $\chi_2 = 0°$; no vinylogous amide, $\chi_1 \sim 20$–$35'$ and lengthened bond c). It is consistent with a DNA bound conformation of duocarmycin SA established by $^1H$ NMR which exhibited at $44 \pm 2°$ twist between the planes of the two subunits with the bulk of the twist being accommodated in $\chi_1$. The remarkably large and appropriate reactivity changes observed herein that accompany such a decoupling of the vinylogous amide including that resulting from a twist in the $\chi_1$ dihedral angle is consistent with this as a source of catalysis. The reactivity of N—CO$_2$Me-CNA is extraordinary exhibiting a $t_{1/2}$ of only 2.1 h at pH 7 in the absence of deliberate added acid catalysis. It is $10^3$–$10^4\times$ more reactive than N—BOC-DSA and represents an agent that benefits from little, if any, vinylogous amide stabilization. This level of reactivity is greater than that required. In fact it is the reactivity and $\chi_1$ dihedral angle of N—BOC-CBQ that may more closely approximate that required for the DNA alkylation catalysis provided by the DNA binding induced conformational change in 1–3. Its inherent reactivity at pH 7 coupled with the rate enhancements afforded a bound species that might provide a further $10^2\times$ rate acceleration approximates the rates observed with the DNA alkylation reaction.

This has important ramifications on the source of the DNA alkylation selectivity. The inherent twist and helical rise of the bound conformation of the agent is greatest within the narrower, deeper AT-rich minor groove. This leads to preferential activation of the agent for DNA alkylation within extended AT-rich minor groove sites and complements their preferential AT-rich noncovalent binding selectivity. Thus, both shape-selective recognition (preferential AT-rich noncovalent binding) and shape-dependent catalysis (extended AT-rich>GC-rich activation by twist in $N^2$ amide) combine to restrict $S_N2$ alkylation to accessible adenine N3 nucleophilic sites within the preferred binding sites. Importantly, this ground state destabilization of the substrate only activates the agent for a rate determining $S_N2$ nucleophilic addition and requires the subsequent proper positioning and accessibility to an adenine N3 site.

Figure 18:
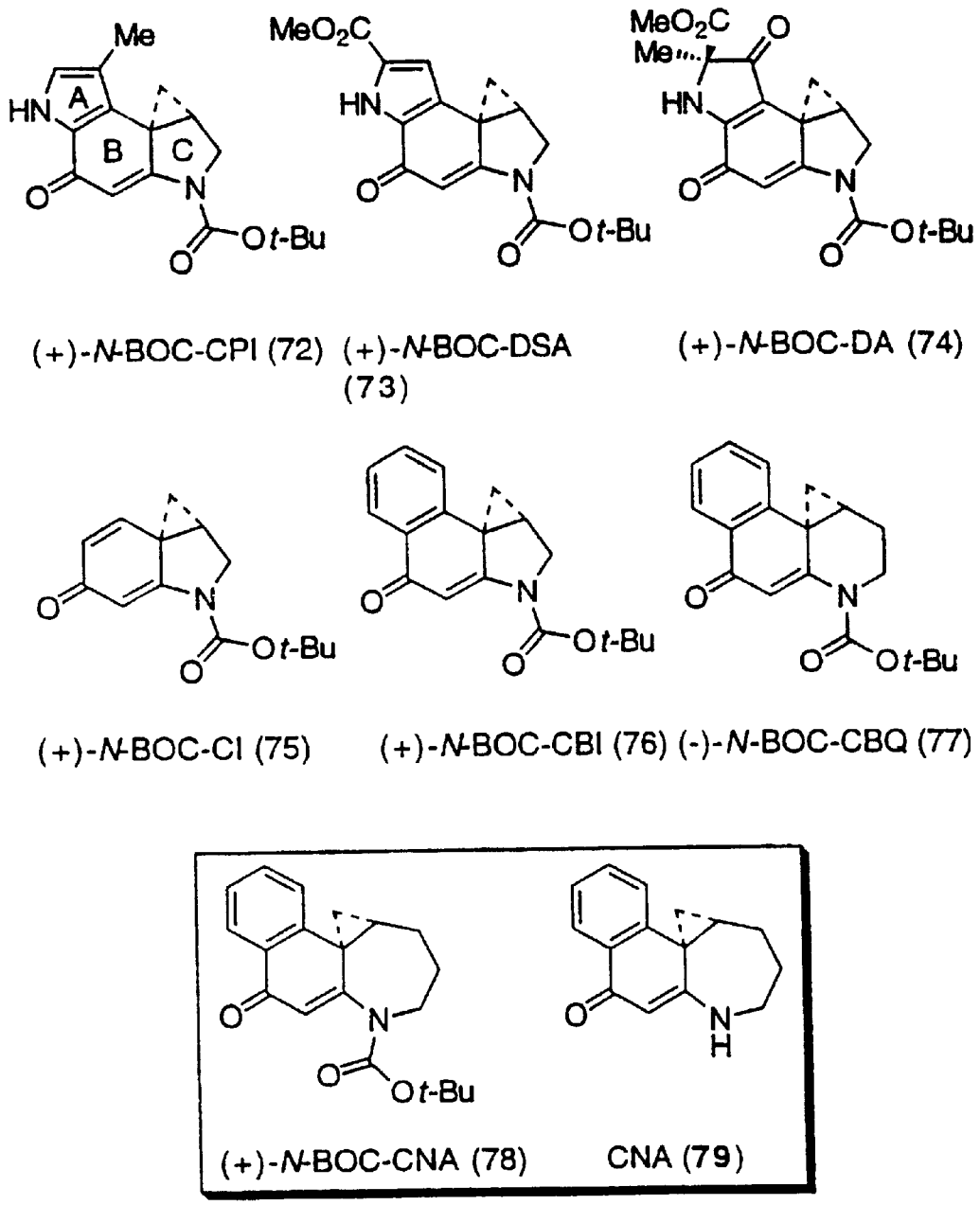
FIG. 18 shows the structure of analog compounds 72–79.

This source of catalysis requires an extended and rigid $N^2$ amide substituent and the absence of such a substituent with 72–74 (FIG. 18) accounts nicely for their slow and ineffective DNA alkylation. The noncovalent binding derived from the attached right-hand subunits accounts for a much smaller part of the difference in the rates of DNA alkylation between 72–74 and 1–3. More importantly, this source of catalysis would lead to distinctions, not similarities, in the DNA alkylation selectivities of 72–74 versus 1 contrary to the consequences of alternative proposals that have been advanced.

In Vitro Cytotoxic Activity. The in vitro cytotoxic activity of the agents proved to be consistent with past observations that have illustrated a direct correlation Bbetween solvolysis stability and cytotoxic potency. The CNA-based agents exhibited cytotoxic activity that was less potent than the corresponding duocarmycin based agents but more potent than the corresponding CI-based agents (FIGS. 19 and 20). The natural enantiomers of the CNA-based agents were found to be more potent than the unnatural enantiomers. Interestingly, the natural enantiomer of the full analog of duocarmycin SA, CNA-TMI (87), was only 5–10× more potent than N—BOC-CNA (78) and the difference in potency of the unnatural enantiomers was even smaller (1–2×). While this may simply be due to the extraordinary reactivity of the agents which preclude effective DNA alkylation, this also suggests that the twisted conformation of the full analogs may be sufficient to disfavor minor groove binding providing agents that are comparable to analogs lacking the attached DNA binding subunits altogether.

Aqueous Solvolysis of N—BOC-CNA (78) and CNA (79). Samples of 78 (150 $\mu$g) and 79 (150 [g) were dissolved in CH$_3$OH (1.5 mL) and the resulting solutions were mixed with aqueous buffer (pH 3, 1.5 mL, 4:1:20 (v:v:v) 0.1 M citric acid, 0.2 M Na$_2$HPO$_4$, and deionized H$_2$O respectively). Similarly, a solution of 78 (150 $\mu$g) in CH$_3$OH (1.5 mL) was mixed with deionized H$_2$O (pH 7, 1.5 mL). The UV spectra of the solutions were measured immediately after mixing with the appropriate aqueous solution. The blank and the solvolysis reaction solutions were stoppered, protected from light, and allowed to stand at 25° C. The total reaction times reflect those required to observe no further change in absorbance. For the solvolysis of 78 at pH 3, the UV spectrum was taken every 30 s for 10 min and then every 3 min for the next 40 min. The decrease of the absorbance at 319 nm was monitored. The solvolysis rate was calculated from the least squares treatment ($r=0.998$) of the slope of a plot of time versus 1 n[$A_0-A_f$)/($A-A_f$)]; $\kappa=6.90 \times 10^{-3}$ s$^{-1}$, $t_{1/2}=1.7$ min, 0.028 h. For the solvolysis of 78 at pH 7, the UV spectrum was monitored every 5 min for 19 h. The rate was calculated from the least squares treatment of the same type of plot as above ($r=0.999$); $\kappa=9.16 \times 10^{-5}$ s$^{-1}$, $t_{1/2}=126$ min, 2.1 h. For the solvolysis of 79 at pH 3, the UV spectrum was monitored every 2 min for the first 110 min and then every 10 min for the next 4 h. The decrease in the absorbance at 345 nm was recorded. The solvolysis rate constant was calculated from the least squares treatment of the same type of plot as above ($r=0.999$); $\kappa=3.10 \times 10^{-4}$ s$^{-1}$, $t_{1/2}=37$ min, 0.62 h.

Since these observations sharply contrast the proposed important role of acid catalysis for activation of the agents toward DNA alkylation which has served as the basis for one prominent proposal for the origin of the DNA alkylation selectivity, we have examined in detail the pH dependence of the rate of DNA alkylation for duocarmycin SA (1) and CCBI-TMI over a physiologically relevant range. The study was conducted by quantitating the relative ($\kappa_{rel}$) and pseudo first-order rate constants ($\kappa_{obs}$) for alkylation of the single, w794 high affinity alkylation site (5'-AATT$\underline{A}$) at a pH of 6.0, 6.6, 7.1, 7.6, and 8.1 for (+)-duocarmycin SA (1) and at a pH of 6.1, 6.8, 7.6, and 8.0 for (+)-CCBI-TMI (3, $10^{-6}$ M, 25° C., 10 mM phosphate buffer, 0–4 h). Although the rate of DNA alkylation was found to increase with decreasing pH in both cases, the rate change was remarkably small (<3× over 2 pH units) and inconsistent with a first-order dependence of acid concentration. Between pH 6–7, the slope of the plot of pH versus log $\kappa_{obs}$ was 0.2–0.3, far lower than that of 1.0 required of a first-order dependence on acid concentration. Moreover, between pH 7 and 8, which may be considered the physiologically relevant range, the rate dependence on pH essentially disappeared. A qualitative comparison of the pseudo first-order rate constant for DNA alkylation at this site, $\kappa=1.58\times10^{-4}$ s$^{-1}$ (pH 7.6) for 1 and $\kappa=3.36\times10^{-4}$ (pH 7.6) for 3 with the calculated first-order rate constants for acid-catalyzed solvolysis ($\kappa=2.7\times10^{-11}$ s$^{-1}$ and $\kappa=2.5\times10^{-11}$ s$^{-1}$,respectively) at pH 7.6 suggest that the bulk of catalysis for the DNA alkylation reaction cannot be accounted for by this source. Perhaps the magnitude of this difference is best recognized by simply noting that at pH 7.6, the calculated $t_{1/2}$ for solvolysis of 1 is 820 years ($3\times10^5$ d) while that of the DNA alkylation is 1.2 h.

Moreover, this rate of DNA alkylation was relatively independent of the buffer exhibiting only small differences in $\kappa_{obs}$ and the buffer had little impact on the pH dependence. The presence or absence of EDTA had or no effect on the rate of DNA alkylation for CCBI-TMI in either Tris or phosphate buffer and the alkylation was somewhat slower in phosphate versus Tris buffer (1.7–1.5×).

Throughout the pH range, (+)-CCBI-TMI was shown to alkylate the w794 high affinity alkylation site 1.9–2.5× faster than (+)-1, corresponding nicely with earlier studies[9] in which CCBI-TMI proved to exhibit the fastest relative rate at this same site: CCBI-TMI (2.5×)>MCBI-TMI (1.9×) >CBI-TMI (1.0×)>DSA (0.9×) (pH 7.5, Table X). In these studies, the rate of DNA alkylation did not correlate with the relative reactivity of the agents toward acid-catalyzed solvolysis (MCBI>CBI>CCBI) suggesting that other factors are responsible for the catalysis of the DNA alkylation reaction.

The relative lack of dependence on acid-concentration (pH) especially in the relevant pH range of 7–8, in conjunction with other studies have suggested an alternative source of catalysis responsible for the rapid rate of DNA alkylation by 1–3. We have proposed that catalysis for the DNA alkylation reaction is derived from a DNA binding induced conformational change in the agent that disrupts the $N^2$ vinylogous amide stabilization of the alkylation subunit and activates the agent for nucleophilic addition. This conformational change results from adoption of a helical bound conformation that follows the curvature and pitch of the DNA minor groove. The helical rise in the bound conformation of the rigid agents is adjusted by twisting the linking $N^2$ amide which is the only available flexible site. The twisting of the linking amide diminishes the $N^2$ lone pair conjugation with the cyclohexadienone, disrupts the vinylogous amide stabilization of the alkylation subunit, and increases its inherent reactivity. For the substituted CBI series of agents, the impact of the C7 substituent (R=CN≧OCH$_3$>H) is unrelated to its effect on the rate of acid-catalyzed nucleophilic addition (R=OCH$_3$>H>CN) and seems to be related simply to its presence rather than electronic nature. We suggest this is due to the resulting extended length of the alkylation subunit with substituent placement in the minor groove and the corresponding increase in the inherent twist of the linking $N^2$ amide that accompanies minor groove binding. The documentation of remarkably large and appropriate reactivity increases that accompany the decoupling of the vinylogous amide stabilization within the alkylation subunits support this as the source of catalysis.

EXAMPLES

A Experimental 2-((tert-Butyloxy)carbonyl)-1,2,8,8a-tetrahydrocyclopropa[c]pyrrolo3,2e]indol-4-one-6-carboxylic Acid (7).

A solution of 4 (56 mg, 163 µmol) in THF—CH$_3$OH—H$_2$O (3:2:1, 1.6 mL) was treated with 0.17 mL of aqueous 1 N LiOH (1.05 equiv) and the reaction mixture was warmed at 60° C. under Ar for 1 h. An additional 0.041 mL of aqueous 1 N LiOH (0.25 equiv) was added and the solution was warmed at 60° C. for an additional 30 min. The reaction mixture was allowed to cool to 25° C. and the solvent was removed under a stream of N$_2$. H$_2$O (2 mL) was added and the aqueous layer was extracted with EtOAc (2×2 mL). EtOAc (2 mL) was added to the aqueous layer, followed by aqueous 1 N KHSO$_4$ (0.21 mL, 1 equiv). The mixture was diluted with H$_2$O (35 mL) and extracted with EtOAc (3×35 mL). The combined organic extract was washed with H$_2$O (35 mL) and dried (Na$_2$SO$_4$). Concentration under reduced pressure provided 7 (50.0 mg, 93%) as a yellow film: $^1$H NMR (acetone-d$_6$, 400 MHz) δ 11.15 (s, 1H, NH), 6.77 (s, 1H, C3-H), 6.75 (d, 1H, J=2.0 Hz, C7-H), 4.03–4.01 (m, 2H, C1-H$_2$), 2.90–2.86 (m, 1H, C8a-H), 1.70 (dd, 1H, J=7.7, 4.4 Hz, C8-H), 1.52 (s, 9H, C(CH$_3$)$_3$), 1.40 (t, 1H, J=4.4 Hz, C8-H); IR (film) ν$_{max}$ 3204, 2963, 1721, 1667, 1597, 1393, 1277, 1258, 1155, 1137, 798 cm$^{-1}$; FABHRMS (NBA-CsI) m/z 331.1290 (M$^+$+H, C$_{17}$H$_{18}$N$_2$O$_5$ requires 331.1294).

(+)-7: $[\alpha]_D^{23}$+190 (c 0.2, CH$_3$OH).
ent-(−)-7: $[\alpha]_D^{23}$−193 (c 0.2, CH$_3$OH).

General Procedure for the Preparation of 13–16: 7-[(Methyl 1,2-Dihydro-3H-pyrrolo[3,2-e]indole-3-yl)carbonyl-7-carboxylate]3-((tert-butyloxy)carbonyl)- 1-(chloromethyl)-5-hydroxy-1,2-dihydro-3H-pyrrolo[3,2-e]indole (15).

A solution of 7 (3.1 mg, 9.4 µmol) in EtOAc (0.70 mL) under Ar was treated with 4 N HCl-EtOAc ((12 µL, 47 µmol, 5 equiv) over 10 s. The yellow reaction mixture was stirred at 25° C. for 30 min and was concentrated under a stream of N$_2$. The resultant yellow residue containing 8 was dissolved in DMF (0.17 mL) and treated sequentially with 11 (1.7 mg, 7.9 µmol, 0.9 equiv) and EDCI (3.4 mg, 17.6 µmol, 2.0 equiv). The reaction mixture was stirred for 2 h at 25° C. before the solvent was removed under reduced pressure and the residual solid was slurried in 0.5 mL H$_2$O. The solid was collected by centrifugation and washed with 1% aqueous HCl (1×0.5 mL) and H$_2$O (1×0.5 mL). Drying the solid in vacuo afforded 15 (4.3 mg, 96%) as a tan solid: mp 188–190° C. (d); $^1$H NMR (acetone-d$_6$, 400 MHz) δ 10.99 (s, 1H, NH), 10.40 (s, 1H, NH), 8.81 (br s, 1H, OH), 8.41 (m, 1H, C4'-H), 7.59 (br s, 1H, C4-H), 7.41 (d, 1H, J=8.9 Hz, C5'-H), 7.22 (d, 1H, J=1.5 Hz), 7.12 (s, 1H), 4.80–4.62 (m, 2H), 4.20–4.10 (m, 2H), 4.04 (dd, 1H, J=11.8, 4.0 Hz), 4.04–3.92 (m, 1H, C1-H), 3.89 (s, 3H, OCH$_3$), 3.73 (t, 1H, J=9.3 Hz, C2'-H), 3.49 (t, 2H, J=8.3 Hz, C1'-H$_2$), 1.55 (s, 9H, C(CH$_3$)$_3$); IR (neat) ν$_{max}$ 3327, 2975, 2933, 1690, 1669, 1607, 1524, 1436, 1389, 1369, 1327, 1255, 1213, 1141 cm$^{-1}$; FABHRMS (NBA-CsI) m/z 697.0809 (M$^+$+Cs, C$_{29}$H$_{29}$N$_4$O$_6$Cl requires 697.0830).

(1S)-15: $[\alpha]_D^{22}$−23 (c 0.2, THF).
ent-(1R)-15: $[\alpha]_D^{23}$+27 (c 0.2, THF).

General Procedure for the Preparation of 17–20, Method A: 6-[7-[Methyl 1,2-Dihydro-(3H-pyrrolo[3,2-e]indole-3-yl) carbonyl-7-carboxylate]1,2-dihydro-(3H-pyrrolo[3,2-e] indole-3-yl)carbonyl]-2-((tert-butyloxy)carbonyl)-1,2,8,8a-tetrahydrocyclopropa[c]pyrrolo[3,2-e]indol-4-one (20, CDPI$_2$-DSA).

A portion of NaH (1.1 mg, 60%, 26.7 µmol, 10 equiv) in DMF at 0° C. under Ar was treated with a solution of 16 (2.0 mg, 2.67 µmol, 1.0 equiv) in DMF (0.25 mL), and the reaction mixture was stirred for 45 min at 0° C. The reaction mixture was directly subjected to flash chromatography (0.5×5 cm SiO$_2$, 15% DMF-toluene) to afford 20 (1.8 mg, 95%) as a pale yellow solid: mp 213–215° C. (d); $^1$H NMR (DMF-d$_7$, 400 MHz) δ 11.99 (s, 1H, NH), 11.79 (s, 1H, NH), 11.73 (d, 1H, J=1.6 Hz, NH), 8.42–8.20 (m, 2H), 7.46 (app t, 2H, J=9.2 Hz), 7.20 (d, 1H, J=1.6 Hz), 7.17 (d, 1H, J=1.4 Hz), 6.81 (s, 1H), 6.68 (s, 1H), 4.75 (t, 2H, J=8.4 Hz), 4.55 (app q, 2H, J=7.9 Hz), 4.07 (dd, 1H, J=11.2, 4.9 Hz), 4.04–3.99 (m, 1H), 3.93 (s, 3H), 3.57–3.45 (m, 4H, partially obscured by H$_2$O), 3.00 (dt, 1H, J=7.8, 4.3 Hz, C8a-H), 1.82 (dd, 1H, J=7.7, 3.7 Hz, C8-H), 1.53 (s, 9H, C(CH$_3$)$_3$), 1.49 (t, 1H, J=4.4 Hz, C8-H); IR (neat) ν$_{max}$ 3324, 2958, 2931, 2871, 1709, 1703, 1620, 1582, 1530, 1511, 1503, 1434, 1378, 1348, 1256, 1211, 1163, 1143, 1022 cm$^{-1}$; FABHRMS (NBA) m/z 713.2757 (M$^+$+H, C$_{40}$H$_{36}$N$_6$O$_7$ requires 713.2724).

(+)-CDPI$_2$-DSA (20): [α]$_D^{23}$+56 (c 0.1, DMF).
ent-(−)-CDPI$_2$-DSA (20): [α]$_D^{23}$−60 (c 0.1, DMF).
N-(Methyl 1H-Indol-5-yl-2-carboxylate)-3-((tert-butyloxy) carbonyl)-1-(chloromethyl)-5-hydroxy-1,2-dihydro-3H-pyrrolo[3,2-e]indole-7-carboxamide (13):

(4.3 mg, 96%) as a tan solid: mp 215–218° C. (d); $^1$H NMR (acetone-d$_6$, 400 MHz) δ 10.92 (s, 1H, NH), 10.62 (s, 1H, NH), 9.56 (s, 1H, OH), 8.77 (br s, 1H, NHCO), 8.29 (d, 1H, J=1.5 Hz, C4'-H), 7.64 (dd, 1H, J=8.9, 2.0 Hz, C6'-H), 7.58 (br s, 1H, C4-H), 7.51 (d, 1H, J=8.9Hz, C7'-H), 7.31 (d, 1H, J=1.5 Hz), 7.18 (d, 1H, J=1.2 Hz), 4.17 (t, 1H, J=10.5 Hz, C2-H), 4.08 (dd, 1H, J=10.8, 3.4 Hz), 4.01 (dd, 1H, J=11.6, 4.5 Hz), 3.91 (s, 3H, OCH$_3$), 3.73 (dd, 1H, J=10.6, 9.2 Hz), 2.95 (m, 1H), 1.55 (s, 9H, C(CH$_3$)$_3$); IR (neat) ν$_{max}$ 3329, 2976, 1693, 1669, 1592, 1535, 1479, 1438, 1393, 1366, 1348, 1253, 1154 cm$^{-1}$; FABHRMS (NBA-NaI) m/z 538.1602 (M$^+$+H, C$_{27}$H$_{27}$N$_4$O$_6$Cl requires 538.1619).

(1S)-13: [α]$_D^{22}$+3 (c 0.2, THF).
ent-(1R)-13: [α]$_D^{23}$−4 (c 0.2, THF).
N-{2-[N-(2-Methoxycarbonyl-1H-indol-5-yl)carbamoyl-1H-indol-5-yl}-3-(tert-butyloxycarbonyl)-1-(chloromethyl)-5-hydroxy-1,2-dihydro-3H-pyrrolo[3,2-e] indole-7-carboxamide (14):

The coupling reaction mixture was stirred for 4 h at 25° C. and chromatography (0.5×6.0 cm SiO$_2$, 7–10% CH$_3$OH—CH$_2$Cl$_2$ gradient elution) afforded pure 14 (80%) as a tan solid: $^1$H NMR (acetone-d$_6$, 400 MHz) δ 10.95 (s, 1H, NH), 10.92 (s, 1H, NH), 9.62 (s, 1H, NH), 9.55 (s, 1H, NH), 8.31–8.28 (m, 2H), 7.68 (dd, 1H, J=8.9, 1.9 Hz), 7.60 (d, 1H, J=8.8 Hz), 7.55 (d, 1H, J=8.8 Hz), 7.52 (d, 1H, J=8.9 Hz), 7.34 (s, 1H), 7.29 (s, 1H), 7.18 (d, 1H, J=2.0 Hz), 4.17 (t, 1H, J=10.7 Hz, C2-H), 4.09 (dd, 1H, J=11.0, 3.0 Hz, C2-H), 4.03 (dd, 1H, J=10.5, 4.5 Hz, CHHCl), 3.98–3.88 (m, 1H, C1-H), 3.89 (s, 3H, OCH$_3$), 3.73 (dd, 1H, J=12.6, 11.0 Hz, CHHCl), 1.55 (s, 9H, C(CH$_3$)$_3$); IR (neat) ν$_{max}$ 3277, 2921, 1694, 1650, 1541, 1254, 1141 cm$^{-1}$; FABMS (NBA-CsI) m/z 829 (M$^+$+Cs, C$_{36}$H$_{33}$N$_6$O$_7$Cl requires 829).
7-[7-[(Methyl 1,2-Dihydro-3H-pyrrolo[3,2-e]indole-3-yl) carbonyl-7-carboxylate]1,2-dihydro-(3H-pyrrolo[3,2-e] indole-3-yl)carbonyl]-3-((tert-butyloxy)carbonyl)-1-(chloromethyl)-5-hydroxy-1,2-dihydro-3H-pyrrolo[3,2-e] indole (16):

The coupling reaction mixture was stirred for 4 h at 25° C. followed by chromatography (0.5×5 cm SiO$_2$, 15% DMF-toluene) to afford pure 16 (57%) as a tan solid: mp 210–211° C. (d); $^1$H NMR (DMF-d$_7$, 400 MHz) δ 11.99 (s, 1H, NH), 11.74 (d, 1H, J=1.6 Hz), 11.09 (s, 1H, NH), 9.97 (br s, 1H, OH), 8.42 (br s, 1H), 8.41 (m, 2H), 7.50 (d, 1H, J=8.9 Hz), 7.46 (d, 1H, J=8.8 Hz), 7.39 (d, 1H, J=2.0 Hz), 7.23 (d, 1H, J=1.6 Hz), 7.18 (d, 1H, J=0.9 Hz), 4.79 (m, 2H), 4.76 (t, 2H, J=8.4 Hz), 4.27 (dd, 1H, J=10.7, 3.0 Hz), 4.21 (t, 1H, J=12.5 Hz), 4.10–4.00 (m, 2H), 3.92 (s, 3H), 3.95 (t, 1H, J=4.4 Hz), 3.56 (t, 4H, J=7.9 Hz), 1.57 (s, 9H); IR (neat) ν$_{max}$ 3321, 2956, 2925, 1701, 1609, 1508, 1431, 1370, 1335, 1253, 1208, 1142, 1020 cm$^{-1}$; FABHRMS (NBA) m/z 749.2480 (M$^+$+H, C$_{40}$H$_{37}$N$_6$O$_7$Cl requires 749.2491).

(1S)-16: [α]$_D^{22}$−24 (c 0.1, DMF).
ent-(1R)-16: [α]$_D^{23}$+27 (c 0.2, DMF).
Method B: 6-[(Methyl 1,2-Dihydro-3H-pyrrolo[3,2-e] indole-3-yl)carbonyl-7-carboxylate]-2-((tert-butyloxy) carbonyl)-1,2,8,8a-tetrahydrocyclopropa[c]-pyrrolo[3,2-e] indol-4-one (19, CDPI$_1$-DSA).

A solution of 11 (2.0 mg, 9.1 μmol), EDCI (2.6 mg, 13.6 μmol, 1.5 equiv), and NaHCO$_3$ (3.8 mg, 45.5 μmol, 5 equiv) in DMF (0.18 mL) at 25° C. under Ar was treated with 7 (3.0 mg, 9.1 μmol) and the reaction mixture was stirred for 16 h at 25° C. The reaction mixture was directly subjected to flash chromatography (0.5×5 cm SiO$_2$, EtOAc) to afford 19 (2.3 mg, 51%) as a pale yellow film: $^1$H NMR (DMSO-d$_6$, 400 MHz) δ 12.00 (d, 1H, J=1.6 Hz, NH), 11.96 (s, 1H, NH), 8.13 (br s, 1H, C4'-H), 7.29 (d, 1H, J=9.2 Hz, C5'-H), 7.12 (d, 1H, J=1.2 Hz, C8'-H), 6.63 (s, 1H), 6.50 (s, 1H), 4.37 (m, 2H, C2'-H$_2$), 3.96 (dd, 1H, J=11.1, 4.8 Hz, C1-H), 3.90 (d, 1H, J=10.9 Hz, C1-H), 3.87 (s, 3H, OCH$_3$), 3.30 (m, 2H, C1-H$_2$, obscured by H$_2$O), 2.89 (dt, 1H, J=7.7, 4.8 Hz, C8a-H), 1.69 (dd, 1H, J=7.7, 4.0 Hz, C8-H), 1.43 (t, 1H, J=4.2 Hz, C8-H); IR (film) ν$_{max}$ 3302, 2958, 2930, 2849, 1710, 1692, 1613, 1434, 1390, 1366, 1311, 1256, 1212, 1140 cm$^{-1}$; FABHRMS (NBA-CsI) m/z 529.2080 (M$^+$+H, C$_{29}$H$_{28}$N$_4$O$_6$ requires 529.2087).

(+)-CDPI$_1$-DSA (19): [α]$_D^{22}$+89 (c 0.1, THF).
ent-(−)-CDPI$_1$-DSA (19): [α]$_D^{23}$−87 (c 0.1, THF).
N-(Methyl 1H-Indol-5-yl-2-carboxylate)-2-((tert-butyloxy) carbonyl)-1,2,8,8a-tetrahydrocyclopropa[c]pyrrolo[3,2-e] indol-4-one-7-carboxamide (17, Indole$_1$-DSA):

30 min at 0° C. followed by chromatography (0.5×5 cm SiO$_2$, 15% DMF-toluene) afforded 17 (2.0 mg, 71%) as a pale yellow solid: mp 204–205° C. (d); $^1$H NMR (acetone-d$_6$, 400 MHz) δ 11.43 (s, 1H, NH), 10.91 (s, 1H, NH), 9.66 (s, 1H, NH), 8.25 (d, 1H, J=1.6 Hz, C4'-H), 7.64 (dd, 1H, J=8.9, 1.6 Hz, C6'-H), 7.51 (d, 1H, J=8.9 Hz, C7'-H), 7.19 (s, 1H), 6.80 (s, 1H), 6.77 (br s, 1H), 4.03 (m, 2H, C1-H$_2$), 3.88 (s, 3H, OCH$_3$), 2.82 (m, 1H, C8a-H, partially obscured by H$_2$O), 1.70 (dd, 1H, J=7.6, 4.0 Hz, C8-H), 1.51 (s, 9H, C(CH$_3$)$_3$), 1.45 (t, 1H, J=4.2 Hz, C8-H); IR (neat) ν$_{max}$ 3189, 2958, 2922, 1711, 1651, 1593, 1533, 1443, 1393, 1370, 1280, 1257, 1145, 1090 cm$^{-1}$; FABMS (NBA) m/z 503 (M$^+$+H, C$_{27}$H$_{26}$N$_4$O$_6$ requires 503).

(+)-Indole$_1$-DSA (17): [α]$_D^{23}$+60 (c 0.1, DMF).
ent-(−)-Indole$_1$-DSA (17): [α]$_D^{23}$−67 (c 0.1, DMF).
N-{2-[N-(2-Methoxycarbonyl-1H-indol-5-yl)]carbamoyl-1H-indol-5-yl}-2-(tert-butyloxycarbonyl)-1,2,8,8a-tetrahydrocyclopropa[c]pyrrolo[3,2-e]indol-4-one-6-carboxamide (18, Indole$_2$-DSA):

Chromatography (0.5×6.0 cm SiO$_2$, 5–10% CH$_3$OH—CH$_2$Cl$_2$ gradient elution) afforded 18 (64%) as a tan solid: $^1$H NMR (DMSO-d$_6$, 400 MHz) δ 11.92 (s, 1H, NH), 11.76 (br s, 1H, NH), 11.70 (s, 1H, NH), 10.16 (s, 1H, NH), 9.99 (s, 1H, NH), 8.14 (d, 2H, J=6.8 Hz), 7.59 (d, 1H, J=8.9 Hz), 7.44–7.42 (m, 3H), 7.37 (s, 1H), 7.17 (s, 1H), 6.78 (s, 1H), 6.54 (s, 1H), 3.98–3.89 (m, 2H, C1-H$_2$), 3.87 (s, 3H, OCH$_3$), 2.93 (m, 1H, C8a-H), 1.69 (m, 1H, C8-H), 1.49 (s, 9H, C(CH$_3$)$_3$), 1.34 (t, 1H, J=7.4 Hz, C8-H); IR (neat) ν$_{max}$ 3284, 2930, 1709, 1594, 1541, 1255, 1140 cm$^{-1}$; FABHRMS (NBA-CsI) m/z 793.1357 (M$^+$+Cs, C$_{36}$H$_{32}$N$_6$O$_7$ requires 793.1387).

(+)-18: [α]$_D^{25}$+58 (c 0.07, THF).
ent-(−)-18: [α]$_D^{25}$−50 (c 0.02, THF).
N-{2-[N-(2-Methoxycarbonyl-1H-indol-5-yl)]carbamoyl-1H-indol-5-yl}-3-acetyl-1-(chloromethyl)-5-hydroxy-1,2-dihydro-3H-pyrrolo[3,2-e]indole-7-carboxamide (22).

A suspension of 14 (1.6 mg, 2.3 μmol, 1.0 equiv) in 3.4 N HCl-EtOAc (0.6 mL) was stirred for 30 min at 25° C. The reaction mixture was concentrated and the residue of 21 was taken up in DMF (0.1 mL) and treated sequentially with CH₃COOH (16 μL, 0.175 M in DMF, 1.2 equiv) and EDCI (1.3 mg, 6.9 μmol, 3.0 equiv). The reaction mixture was stirred for 15 h at 25° C. The solvent was removed under reduced pressure and the residual solid was slurried in 0.4 mL H₂O. The solid was collected by centrifuigation and washed with 1% aqueous HCl (0.4 mL) and H₂O (0.4 mL) to afford crude 22. Flash chromatography (0.5×4.5 cm SiO₂, 25% DMF-toluene) afforded pure 22 (0.6 mg, 40%) as a tan solid: $^1$H NMR (DMSO-d₆, 400 MHz) δ 11.91 (s, 1H, NH), 11.70 (s, 1H, NH), 11.34 (s, 1H, NH), 10.15 (s, 1H, NH), 10.07 (s, 1H, NH), 9.76 (s, 1H, OH), 8.16 (s, 2H), 7.73 (s, 1H), 7.59 (dd, 1H, J=9.3, 1.9 Hz), 7.53 (d, 1H, J=8.9 Hz), 7.45 (t, 2H, J=9.1 Hz), 7.40 (s, 1H), 7.38 (s, 1H), 7.17 (d, 1H, J=0.9 Hz), 4.35 (m, 1H, C2-H), 4.14–4.11 (m, 1H, C2-H), 4.05–4.01 (m, 2H, CHHCl, C1-H), 3.903.87 (m, 1H, CHHCl), 3.87 (s, 3H, OCH₃), 2.16 (s, 3H, CH₃); IR (neat) $v_{max}$ 3279, 2922, 1678, 1645, 1556, 1532, 1434, 1410, 1214, 1017 cm⁻¹; ESIMS m/z 639 (M⁺+H, C₃₃H₂₇N₆O₇Cl requires 639).

N-{2-[N-(2-Methoxycarbonyl-1H-indol-5-yl)]carbamoyl-1H-indol-5-yl}-2-acetyl-1,2,8,8a-tetrahydrocyclopropa[c]pyrrolo[3,2-e]indole4-one-6-carboxamide (23, Indole₂-DSA-COCH₃).

A suspension of NaH (0.5 mg, 60%, 12.5 μmol, 5.0 equiv) in THF (0.12 mL) at 0° C. under Ar was treated with a solution of 22 (2.5 mg, 2.5 μmol, 1.0 equiv) in 50% THF-DMF (0.24 mL). The reaction mixture was stirred for 30 min at 0° C. The crude reaction mixture was purified by preparative TLC (12×20 cm SiO₂, 20% DMF-toluene) to afford 24 (1.1 mg, 70%) as a pale yellow solid: $^1$H NMR (DMSO-d₆, 400 MHz) δ 12.10 (br s, 1H, NH), 11.91 (s, 1H, NH), 11.72 (s, 1H, NH), 10.17 (s, 1H, NH), 10.01 (s, 1H, NH), 8.15 (d, 2H, J=6.8 Hz), 7.59 (dd, 1H, J=8.9, 2.0 Hz), 7.45 (s, 2H), 7.44 (d, 1H, J=8.7 Hz), 7.37 (s, 1H), 7.17 (s, 1H), 6.79 (s, 1H), 4.14–4.10 (m, 2H, C1-H₂), 3.87 (s, 3H, OCH₃), 2.95 (m, 1H, C8a-H), 2.19 (s, 3H, CH₃), 1.71 (m, 1H, C8-H), 1.46 (m, 1H, C8-H); IR (neat) $v_{max}$ 3282, 2923, 1646, 1590, 1539, 1390, 1256 cm⁻¹; ESIMS (negative ion) m/z 601 (M⁻-H, C₃₃H₂₆N₆O₆ requires 601).

(+)-23: $[\alpha]_D^{25}$+24 (c 0.07, DMF).
ent-(−)-24: $[\alpha]_D^{25}$−20 (c 0.02, DMF).

N-{2-1N-(2-Methoxycarbonyl-1H-indol-5-yl)]carbamoyl-1H-indol-5-yl}-1,2,8,8a-tetrahydrocyclopropa[c]pyrrolo[3,2-e]indol-4-one-6-carboxamide (24, Indole₂-DSA-NH).

A suspension of crude 14 (4.0 mg, 7.0 μmol, 1.0 equiv) in 3.6 N HCl-EtOAc (1.3 mL) was stirred for 30 min at 25° C. The reaction mixture was concentrated and dried. The residue was taken up in DMF (0.45 mL) and added to a suspension of NaH (0.8 mg, 60%, 2.1 μmol, 3.0 equiv) at 0° C. The mixture was stirred for 30 min at 0° C. and filtered (4×0.5 cm SiO₂). The filtrate was concentrated and purified by PTLC (12×20 cm SiO₂, 30% DMF-toluene) to afford 24 (2.3 mg, 75%) as a pale yellow solid: $^1$H NMR (DMSO-d₆, 400 MHz) δ 11.95 (s, 1H, NH), 11.91 (s, 1H, NH), 11.67 (s, 1H, NH), 10.14 (s, 1H, NH), 9.90 (s, 1H, NH), 8.15 (s, 1H), 8.14 (s, 1H), 7.59 (dd, 1H, J=9.0, 2.0 Hz), 7.46 (s, 1H), 7.45–7.43 (m, 3H), 7.36 (d, 1H, J=1.8 Hz), 7.17 (d, 1H, J=1.3 Hz), 6.68 (d, 1H, J=2.0 Hz), 5.29 (s, 1H, C3-H), 3.87 (s, 3H, OCH₃), 3.68 (dd, 1H, J=10.4, 4.9 Hz, C1-H), 3.50 (d, 1H, J=10.8 Hz, C1-H), 2.93–2.91 (m, 1H, C8a-H), 1.55 (dd, 1H, J=7.8, 2.2 Hz, C8-H), 1.23 (m, 1H, C8-H); IR (neat) $v_{max}$ 3251, 2913, 1703, 1635, 1590, 1528, 1308, 1231, 1015 cm⁻¹; FABHRMS (NBA) m/z 561.1872 (M⁺+H, C₃₁H₂₄N₆O₅ requires 561.1886).

(+)-24: $[\alpha]_D^{25}$+27 (c 0.05, DMF).
ent-(−)-24: $[\alpha]_D^{25}$−28 (c 0.05, DMF).

7-[(Methyl 1,2-Dihydro-(3H-pyrrolo[3,2-e]indole-3-yl)carbonyl-7-carboxy-late)-3-(3-carbamoyl-1,2-dihydro-3H-pyrrolo[3,2-e]indol-7-yl)carbonyl]-1-(chloromethyl)-5-hydroxy-1,2-dihydro-3H-pyrrolo[3,2-e]indole (28).

A solution of 15 (5.0 mg, 8.8 μmol) in 4.0 N HCl-EtOAc (0.3 mL) was stirred for 40 min at 25° C. The reaction mixture was concentrated to afford crude 25. The crude hydrochloride salt 25 was taken up in DMF (0.17 mL) and treated sequentially with CDPI₁³⁰ (26, 2.0 mg, 8.34 μmol, 0.95 equiv) and EDCI (3.4 mg, 17.6 μmol, 2 equiv). The reaction mixture was stirred for 15 h at 25° C. The solvent was removed under reduced pressure and the residual solid was slurried in 0.5 mL H₂O and collected by centrifugation. The solid was washed with 1% aqueous HCl (1×0.5 mL) and H₂O (1×0.5 mL) and dried under reduced pressure. Chromatography (0.5×5 cm SiO₂, 30% DMF-toluene) afforded 28 (4.1 mg, 68%) as a yellow solid: $^1$H NMR (DMF-d₇, 400 MHz) δ 11.98 (s, 1H, NH), 11.51 (s, 1H, NH), 11.27 (s, 1H, NH), 10.11 (br s, 1H, OH), 8.44–8.32 (m, 2H), 7.92 (s, 1H, NH), 7.46 (d, 1H, J=9.0 Hz), 7.41 (s, 1H), 7.37 (d, 1H, J=8.9 Hz), 7.18 (s, 1H), 7.09 (s, 1H), 6.10 (s, 2H, NH₂), 4.89 (t, 1H, J=8.7 Hz), 4.81–4.74 (m, 2H), 4.64 (dd, 1H, J=11.1, 3.9 Hz), 4.30 (dd, 1H, J=10.6, 3.4 Hz), 4.27–4.20 (m, 1H), 4.16 (t, 2H, J=8.9 Hz), 4.05 (dd, 1H, J=10.6, 8.0 Hz), 3.93 (s, 3H, OCH₃), 3.53 (t, 2H, J=8.3 Hz, partially obscured by H₂O), 3.40 (t, 2H, J=8.3 Hz, partially obscured by H₂O); IR (neat) $v_{max}$ 3329, 2958, 1701, 1670, 1610, 1560, 1429, 1366, 1330, 1257, 1212 cm⁻¹; ESIMS m/z 692 (M⁺+H, C₃₆H₃₀N₇O₆Cl requires 692).

(1S)-28: $[\alpha]_D^{23}$+11 (c 0.1, DMF).
ent-(1R)-28: $[\alpha]_D^{23}$−10 (c 0.1, DMF).

7-[(Methyl 1,2-Dihydro-3H-pyrrolo[3,2e]indole-3-yl)carbonyl-7-carboxylate]-3-[(5,6,7-trimethoxyindol-2-yl)carbonyl]-1-(chloromethyl)-5-hydroxy-1,2-dihydro-3H-pyrrolo[3,2-e]indole (29).

A solution of 15 (3.6 mg, 5.7 μmol) in 4.0 N HCl-EtOAc (0.25 mL) was stirred for 30 min at 25° C. The reaction mixture was concentrated to afford crude 25 as a dark green solid. The crude hydrochloride salt 25 was taken up in DMF (0.11 mL) and treated sequentially with 27¹² (1.3 mg, 5.38 μmol, 0.95 equiv) and EDCI (2.2 mg, 11.32 μmol, 2 equiv). The reaction mixture was stirred for 6 h at 25° C. The solvent was removed under reduced pressure and the residual solid was slurried in 0.5 mL H₂O and collected by centrifugation. The solid was washed with 1% aqueous HCl (1×0.5 mL) and H₂O (1×0.5 mL) and dried under reduced pressure. Chromatography (0.5×5 cm SiO₂, 15% DMF-toluene) afforded 29 (2.5 mg, 70%) as a yellow solid: $^1$H NMR (DMSO-d₆, 400 MHz) δ 12.02 (s, 1H1, NH), 11.37 (s, 1H, NH), 11.27 (s, 1H, NH), 9.71 (br s, 1H, OH), 8.29 (m, 1H), 7.70 (br s, 1H), 7.34 (d, 1H, J=8.9 Hz, C7'-H), 7.23 (s, 1H), 7.15 (d, 1H, J=1.2 Hz), 6.98 (s, 1H), 6.81 (br s, 1H), 4.68–4.59 (m, 3H), 4.37 (dd, 1H, J=11.6, 3.0 Hz), 4.20 (dd, 1H, J=10.8, 3.0 Hz), 4.08–4.04 (m, 1H, C1-H), 3.92 (s, 3H, OCH₃), 3.88 (s, 3H, OCH₃) 3.88 (m, obscured by OCH₃, 1H, C2'-H), 3.81 (s, 3H, OCH₃), 3.78 (s, 3H, OCH₃), 3.43 (m, 2H, C1'-H₂); IR (neat) $v_{max}$ 3346, 2956, 2928, 2864, 1697, 1647, 1633, 1612, 1556, 1530, 1504, 1456, 1436, 1370, 1329, 1307, 1254, 1230, 1212, 1111, 1047, 1021 cm⁻¹; FABMS (NBA) m/z 699 (M⁺+H, C₃₆H₃₂N₅O₈Cl requires 699).

(1S)-29: $[\alpha]_D^{23}$−10 (c 0.08, DMF).
ent-(1R)-29: $[\alpha]_D^{23}$+11 (c 0.1, DMF).

2-[1(3-Carbamoyl-1,2-dihydro-3H-pyrrolo[3,2-e]indol-7-yl)carbonyl]-6-[7-methoxycarbonyl-1,2-dihydro-3H- pyrrolo[3,2-e]indol-3-yl)carbonyl]-1,2,8,8a-tetrahydrocyclopropa[c]pyrrolo[3,2-e]indole (30, CDPI-DSA-CDPI).

A suspension of NaH (0.6 mg, 60%, 16.0 μmol, 5.0 equiv) in DMF (0.1 mL) at 0° C. under Ar was treated with a solution of 28 (2.2 mg, 3.2 μmol, 1.0 equiv) in DMF (0.22 mL), and the reaction mixture was stirred for 30 min at 0° C. The reaction mixture was concentrated under reduced pressure and subjected to chromatography (0.5×6.0 cm $SiO_2$, 20–30% DMF-toluene gradient elution) to afford 30 (1.5 mg, 70%) as a yellow solid: $^1$H NMR (DMSO-$d_6$, 400 MHz) δ 12.05 (br s, 1H, NH), 12.00 (br s, 1H, NH), 11.69 (br s, 1H, NH), 8.17 (br s, 1H, C4'-H), 8.01 (d, 1H, J=8.9 Hz, C4"-H), 7.30 (d, 1H, J=8.5 Hz, C5'-H), 7.21 (d, 1H, J=8.6 Hz, C5"-H), 7.11 (s, 1H), 7.01 (s, 1H), 6.75 (s, 1H), 6.71 (s, 1H), 6.12 (s, 2H, $NH_2$), 4.61–4.59 (m, 1H, C1-H), 4.48–4.45 (m, 3H, C2'-$H_2$, C1-H), 3.97 (t, 2H, J=8.7 Hz, C2"-H), 3.90 (s, 3H, $OCH_3$), 3.30–3.28 (m, 4H, C1'-$H_2$, C1"$H_2$, obscured by $H_2O$), 3.03 (m, 1H, C8a-H), 1.79 (m, 1H, C8-H), 1.62 (m, 1H, C8-H); IR (neat) $v_{max}$ 3354, 2923, 1703, 1605, 1497, 1441, 1374, 1328, 1256, 1200 $cm^{-1}$; ESIMS m/z 656 ($M^+$+H, $C_{36}H_{29}N_7O_6$ requires 656).

(+)-30: $[α]_D^{25}$+54 (c 0.07, DMF).

ent-(−)-30: $[α]_D^{25}$−57 (c 0.07, DMF).

6-[7-Methoxycarbonyl-1,2-dihydro-3H-pyrrolo[3,2-e]indol-3-yl)carbonyl]-2-[(5,6,7-trimethoxyindol-2-yl)carbonyl]-1,2,8,8a-tetrahydrocyclopropa[c]-pyrrolo[3,2-e]indol-4-one (31, CDPI-DSA-TMI).

A suspension of NaH (0.4 mg, 60%, 9.5 μmol, 5.0 equiv) in DMF (50 μL) at 0° C. under Ar was treated with a solution of 29 (1.3 mg, 1.9 μmol, 1.0 equiv) in DMF (150 μL), and the reaction mixture was stirred for 30 min at 0° C. The mixture was concentrated under reduced pressure and subjected to chromatography (0.5×6.0 cm $SiO_2$, 12% DMF-toluene) to afford 31 (0.8 mg, 67%) as a yellow solid: $^1$H NMR (DMSO-$d_6$, 400 MHz) δ 12.01 (s, 1H, NH), 11.58 (s, 1H, NH), 8.10 (br s, 1H, C4'-H), 7.30 (d, 1H, J=9.0 Hz, C5'-H), 7.11 (s, 1H), 7.04 (s, 1H), 6.91 (s, 1H), 6.70 (s, 1H), 6.45 (s, 1H), 4.48–4.42 (m, 3H, C2'-$H_2$, C1-H), 4.28 (d, 1H, J=10.1 Hz, C1-H), 3.90 (s, 3H, $OCH_3$), 3.87 (s, 3H, $OCH_3$), 3.80 (s, 3H, $OCH_3$), 3.79 (s, 3H, $OCH_3$), 3.32 (m, 2H, C1'-$H_2$, obscured by $H_2O$), 3.00–2.98 (m,1H, C8a-H), 1.83–1.82 (m, 1H, C8-H), 1.68–1.67 (m, 1H, C8-H); IR (neat) $v_{max}$ 3303, 2923, 1703, 1646, 1615, 1441, 1374, 1303, 1251, 1200 $cm^{31\ 1}$; ESIMS m/z 662 ($M^+$+H, $C_{36}H_{31}N_5O_8$ requires 662).

(+)-31: $[α]_D^{25}$+49 (c 0.03, DMF).

ent-(−)-31: $[α]_D^{25}$−46 (c 0.05, DMF).

Preparation of 10:

5-[(tert-Butyloxycarbonyl)amino]indol-2-carboxylic Acid.

A solution of N—BOC-5-amino-2-(methoxycarbonyl)indole (57 mg, 0.2 mmol, 1.0 equiv) in THF—$CH_3OH$—$H_2O$ (2.4 mL) was treated with aqueous 1 N LiOH (0.24 mL, 0.24 mmol, 1.2 equiv). The reaction mixture was warmed at 60° C. for 2 h. The solvent was concentrated under a $N_2$ stream and $H_2O$ (3 mL) was added. This solution was treated with 10% aqueous HCl until the mixture was acidic. The insoluble solid was collected by centrifugation and washed with $H_2O$ (2×3 mL). Drying the solid afforded the title compound (53 mg, 96%) as a white solid: mp 235–250° C. (decomp.); $^1$H NMR (acetone-$d_6$, 400 MHz) δ 10.74 (br s, 1H, COOH), 8.26 (br s, 1H, NH), 7.95 (br s, 1H, NH), 7.43 (d, 1H, J=8.9 Hz, C6-H), 7.42 (s, 1H, C3-H), 7.39 (dd, 1H, J=8.9, 1.9 Hz, C7-H), 7.13 (dd, 1H, J=2.1, 0.8 Hz, C4-H), 1.49 (s, 9H, C($CH_3$)$_3$); IR (neat) $v_{max}$ 3351, 1698, 1536, 1236, 1177 $cm^{-1}$; FABHRMS (NBA-NaI) m/z 299.1003 ($M^+$+Na, $C_{14}H_{16}N_2O_4$ requires 299.1008).

N-[(2-Methoxycarbonyl)indol-5-yl]-5-[(tert-butyloxycarbonyl)amino]indole-2-carboxamide.

A solution of the carboxylic acid above (44 mg, 0.16 mmol, 1.0 equiv) and 5-amino-2-(methoxycarbonyl)indole (30 mg, 0.16 mmol, 1 equiv) in 33% DMF-THF (3 mL) was treated with EDCI (61 mg, 0.32 mmol, 2.0 equiv). The resulting reaction mixture was stirred for 15 h at 25° C. The mixture was concentrated under reduced pressure, and the residual solid was slurried in 3 mL of $H_2O$ containing 3 drops of 10% aqueous HCl. The solid was collected by centrifugation and then washed with $H_2O$ (3×3 mL). Chromatography (1×12 cm $SiO_2$, 50% EtOAc-hexane) afforded the title compound (61 mg, 85%) as a tan solid: mp 255–256° C.; $^1$H NMR (acetone$d_6$, 400 MHz) δ 10.95 (s, 1H, NH), 10.91 (s, 1H, NH), 9.67 (s, 1H, NH), 8.30 (s, 1H, NH), 8.24 (s, 1H), 7.94 (s, 1H), 7.69 (dd, 1H, J=8.9, 2.0 Hz, C7'-H), 7.51 (d, 1H, J=8.9 Hz), 7.47 (d, 1H, J=8.8 Hz), 7.33 (dd, 1H, J=8.8, 2.0 Hz, C7-H), 7.28 (d, 1H, J=0.5 Hz), 7.17 (dd, 1H, J=2.2, 0.8 Hz, C4-H), 3.88 (s, 3H, $OCH_3$), 1.49 (s, 9H, C($CH_3$)$_3$); IR (neat) $v_{max}$ 3302, 1698, 1643, 1536, 1477, 1437, 1364, 1295, 1236, 1157 $cm^{-1}$; FABHRMS (NBA-NaI) m/z 449.1838 ($M^+$+H, $C_{24}H_{24}N_4O_5$ requires 449.1825).

N-[2-(Methoxycarbonyl)indol-5-yl]-5-aminoindole-2-carboxamide (10).

A solution of the above compound (30 mg, 0.07 mmol) in trifluoroacetic acid (2.6 mL) was stirred for 45 min at 25° C. under Ar. The reaction mixture was concentrated, and the residual solid was slurried in 5% aqueous $NaHCO_3$ solution (3 mL). The insoluble solid was collected by centrifugation and washed with $H_2O$ (3×3 mL). Drying the solid in vacuo afforded 10 (21 mg, 91%) as a tan solid: mp>350° C.; $^1$H NMR (acetone-$d_6$, 400 MHz) δ 10.90 (br s, 1H, NH), 10.53 (br s, 1H, NH), 9.43 (br s, 1H, NH), 8.27 (d, 1H, J=1.9 Hz), 7.65 (dd, 1H, J=8.8, 2.0 Hz, C6'-H), 7.50 (d, 1H, J=8.9 Hz, C7'-H, 7.31 (d, 1H, J=C7-H), 7.16 (s, 1H), 7.05 (s, 1H), 6.83 (s, 1H), 6.75 (dd, 1H, J=8.6, 2.1 Hz, C6-H), 4.23 (br s, 2H, $NH_2$), 3.88 (s, 3H, $OCH_3$); IR (neat) $v_{max}$ 3262, 1697, 1533, 1441, 1236 $cm^{-1}$; FABHRMS (NBA-NaI) m/z 349.1313 ($M^+$+H, $C_{19}H_{16}N_4O_3$ requires 349.1301).

Resolution of N—BOC-DSA (39).

2-Propanol and hexane (Fisher, HPLC grade) were filtered through a Millipore HV filter (pore size=0.45 μm) and degassed by stirring under vacuum. A Waters Prep LC 4000 HPLC system equipped with a Diacel ChiralCel OD column (2×25 cm, 10 μm) was equilibrated with 30% 2-propanol-hexane at a flow rate of 7 mL/min. (±)-N—BOC-DSA (39)[17] was dissolved in $CH_3OH$ (20 mg/mL) and 0.5–1.0 mL (10–20 mg) aliquots were injected at 20–25 min intervals. The effluent was monitored at 254 nm, and the fractions containing resolved 40 were collected: natural (+)-39 ($t_R$= 19.5 min) and ent-(−)-36 ($t_R$=23.5 min), α=1.24.

General Procedure for the Preparation of 49–51 and 57–59:

Methyl 3-[[5-[((1H-Indol-2-yl)carbonyl)amino]-1H-indol-2-yl]carbonyl]-1-(chloromethyl)-5-hydroxy-1,2-dihydro-3H-pyrrolo[3,2-e]indole-7-carboxylate (59).

A solution of 36 (2.0 mg, 5.25 μmol) in 4 N HCl-EtOAc (0.25 mL) was stirred for 20 min at 25° C. The reaction mixture was concentrated to afford 38 as a gray powder. The hydrochloride salt was taken up in DMF (0.12 mL) and treated sequentially with EDCI (3.5 mg, 15.75 μmol, 3.3 equiv) and indole$_2$ (1.9 mg, 6.04 μmol, 1.1 equiv). The reaction mixture was stirred for 12 h at 25° C. before the solvent was removed under reduced pressure. The residual solid was slurried in 0.1 mL $H_2O$ and the solid was collected by centrifugation. Chromatography (1×5 cm $SiO_2$, 20% DMF-toluene) afforded 59 (2.5 mg, 81%) as a gray solid: mp>230° C.; $^1$H NMR (DMSO-$d_6$, 400 MHz) δ 11.73 (d, 1H, J=1.2 Hz, NH), 11.68 (d, 1H, J=1.6 Hz, NH), 11.65 (s, 1H, NH), 10.61 (s, 1H, NH), 9.83 (s, 1H, OH), 8.20 (d, 1H, J=1.6 Hz), 7.82 (br s, 1H), 7.67 (d, 1H, J=7.9 Hz), 7.55 (dd, 1H, J=8.8, 1.8 Hz), 7.48 (s, 1H), 7.46 (s, 1H), 7.42 (s, 1H), 7.29 (1H, J=2.0 Hz), 7.21 (dt, 1H, J=8.2, 1.2 Hz), 7.15 (d, 1H, J=1.4 Hz), 7.06 (dt, 1H, J=8.0, 0.8 Hz), 4.77 (t, 1H, J=10.6 Hz, C2-H), 4.45 (dd, 1H, J=10.9, 3.9 Hz, C2-H), 4.15–4.05 (m, 2H), 3.98 (dd, 1H, J=7.0, 3.9 Hz), 3.87 (s, 3H, OCH$_3$); IR (neat) $v_{max}$ 3393, 2966, 2916, 1711, 1693, 1662, 1646, 1631, 1612, 1553, 1537, 1517, 1485, 1234, 1134 cm$^{-1}$; FABHRMS (NBA-NaI) m/z 582.1540 (M$^+$+H, C$_{31}$H$_{24}$N$_5$O$_5$Cl requires 582.1544).

(1S)-59: $[\alpha]_D^{23}$+27 (c 0.15, DMF).
ent-(1R)-59: $[\alpha]_D^{23}$–29 (c 0.10, DMF).

General Procedure for the Preparation of 53–56 and 60–62: Methyl 2-[[5-[((1H-Indol-2-yl)carbonyl)amino]-1H-indol-2-yl]carbonyl]-1,2,8,8a-tetrahydrocyclopropa[c]-pyrrolo[3,2-e]indol-4-one-6-carboxylate (62, DSA-indole$_2$).

A portion of NaH (0.4 mg, 60%, 10.3 μmol, 3 equiv) at 0° C. under Ar was treated with a solution of 59 (2.0 mg, 3.4 μmol, 1.0 equiv) in DMF (0.25 mL), and the reaction mixture was stirred for 90 min at 0° C. The reaction mixture was directly subjected to flash chromatography (1×5 cm SiO$_2$, 15% DMF-toluene) to afford 62 (1.6 mg, 85%) as a pale yellow solid: mp>230° C.; $^1$H NMR (DMSO-d$_6$, 400 MHz) δ 12.64 (s, 1H, NH), 11.81 (d, 1H, J=1.6 Hz, NH), 11.72 (d, 1H, J=1.2 Hz, NH), 10.18 (s, 1H, OH), 8.20 (d, 1H, J=1.5 Hz), 7.66 (d, 1H, J=8.0 Hz), 7.59 (dd, 1H, J=8.9, 2.0 Hz), 7.47 (s, 1H), 7.45 (s, 1H), 7.41 (d, 1H, J=1.4 Hz), 7.22 (d, 1H, J=2.2 Hz), 7.20 (dd, 1H, J=8.2, 1.1 Hz), 7.06 (dt, 1H, J=7.5, 0.7 Hz), 6.80 (s, 1H), 6.79 (d, 1H, J=7.1 Hz), 4.58 (dd, 1H, J=10.5, 5.1 Hz, C1-H), 4.44 (d, 1H, J=10.5 Hz, C1-H), 3.79 (s, 3H, OCH$_3$), 3.05 (m, 1H, C8a-H), 1.78 (dd, 1H, J=7.7, 3.8 Hz, C8-H), 1.60 (t, 1H, J=4.5 Hz, C8-H); IR (neat)$v_{max}$ 3317, 2953, 2921, 2853, 1712, 1658, 1649, 1642, 1592, 1554, 1515, 1390, 1310, 1260 cm$^{-1}$; FABHRMS (NBA) m/z 546.1789(M$^+$+H, C$_{31}$H$_{23}$N$_5$O$_5$ requires 546.1777).

(+)-62: $[\alpha]_D^{23}$+65 (c 0.16, DMF).
ent-(–)-62: $[\alpha]_D^{23}$–69 (c 0.19, DMF).

Methyl 3-Acetyl-1-(chloromethyl)-5-hydroxy-1,2-dihydro-3H-pyrrolo[3,2-e]indole-7-carboxylate (42).

A solution of N—BOC-DSA (39, 2.2 mg, 6.4 μmol, 1.0 equiv) in 4 N HCl-EtOAc (0.3 mL) was stirred for 30 min at 25° C. The reaction mixture was concentrated to afford 38 as a gray solid. The hydrochloride salt was taken up in THF (80 μL) and treated sequentially with NaHCO$_3$ (1.6 mg, 19.2 μmol, 3.0 equiv) and ClCOCH$_3$ (50 μL, 0.26 M in THF, 2.0 equiv) at 0° C. under Ar. The reaction mixture was stirred for 1 h at 25° C. and directly subjected to flash chromatography (0.5×5.0 cm SiO$_2$, 50–67% EtOAc-hexane gradient elution) to afford 42 (2.0 mg, 97%) as a white solid: $^1$H NMR (acetone-d$_6$, 400 MHz) δ 10.69 (br s, 1H), 8.85 (br s, 1H), 7.93 (s, 1H), 7.21 (s, 1H), 4.35 (dd, 1H, J=10.5, 9.8 Hz), 4.15–4.04 (m, 3H), 3.88 (s, 3H), 3.80 (dd, 1H, J=10.3, 8.1 Hz), 2.18 (s, 3H); IR (neat) $v_{max}$ 3333, 2964, 1697, 1615, 1415, 1256, 1164 cm$^{-1}$; FABHRMS (NBA) m/z 323.0807 (M$^+$+H, C$_{15}$H$_{15}$N$_2$O$_4$Cl requires 323.0799).

(1S)-42: $[\alpha]_D^{25}$–48 (c 0.1, CH$_3$OH).
ent-(1R)-42: $[\alpha]_D^{25}$+44 (c 0.08, CH$_3$OH).

Methyl 2-Acetyl-1,2,8,8a-tetrahydrocyclopropa[c]pyrrolo[3,2-e]indol-4-one-6-carboxylate (40, N—Ac-DSA).

A suspension of NaH (0.7 mg, 60%, 18.6 μmol, 3.0 equiv) in THF (0.12 mL) at 0° C. under Ar was treated with a solution of 42 (2.0 mg, 6.2 μmol, 1.0 equiv) in 50% THF-DMF (0.3 mL), and the reaction mixture was stirred for 30 min at 0° C. Hexane (0.2 mL) was added, and the mixture was subjected to flash chromatography (0.5×6.0 cm SiO$_2$, 83–100% EtOAc-hexane gradient elution) to afford 40 (1.3 mg, 73%) as a white solid: $^1$H NMR (acetone-d$_6$, 400 MHz) δ 11.28 (br s, 1H, NH), 7.18 (br s, 1H, C3-H), 6.69 (s, 1H, C7-H), 4.18 (m, 2H, C1-H$_2$), 3.82 (s,3H, OCH$_3$), 2.93–2.91 (m, 1H, C8a-H), 2.21 (s, 3H, CH$_3$), 1.72 (dd, 1H, J=7.7, 3.9 Hz, C8-H), 1.44 (t, 1H, J=4.5 Hz, C8-H); IR (neat) $v_{max}$ 3214, 2953, 1712, 1690, 1518, 1393, 1267, 1213 cm$^{-1}$; FABHRMS (NBA) m/z 287.1043 (M$^+$+H, C$_{15}$H$_{15}$N$_2$O$_4$ requires 287.1032).

(+)-40: $[\alpha]_D^{25}$+148 (c 0.05, CH$_3$OH).
ent-(–)-40: $[\alpha]_D^{25}$–145 (c 0.04, CH$_3$OH).

Methyl 1-(Chloromethyl)-5-hydroxy-3-(methoxycarbonyl)-1,2-dihydro-3H-pyrrolo[3,2-e]indole-7-carboxylate (43).

A solution of N—BOC-DSA (39, 2.2 mg, 6.4 μmol, 1.0 equiv) in 4 N HCl-EtOAc (0.3 mL) was stirred for 30 min at 25° C. The reaction mixture was concentrated to afford 38 as a gray solid. The hydrochloride salt was taken up in THF (0.2 mL) and treated sequentially with NaHCO$_3$ (1.6 mg, 19.2 μmol, 3.0 equiv) and ClCO$_2$CH$_3$ (50 μL, 0.26 M in THF, 2.0 equiv) at 0° C. under Ar. The reaction mixture was stirred at 25° C. for 1 h, concentrated and subjected to flash chromatography (0.5×5.0 cm SiO$_2$, 50% EtOAc-hexane) to afford 43 (1.0 mg, 46%) as a white solid: $^1$H NMR (acetone-d$_6$, 400 MHz) δ 10.63 (br s, 1H), 8.23 (br s, 1H), 7.59 (br s, 1H), 7.19 (s, 1H), 4.19 (dd, 1H, J=11.4, 9.5 Hz), 4.09–3.98 (m, 3H), 3.87 (s, 3H), 3.78 (dd, 1H, J=10.8, 8.2 Hz), 3.76 (s, 3H); IR (neat) $v_{max}$ 3313, 2954, 1687, 1456, 1344, 1251, 1154 cm$^{-1}$; FABHRMS (NBA) m/z 338.0735 (M$^+$, C$_{15}$H$_{15}$N$_2$O$_5$Cl requires 338.0669).

(1S)-43: $[\alpha]_D^{25}$–25 (c 0.03, CH$_3$OH).
ent-(1R)-43: $[\alpha]_D^{25}$+27 (c 0.03, CH$_3$OH).

Methyl 2-(Methoxycarbonyl)-1,2,8,8a-tetrahydrocyclopropa[c]pyrrolo[3,2-e]indol-4-one-6-carboxylate (41, N—CO$_2$Me-DSA).

A suspension of NaH (0.3 mg, 60%, 8.4 μmol, 3.0 equiv) in THF (80 μL) at 0° C. under Ar was treated with a solution of 43 (1.0 mg, 2.8 μmol, 1.0 equiv) in 50% THF-DMF (160 μL), and the reaction mixture was stirred for 30 min at 0° C. Hexane (0.2 mL) was added, and the mixture was subjected to flash chromatography (0.5×6.5 cm SiO$_2$, 50–67% EtOAc-hexane gradient elution) to afford 41 (0.8 mg, 92%) as a white solid: $^1$H NMR (acetone-d$_6$, 400 MHz) δ 6.69 (s, 2H, C3-H and C7-H), 4.08–4.05 (m, 2H, C1-H$_2$), 3.82 (s, 3H, OCH$_3$), 3.79 (s, 3H, OCH$_3$) 2.95–2.90 (m, 1H, C8a-H), 1.71 (dd, 1H, J=7.7, 4.0 Hz, C8-H), 1.45 (t, 1H, J=4.5 Hz, C8-H); IR (neat) $v_{max}$ 3405, 3262, 2923, 1718, 1595, 1441, 1390, 1267 cm$^{-1}$; FABHRMS (NBA) m/z 303.0987 (M$^+$+H, C$_{15}$H$_{14}$N$_2$O$_5$ requires 303.0981).

(+)-41: $[\alpha]_D^{25}$+130 (c 0.05, CH$_3$OH).
ent-(–)-41: $[\alpha]_D^{25}$–130 (c 0.04, CH$_3$OH).

General Procedure for the Preparation of 49–52: Methyl 3-[(5-Methoxyindol-2-yl)carbonyl]-1-(chloromethyl)-5-hydroxy-1,2-dihydro-3H-pyrrolo[3,2-e]indole-7-carboxylate (50).

A solution of N—BOC-DSA (39, 2.1 mg, 6.1 μmol, 1.0 equiv) in 4 N HCl-EtOAc (0.3 mL) was stirred for 30 min at 25° C. The reaction mixture was concentrated to afford 38 as a gray solid. The hydrochloride salt was taken up in DMF (0.11 mL) and treated sequentially with 5-methoxyindole-2-carboxylic acid (1.3 mg, 6.7 μmol, 1.1 equiv) and EDCI (3.5 mg, 18.3 μmol, 3.0 equiv). The reaction mixture was stirred for 15 h at 25° C. before the solvent was concentrated under reduced pressure. Chromatography (0.5×6.0 cm SiO$_2$, 3% CH$_3$OH—CH$_2$Cl$_2$) afforded 50 (2.0 mg, 70%) as a pale yellow solid: $^1$H NMR (acetone-d$_6$, 400 MHz) δ 10.73 (s, 1H, NH), 10.67 (s, 1H, NH), 8.87 (br s, 1H, OH), 7.99 (s, 1H, C4-H), 7.47 (d, 1H, J=8.9 Hz, C7'-H), 7.29 (s, 1H, C8-H), 7.17 (d, 1H, J=2.4 Hz, C4'-H), 7.10 (s, 1H, C3'-H), 6.92 (dd, 1H, J=8.9, 2.4 Hz, C6'-H), 4.81 (t, 1H, J=10.8 Hz, C2-H), 4.63 (dd, 1H, J=10.8, 3.9 Hz, C2-H), 4.23–4.18 (m, 1H, C1-H), 4.16 (dd, 1H, J=10.5, 2.8 Hz, CBHCl), 3.92 (dd, 1H, J=10.6, 7.7 Hz, CHHCl), 3.89 (s, 3H, OCH$_3$), 3.82 (s, 3H, OCH$_3$); IR (neat) $v_{max}$ 3322, 2943, 1699, 1602, 1519, 1432, 1218 cm$^{-1}$; FABHRMS (NBA-CsI) m/z 586.0160 (M$^+$+Cs, C$_{23}$H$_{20}$N$_3$O$_5$Cl requires 586.0146).

(+)-50: [α]$_D^{25}$+10 (c 0.11, THF).

ent-(−)-50: [α]$_D^{25}$11 (c 0.10, THF).

Methyl 3-[(Indol-2-yl)carbonyl]-1-(chloromethyl)-5-hydroxy-1,2-dihydro-3H-pyrrolo[3,2-e]indole-7-carboxylate (49):

(78%) as a gray solid: $^1$H NMR (acetone-d$_6$, 400 MHz) δ 10.80 (s, 1H, NH), 10.76 (s, 1H, NH), 8.92 (br s, 1H, OH), 7.95 (br s, 1H, C4-H), 7.71 (d, 1H, J=7.9 Hz, C4'-H), 7.58 (d, 1H, J=8.3 Hz, C7'-H), 7.29 (s, 1H, C8-H), 7.26 (dt, 1H, J=7.1, 1.1 Hz, C6'-H), 7.19 (s, 1H, C3'-H), 7.10 (dt, 1H, J=7.1, 0.8 Hz, C5'-H), 4.84 (t, 1H, J=10.6 Hz, C2-H), 4.65 (dd, 1H, J=10.8, 4.0 Hz, C2-H), 4.23–4.19 (m, 1H, C1-H), 4.16 (dd, 1H, J=10.8, 3.3 Hz, CHHCl), 3.93 (dd, 1H, J=10.8, 7.8 Hz, CHHCl), 3.89 (s, 3H, OCH$_3$); IR (neat) $v_{max}$ 3321, 2932, 1707, 1599, 1436 cm$^{-1}$; FABHRMS (NBA-CsI) m/z 424.1076 (M$^+$+H, C$_{22}$H$_{18}$N$_3$O$_4$Cl requires 424.1064).

Methyl 3-[(6-Methoxyindol-2-yl)carbonyl]-1-(chloromethyl)-5-hydroxy-1,2-dihydro-3H-pyrrolo[3,2-e]indole-7-carboxylate (51):

(79%) as a pale yellow solid: $^1$H NMR (acetone-d$_6$, 400 MHz) δ 10.78 (br s, 1H, NH), 10.63 (s, 1H, NH), 8.95 (br s, 1H, OH), 8.01 (s, 1H, C4-H), 7.58 (d, 1H, J=8.7 Hz, C4'-H), 7.27 (s, 1H, C8-H), 7.12 (dd, 1H, J=2.1, 0.6 Hz, C3'-H), 7.06 (d, 1H, J=2.2 Hz, C7'-H), 6.76 (dd, 1H, J=8.7, 2.3 Hz, C5'-H), 4.80 (dd, 1H, J=10.8, 9.4 Hz, C2-H), 4.61 (dd, 1H, J=10.8, 4.0 Hz, C2-H), 4.23–4.14 (m, 2H, C1-H, CHHCl), 3.92 (dd, 1H, J=10.7, 7.7 Hz, CHHCl), 3.89 (s, 3H, OCH$_3$), 3.81 (s, 3H, OCH$_3$); IR (neat) $v_{max}$ 3272, 1708, 1610, 1513, 1436, 1303, 1221, 1159, 1013 cm$^{-1}$; FABHRMS (NBA-CsI) m/z 586.0160 (M$^+$+Cs, C$_{23}$H$_{20}$N$_3$O$_5$Cl requires 586.0146).

(1S)-51: [α]$_D^{25}$−1.9 (c 0.13, THF).

ent-(1R)-51: [α]$_D^{25}$+2.3 (c 0.11, THF).

Methyl 3-[(7-Methoxyindol-2-yl)carbonyl]-1-(chloromethyl)-5-hydroxy-1,2-dihydro-3H-pyrrolo[3,2-e]indole-7-carboxylate (52):

(81%) as a white solid: $^1$H NMR (acetone-d$_6$, 400 MHz) δ 11.22 (br s, 1H, NH), 10.47 (br s, 1H, NH), 9.45 (br s, 1H, OH), 7.91 (br s, 1H, C4-H), 7.28 (d, 1H, J=8.0 Hz, C4'-H), 7.25 (s, 1H, C8-H), 7.12 (s, 1H, C3'-H), 7.02 (t, 1H, J=7.9 Hz, C5'-H), 6.78 (d, 1H, J=7.7 Hz, C6'-H), 4.77 (dd, 1H, J=10.3, 9.8 Hz, C2-H), 4.57 (dd, 1H, J=10.8, 3.9 Hz, C2-H), 4.17–4.09 (m, 2H, C1-H, CHHCl), 3.97 (s, 3H, OCH$_3$), 3.93–3.88 (m, 1H, CHHCl), 3.91 (s, 3H, OCH$_3$); IR (neat) $v_{max}$ 3323, 2933, 1708, 1595, 1436, 1349, 1256, 1159 cm$^{-1}$; FABHRMS (NBA-CsI) m/z 586.0161 (M$^+$+Cs, C$_{23}$H$_{20}$N$_3$O$_5$Cl requires 586.0146).

(1S)-52: [α]$_D^{25}$−3.5 (c 0.13, THF).

ent-(1R)-52: [α]$_D^{25}$+2.7 (c 0.12, THF).

General Procedure for the Preparation of 53–56: Methyl 2-[(5-Methoxyindol-2-yl)carbonyl]-1,2,8,8a-tetrahydrocyclopropa[c]pyrrolo[3,2-e]indol-4-one-6-carboxylate (54).

A suspension of NaH (0.4 mg, 60%, 10.5 μmol, 3.0 equiv) in THF (0.12 mL) at 0° C. under Ar was treated with a solution of 50 (1.6 mg, 3.5 μmol, 1.0 equiv) in 50% THF-DMF (0.24 mL), and the reaction mixture was stirred for 30 min at 0° C. Hexane (0.2 mL) was added, and the mixture was subjected to flash chromatography (0.5×7.0 cm SiO$_2$, 2–3.5% CH$_3$OH—CH$_2$Cl$_2$ gradient elution) to afford 54 (1.4 mg, 96%) as a pale yellow solid: $^1$H NMR (acetone-d$_6$, 400 MHz) δ 11.32 (s, 1H, NH), 10.79 (s, 1H, NH), 7.46 (d, 1H, J=8.9 Hz, C7'-H), 7.13 (s, 1H, C3'-H), 7.13 (s, 1H, C4'-H), 6.96 (dd, 1H, J=7.1, 1.9 Hz, C6'-H), 6.91 (s, 1H, C3-H), 6.75 (s, 1H, C7-H), 4.61 (dd, 1H, J=10.3, 5.0 Hz, C1-H), 4.53 (d, 1H, J=10.3 Hz, C1-H), 3.84 (s, 3H, OCH$_3$), 3.81 (s, 3H, OCH$_3$), 3.05 (dt, 1H, J=7.7, 3.9 Hz, C8a-H), 1.81 (dd, 1H, J=7.7, 4.0 Hz, C8-H), 1.62 (t, 1H, J=4.5 Hz, C8-H); IR (neat) $v_{max}$ 3284, 2934, 1713, 1633, 1607, 1512, 1389, 1257 cm$^{-1}$; FABHRMS (NBA-CsI) m/z 550.0361 (M$^+$+Cs, C$_{23}$H$_{19}$N$_3$O$_5$ requires 550.0379).

(+)-54: [α]$_D^{25}$+158 (c 0.06, THF).

ent-(−)-54: [α]$_D^{25}$−168 (c 0.04, THF).

Methyl 2-[(Indol-2-yl)carbonyl]-1,2,8,8a-tetrahydrocyclopropa[c]pyrrolo[3,2-e]indol-4-one-6-carboxylate (53, DSA-indole$_1$):

(88%) as a pale yellow solid: $^1$H NMR (acetone-d$_6$, 400 MHz) δ 10.92 (br s, 1H, NH), 7.69 (dd, 1H, J=8.0, 0.8 Hz, C4'-H), 7.57 (dd, 1H, J=8.3,0.9 Hz, C7'-H), 7.29 (dt, 1H, J=8.2, 1.1 Hz, C6'-H), 7.23 (s, 1H, C3'-H), 7.11 (dt, 1H, J=8.0, 0.9 Hz, C5'-H), 6.93 (s, 1H, C3-H), 6.76 (s, 1H, C7-H), 4.64 (dd, 1H, J=10.3, 5.0 Hz, C1-H), 4.56 (d, 1H, J=10.3 Hz, C1-H), 3.84 (s, 3H, OCH$_3$), 3.08–3.04 (m, 1H, C8a-H), 1.81 (dd, 1H, J=7.7, 4.0 Hz, C8-H), 1.63 (t, 1H, J=4.5 Hz, C8-H); IR (neat) $v_{max}$ 3303, 2923, 1708, 1641, 1610, 1390, 1262 cm$^{-1}$; FABHRMS (NBA-NaI) m/z 388.1310 (M$^+$+H, C$_{22}$H$_{17}$N$_3$O$_4$ requires 388.1297).

(+)-53: [α]$_D^{25}$+181 (c 0.04, CH$_3$OH).

ent-(−)-53: [α]$_D^{25}$−176 (c 0.05, CH$_3$OH).

Methyl 2-[(6-Methoxyindol-2-yl)carbonyl]-1,2,8,8a-tetrahydrocyclopropa[c]-pyrrolo[3,2-e]indol-4-one-6-carboxylate (55):

(87%) as a pale yellow solid: $^1$H NMR (acetone-d$_6$, 400 MHz) δ 11.34 (br s, 1H, NH), 10.71 (br s, 1H, NH), 7.56 (d, 1H, J=8.7 Hz, C4'-H), 7.17 (s, 1H, C3'-H), 7.04 (d, 1H, J=2.1 Hz, C7'-H), 6.96 (s, 1H, C3-H), 6.77 (dd, 1H, J=8.8, 2.3 Hz, C5'-H), 6.75 (s, 1H, C7-H), 4.61 (dd, 1H, J=10.2, 4.9 Hz, C1-H), 4.53 (d, 1H, J=10.2 Hz, C1-H), 3.84 (s, 3H, OCH$_3$), 3.83 (s, 3H, OCH$_3$), 3.08–3.03 (m, 1H, C8a-H), 1.80 (dd, 1H, J=7.7, 4.0 Hz, C8-H), 1.61 (t, 1H, J=4.5 Hz, C8-H); IR (neat) $v_{max}$ 3261, 2954, 1713, 1634, 1505, 1386, 1260 cm$^{-1}$; FABHRMS (NBA) m/z 418.1403 (M$^+$+H, C$_{23}$H$_{19}$N$_3$O$_5$ requires 418.1411).

(+)-55: [α]$_D^{25}$+146 (c 0.035, THF).

ent-(−)-55: [α]$_D^{25}$−137 (c 0.075, THF).

Methyl 2-[(7-Methoxyindol-2-yl)carbonyl]-1,2,8,8a-tetrahydrocyclopropa[c]pyrrolo[3,2-e]indol-4-one-6-carboxylate (56):

(91%) as a pale yellow solid: $^1$H NMR (acetone-d$_6$, 400 MHz) δ 11.21 (br s, 1H, NH), 10.46 (br s, 1H, NH), 7.25 (d, 1H, J=8.1 Hz, C4'-H), 7.17 (s, 1H, C3'-H), 7.03 (t, 1H, J=7.9 Hz, C5'-H), 6.80 (d, 1H, J=7.6 Hz, C6'-H), 6.80 (s, 1H, C3-H), 6.75 (s, 1H, C7-H), 4.59 (dd, 1H, J=10.4, 5.0 Hz, C1-H), 4.49 (d, 1H, J=10.4 Hz, C1-H), 3.95 (s, 3H, OCH$_3$), 3.84 (s, 3H, OCH$_3$), 3.06–3.02 (m, 1H, C8a-H), 1.82 (dd, 1H, J=7.6, 4.1 Hz, C8-H), 1.65 (t, 1H, J=4.5 Hz, C8-H); IR (neat) $v_{max}$ 3231, 2944, 1708, 1610, 1518, 1390, 1256 cm$^{-1}$; FABHRMS (NBA-CsI) m/z 550.0363 (M$^+$+Cs, C$_{23}$H$_{19}$N$_3$O$_5$ requires 550.0379).

(+)-56: [α]$_D^{25}$+166 (c 0.08, THF).

ent-(−)-56: [α]$_D^{25}$−172 (c 0.06, THF).

Methyl 3-[(3-Carbamoyl-1,2-dihydro-3H-pyrrolo[3,2-e]indol-7-yl)carbonyl]-1-(chloromethyl)-5-hydroxy-1,2-dihydro-3H-pyrrolo[3,2-e]indole-7-carboxylate (57):

Chromatography (1×5 cm SiO$_2$, 10% CH$_3$OH—CH$_2$Cl$_2$) afforded 57 (1.6 mg, 67%) as an off-white solid: mp>230°

C.: $^1$H NMR (DMSO-d$_6$, 400 MHz) δ 11.63 (br s, 1H, NH), 11.55 (br s, 1H, NH), 9.82 (br s, 1H, OH), 7.97 (d, 1H, J=8.9 Hz, C4'-H), 7.79 (br s, 1H), 7.28 (d, 1H, J=2.1 Hz), 7.21 (d, 1H, J=9.1 Hz, C5'-H), 6.93 (d, 1H, J=1.5 Hz), 6.11 (s, 2H, NH$_2$), 4.75 (t, 1H, J=10.2 Hz, C2-H), 4.41 (dd, 1H, J=11.0, 4.1 Hz, C2-H), 4.11–4.06 (m, 2H), 4.02–3.90 (m, 1H), 3.97 (t, 2H, J=9.2 Hz, C2'-H), 3.86 (s, 3H, OCH$_3$), 3.33–3.29 (m, 2H, C1'-H, obscured by H$_2$O); IR (neat) $v_{max}$ 3347, 2956, 2922, 2854, 1708, 1657, 1602, 1512, 1501, 1433, 1344, 1002 cm$^{-1}$; FABHRMS (NBA-CsI) m/z 507.1322 (M$^+$+H, C$_{25}$H$_{22}$N$_5$O$_5$Cl requires 507.1309).

(1S)-57: $[\alpha]_D^{23}$+13 (c 0.16, DMF).

ent-(1R)-57: $[\alpha]_D^{23}$−14 (c 0.2, DMF).

Methyl 3-[(1,2-Dihydro-3-[(1,2-dihydro-3-carbamoyl-3H-pyrrolo[3,2-e]indol-7-yl)carbonyl]-3H-pyrrolo[3,2-e]indol-7-yl)carbonyl]-1-(chloromethyl)-5-hydroxy-1,2-dihydro-3H-pyrrolo[3,2-e]indole-7-carboxylate (58):

Chromatography (0.5×5 cm SiO$_2$, 30% DMF-toluene) afforded 58 (2.4 mg, 67%) as a gray solid: mp>230° C.; $^1$H NMR (DMSO-d$_6$, 400 MHz) δ 11.75 (d, 1H, J=2.0 Hz, NH), 11.64 (s, 1H, NH), 11.55 (d, 1H, J=1.6 Hz, NH), 9.83 (s, 1H, OH), 8.26 (br s, 1H, C4-H), 7.96 (d, 1H, J=8.9 Hz, C4'-H), 7.81 (br s, 1H), 7.36 (d, 1H, J=9.2 Hz, C5"-H), 7.29 (d, 1H, J=2.1 Hz, C8-H), 7.22 (d, 1H, J=8.4 Hz, C5'-H), 7.10 (s, 1H, C8"-H), 6.96 (s, 1H, C8'-H), 6.10 (s, 2H, NH$_2$), 4.78 (t, 1H, J=9.8 Hz, C2-H), 4.65 (t, 2H, J=8.2 Hz, C2'-H), 4.45 (dd, 1H, J=11.0, 3.9 Hz, C2-H), 4.18–3.95 (m, 3H), 3.86 (s, 3H, OCH$_3$), 3.46 (dd, 2H, J=11.6, 8.3 Hz), 3.40–3.20 (m, 4H, C1'-H and C1"-H, obscured by H$_2$O); IR (neat) $v_{max}$ 3321, 2950, 2924, 2852, 1710, 1657, 1608, 1502, 1432, 1005 cm$^{-1}$; FABHRMS (NBA) m/z 691.1978 (M$^+$+H, C$_{36}$H$_{30}$N$_7$O$_6$Cl requires 691.1946).

(1S)-58: $[\alpha]_D^{23}$+6 (c 0.2 DMF).

ent-(1R)-58: $[\alpha]_D^{23}$−8 (c 0.1 DMF).

Methyl 3-[(3-Carbamoyl-1,2-dihydro-3H-pyrrolo[3,2-e]indol-7-yl)carbonyl]-1,2,8,8a-tetrahydrocyclopropa[c]pyrrolo[3,2e]indol-4-one-6-carboxylate (60, DSA-CDPI$_1$):

Chromatography (1×5 cm SiO$_2$, 15% DMF-toluene) afforded 60 (71–98%) as a pale yellow solid: mp>245° C.; $^1$H NMR (DMSO-d$_6$, 400 MHz) δ 12.64 (br s, 1H, NH), 11.69 (d, 1H, J=1.6 Hz, NH), 8.00 (d, 1H, J=8.9 Hz, C4'-H), 7.20 (d, 1H, J=8.9 Hz, C5'-H), 7.01 (d, 1H, J=1.6 Hz), 6.80 (s, 1H), 6.74 (s, 1H), 6.12 (br s, 2H, NH$_2$), 4.55 (dd, 1H, J=10.5, 5.1 Hz, C1-H), 4.41 (d, 1H, J=10.5 Hz, C1-H), 3.96 (t, 2H, J=8.8 Hz, C2'-H), 3.78 (s, 3H, OCH$_3$), 3.34–3.22 (m, 2H, C1'-H, obscured by H$_2$O), 3.08–3.00 (m, 1H, C8a-H), 1.77 (dd, 1H, J=7.7, 3.8 Hz, C8-H), 1.59 (t, 1H, J=4.4 Hz, C8-H); IR (neat) vmax 3352, 2921, 2849, 1707, 1657, 1602, 1502, 1422, 1390, 1265, 1001 cm$^{-1}$; FABHRMS (NBA) m/z 472.1629 (M$^+$+H, C$_{25}$H$_{21}$N$_5$O$_5$ requires 472.1621).

(+)-60: $[\alpha]_D^{23}$+71 (c 0.1, DMF).

ent-(−)-60: $[\alpha]_D^{23}$−67 (c 0.05, DMF).

Methyl 2-[(1,2-Dihydro-3-[(1,2-dihydro-3-carbamoyl-3H-pyrrolo[3,2-e]indol-7-yl)carbonyl-3H-pyrrolo[3,2e]indol-7-yl)carbonyl]-1,2,8,8a-tetrahydrocyclopropa[c]-pyrrolo[3,2e]indol-4-one-6-carboxylate (61, DSA-CDPI$_2$):

Chromatography (1×5 cm SiO$_2$, 30% DMF-toluene) afforded 61 (87–94%) as a pale yellow solid: mp>230° C.; $^1$H NMR (DMSO-d$_6$, 400 MHz) δ 12.63 (s, 1H, NH), 11.87 (s, 1H, NH), 11.55 (s, 1H, NH), 8.27 (br s, 1H, C4'-H), 7.97 (d, 1H, J=8.9 Hz, C4"-H), 7.35 (d, 1H, J=8.8 Hz, C5"-H), 7.21 (d, 1H, J=8.8 Hz, C5'-H), 7.17 (s, 1H, C8"-H), 6.95 (s, 1H, C8'-H), 6.80 (s, 1H), 6.74 (s, 1H), 6.09 (s, 2H, NH$_2$), 4.64 (t, 2H, J=8.6 Hz, C2'-H), 4.58 (dd, 1H, J=10.2, 5.0 Hz, C1-H), 4.47 (d, 1H, J=10.6 Hz, C1-H), 3.96 (t, 2H, J=8.8 Hz, C2"-H), 3.79 (s, 3H, OCH$_3$), 3.40–3.20 (m, 2H, C1"-H), 3.39 (t, 2H, J=8.8 Hz, C1'-H), 3.10–3.00 (m, 1H, C8a-H), 1.79 (dd, 1H, J=7.7, 3.7 Hz, C8-H), 1.61 (t, 1H, J=4.5 Hz, C8-H); IR (neat) $v_{max}$ 3371, 2926, 1710, 1657, 1608, 1501, 1430, 1390, 1265, 1056 cm$^{31\ 1}$; FABHRMS (NBA) m/z 656.2268 (M$^+$+H, C$_{36}$H$_{29}$N$_7$O$_6$ requires 656.2258).

(+)-61: $[\alpha]_D^{23}$+43 (c 0.04, DMF).

ent-(−)-61: $[\alpha]_D^{23}$−39 (c 0.2, DMF).

Acid-Catalyzed Addition of CH$_3$OH to (±)-N—BOC-DSA (39).

25° C.: A solution of (±)-N—BOC-DSA (39, 2.3 mg, 6.6 μmol) in 0.66 mL of CH$_3$OH was treated with 0.8 μmol of CF$_3$SO$_3$H dissolved in THF (17 μL) and the mixture was stirred for 1 h at 25° C. under Ar. NaHCO$_3$ (2 mg) was added followed by H$_2$O (2 mL). The mixture was extracted with EtOAc (4×1 mL) and the combined organic layers were dried (Na$_2$SO$_4$) and concentrated. Chromatography (SiO$_2$, 20% EtOAc-hexane) afforded 66 (1.9 mg, 75%) and 67 (0.45 mg, 18%).

0° C.: A solution of (±)-N—BOC-DSA (39, 1.5 mg, 4.4 μmol) in 0.44 mL of CH$_3$OH was treated with 0.5 μmol of CF$_3$SO$_3$H dissolved in THF (3 μL) and the mixture stirred for 3 h at 0° C. under Ar. NaHCO$_3$ (2 mg) was added followed by H$_2$O (2 mL). The mixture was extracted with EtOAc (4×1 mL) and the combined organic layers were dried (Na$_2$SO$_4$) and concentrated. Chromatography (SiO$_2$, 20% EtOAc-hexane) afforded 66 (1.24 mg, 76%) and 67 (0.2 mg, 12%).

For methyl 3-((tert-butyloxy)carbonyl)-5-hydroxy-1-(methoxymethyl)-1,2-dihydro-3H-pyrrolo[3,2-e]indole-7-carboxylate (66): $^1$H NMR (acetone-d$_6$, 400 MHz) δ 10.47 (s, 1H, NH), 8.60 (s, 1H, OH), 7.61 (s, 1H), 7.11 (s, 1H), 4.06 (m, 2H, NCH$_2$), 3.87 (s, 3H, CO$_2$CH$_3$), 3.78 (d, 2H, J=4.4 Hz, CH$_2$OCH$_3$), 3.40 (m, 1H, ArCH, 3.34 (s, 3H, OCH$_3$), 1.53 (s, 9H, C(CH$_3$)$_3$); FABHRMS (NBA-NaI) m/z 399.1539 (M$^+$+Na, C$_{19}$H$_{24}$N$_2$O$_6$ requires 399.1532).

For methyl 6-((tert-butyloxy)carbonyl)-4-hydroxy-8-methoxy-6,7,8,9-tetrahydropyrrolo[3,2-ƒ]quinoline-2-carboxylate (67): $^1$H NMR (acetone-d$_6$, 400 MHz) δ 10.57 (s, 1H, NH), 8.51 (s, 1H, OH), 7.10 (s, 1H), 7.06 (s, 1H), 3.87 (s, 3H, CO$_2$CH$_3$), 3.83 (dd, 1H, J=12.6, 7.2 Hz, NCH), 3.78 (m, 1H, CHOCH$_3$), 3.71 (dd, 1H, J=12.6, 2.1 Hz, NCH), 3.42 (s, 3H, OCH$_3$), 3.21 (dd, 1H, J=17.2, 6.0 Hz, ArCH), 2.85 (dd, 1H, J=17.2, 4.0 Hz, ArCH), 1.49 (s, 9H, C(CH$_3$)$_3$); FABHRMS (NBA-NaI) m/z 399.1547 (M$^+$+Na, C$_{19}$H$_{24}$N$_2$O$_6$ requires 399.1532).

Acid-Catalyzed Addition of CH$_3$OH to (+)-N—BOC-DSA (39).

A solution of (+)-N—BOC-DSA (39, 1.9 mg, 5.5 μmol) in 0.55 mL of CH$_3$OH was treated with 0.66 μmol of CF$_3$SO$_3$H dissolved in THF (6 μL) and the mixture was stirred for 1 h at 25° C. under Ar. NaHCO$_3$ (2 mg) was added followed by H$_2$O (2 mL). The mixture was extracted with EtOAc (4×1 mL) and the combined organic layers were dried (Na$_2$SO$_4$), concentrated, and passed through a short plug of SiO$_2$. Samples of the reaction mixture were dissolved in i-PrOH and eluted on a Daicel ChiralCel AD analytical HPLC column (0.46×25 cm) with 15% i-PrOH-hexanes at a flow rate of 0.75 mL/min. Authentic samples of (±)-66 eluted with a t$_R$=8.09 and 9.03 min and those of (±)-67 eluted with t$_R$=16.55 and 25.99 min. Only one enantiomer of 66 (t$_R$= 8.98 min) and 67 (t$_R$=16.55 min) were detected in the acid-cataylzed addition of CH$_3$OH to (+)-39.

Acid-Catalyzed Addition of H$_2$O to N—BOC-DSA (39).

A solution of N—BOC-DSA (39, 3.6 mg, 10 μmol) in 1.0 mL of THF—H$_2$O (4:1) was treated with 2.4 μmol of CF$_3$SO$_3$H dissolved in THF (10 μL) and the mixture was stirred for 48 h at 25° C. under Ar. NaHCO$_3$ (2 mg) was added followed by H$_2$O (2 mL). The mixture was extracted with EtOAc (4×1 mL) and the combined organic layers were dried ($Na_2SO_4$) and concentrated. Chromatography ($SiO_2$, 20% EtOAc-hexane) afforded 35 (2.9 mg, 81%) identical in all respects with that previously described[17] and 68 (0.5 mg, 14%).

For methyl 6-((tert-butyloxy)carbonyl)-4,8-dihydroxy-6,7,8,9-tetrahydropyrrolo[3,2-f]quinoline-2-carboxylate (68): $^1H$ NMR ($CDCl_3$, 400 MHz) δ 9.19 (s, 1H, NH), 7.24 (s, 1H), 7.04 (d, 1H, J=2.2 Hz), 5.93 (s, 1H, OH), 4.35 (m,1H, CHOH), 3.95 (s, 3H, $OCH_3$), 3.88 (dd, 1H, J=12.9, 5.6 Hz, NCH), 3.71 (dd, 1H, J=13.2, 2.5 Hz, NCH), 3.20 (dd, 1H, J=17.2, 5.8 Hz, ArCH), 2.85 (dd, 1H, J=17.3, 4.6 Hz, ArCH), 1.54 (s, 9H, $C(CH_3)_3$); FABHRMS (NBA-NaI) m/z 385.1382 ($M^+$+Na, $C_{18}H_{22}N_2O_6$ requires 385.1376).

4-(Benzyloxy)-N-(tert-butyloxycarbonyl)-1-iodo-N-(4-penten-1-yl)-2-naphthylamine (81).

A solution of 80 (1.00 g, 2.11 mmol, 1 equiv) in benzene (100 mL) was treated with 50% w/v aqueous NaOH (20 mL). Benzyltributylammonium chloride (1.32 g, 4.22 mmol, 2 equiv) was added followed by 5-[(methanesulfonyl) oxy]-1-pentene (1.73 g, 10.53 mmol, 5 equiv). The resulting biphasic mixture was stirred vigorously at 25° C. for 12 h. The layers were allowed to separate and the aqueous portion was extracted with EtOAc (2×30 mL). The combined organic portions were washed with $H_2O$ (2×100 mL) and saturated aqueous NaCl (50 mL). Drying ($MgSO_4$), filtration, and concentration was followed by flash chromatography ($SiO_2$, 3.5×14 cm, 5% EtOAc-hexane) to furnish 81 (0.975 g, 1.15 g theoretical, 85%) as a pale yellow solid: mp 69–71° C.; $^1H$ NMR (500 MHz, $CDCl_3$) major rotamer δ 8.34–8.32 (m, 1H), 8.23–8.21 (m, 1H), 7.62–7.49 (m, 4H), 7.42–733 (m, 3H), 6.70 (s, 1H), 5.81–5.71 (m, 1H), 5.34–5.18 (m, 2H), 5.01–4.93 (m, 2H), 3.84 (ddd, J=17.5, 12.6, 7.6 Hz, 1H), 3.37–3.31 (m, 1H), 2.07–2.02 (m, 2H), 1.74–1.65 (m, 2H), 1.31 (s, 9H); $^{13}C$ NMR (125 MHz, $CDCl_3$) major rotamer δ 155.1, 154.0, 143.2, 137.9, 136.4, 135.4, 132.8, 128.7 (2C), 128.5, 128.2 (2C), 127.2, 126.2, 122.5, 115.0, 107.8, 95.1, 80.1, 70.3, 49.1, 31.3, 28.6, 28.3 (3C), 27.5; IR (film) $v_{max}$ 3067, 3036, 2974, 2923, 1697, 1615, 1590 $cm^{-1}$; FABHRMS (NBA-NaI) m/z 544.1337 ($M+Na^+$, $C_{27}H_{30}INO_3$ requires 544.1349).

Anal. Calcd for Calcd for $C_{27}H_{30}INO_3$: C, 59.65; H, 5.57; N, 2.58. Found C, 60.02; H, 5.27; N, 2.54.

7-(Benzyloxy)-5-(tert-butyloxycarbonyl)-1-methylidene-1,2,3,4-tetrahydro-5H-naphtho[1,2-b]azepine (82).

A solution of 81 (0.503 g, 0.926 mmol, 1 equiv) in $CH_3CN$ (18 mL, 0.051 M, degassed and purged with Ar) in a thick-walled reaction tube was treated with $Et_3N$ (0.257 mL, 1.85 mmol, 2 equiv) followed by $(Ph_3P)_4Pd$ (0.032 g, 0.0277 mmol, 0.03 equiv). The reaction vessel was sealed and the mixture was warmed at 130° C. for 14 h. Concentration gave a yellow semisolid that was suspended in 5% EtOAc-hexanes. The precipitated salts were removed by filtration and thoroughly rinsed with the solvent mixture. Concentration of the filtrate and radial chromatography ($SiO_2$, 2 mm plate, 5% EtOAc-hexane) afforded 82 as a colorless oil (0.343 g, 0.384 g theoretical, 89%) which slowly crystallized upon storage: mp 99–100° C.; $^1H$ NMR 400 MHz, $CDCl_3$) major rotamer δ 8.37–8.35 (m, 1H), 8.13–8.11 (m, 1H), 7.54–7.34 (m, 7H), 6.72 (s, 1H), 5.52 (s, 1H), 5.24 (s, 2H), 4.94 (s, 1H), 4.50–4.10 (m, 1H), 3.70–3.30 (m, 1H), 2.95–1.70 (m, 4H), 1.26 (s, 9H); $^{13}C$ NMR (100 MHz, $CDCl_3$major rotamer δ 153.1, 145.3, 137.2, 137.0, 132.2, 129.8, 128.7 (3C), 128.0 (2C), 127.7, 127.2, 126.6, 126.1, 124.9, 122.1, 117.3, 106.5, 79.7, 70.2, 47.4, 35.1, 29.8, 28.3 (3C); IR (film) $v_{max}$ 3071, 3031, 2971, 2931, 2852, 1694, 1590 $cm^{-1}$; FABHRMS (NBA-NaI) m/z 438.2065 ($M+Na^+$, $C_{27}H_{29}NO_3$ requires 438.2045).

7-(Benzyloxy)-5-(tert-butyloxycarbonyl)-1-(hydroxymethyl)-1,2,3,4-tetrahydro-5H-naphtho[1,2-b] azepine (83).

A solution of 82 (0.209 g, 0.504 mmol, 1 equiv) in THF (5 mL) was cooled to 0° C. prior to dropwise addition of $BH_3•SMe_2$ (0.151 mL, 10 M, 3(9) equiv). The cooling bath was removed after 5 min and the mixture was stirred at 25° C. for 12 h. The excess borane was quenched with slow addition of $H_2O$ (0.6 mL). Oxidative workup was accomplished by the addition of 2.5 M aqueous NaOH (0.605 mL, 3 equiv) followed by 30% $H_2O_2$ (0.514 mL, 9 equiv) and the resulting heterogeneous solution was stirred rapidly at 25° C. (1 h) and 50° C. (1 h). The cooled reaction mixture was treated with saturated aqueous NaCl (0.5 mL) and the layers separated. The aqueous portion was extracted with EtOAc (2×5 mL) and the combined organic portions were dried ($MgSO_4$), filtered, and concentrated. Radial chromatography ($SiO_2$, 2 mm plate, 30% EtOAc-hexane) provided 83 as a colorless oil (0.179 g, 0.218 g theoretical, 82%) which slowly crystallized upon storage: mp 108–110° C.; $^1H$ NMR 400 MHz, $CDCl_3$) major rotamer δ 8.40 (d, J=8.3 Hz, 1H), 8.18 (d, J=8.6 Hz, 1H), 7.57–7.34 (m, 7H), 6.62 (s, 1H), 5.28 (d, J=12.1 Hz, 1H), 5.17 (d, J=12.0 Hz, 1H), 4.41–4.37 (m, 1H), 4.09–4.06 (m, 1H), 3.88–3.86 (m, 2H), 2.81–2.75 (m, 1H), 2.23–2.03 (m, 2H), 1.71–1.48 (m, 3H), 1.29 (s, 9H); $^{13}C$ NMR (100 MHz, $CDCl_3$) major rotamer δ 154.0, 153.2, 139.9, 136.9, 133.6, 128.7 (2C), 128.0 (2C), 127.7, 127.0 (2C), 125.4, 125.0, 123.7, 122.7, 107.3, 80.2, 70.1, 63.3, 47.5, 39.1, 28.3 (3C), 26.3, 24.1; IR (film) $v_{max}$ 3429, 3067, 3037, 2967, 2926, 2866, 1694, 1674, 1619, 1594 $cm^{-1}$; FABHRMS (NBA-CsI) m/z 566.1333 ($M+Cs^+$, $C_{27}H_{31}NO_4$ requires 566.1307).

Anal. Calcd for $C_{27}H_{31}NO_4$: C, 74.79; H, 7.21; N, 3.23. Found: C, 74.49; H, 7.37; N, 3.44.

7-(Benzyloxy)-5-(tert-butyloxycarbonyl)-1-[((methanesulfonyl)oxy)methyl]-1,2,3,4-tetrahydro-5H-naphtho[1,2-b]azepine (84).

A solution of 83 (0.138 g, 0.319 mmol, 1 equiv) in $CH_2Cl_2$ (3 mL) was cooled to 0° C. prior to sequential addition of $Et_3N$ (0.222 mL, 1.59 mmol, 5 equiv) and $CH_3SO_2Cl$ (0.049 mL, 0.637 mmol, 2 equiv). The cooling bath was removed after 5 min and the mixture was stirred at 25° C. for 1 h. The reaction was quenched with the addition of saturated aqueous $NaHCO_3$ (0.5 mL) and the layers were separated. The aqueous portion was extracted with EtOAc (2×5 mL) and the combined organic portions were dried ($MgSO_4$), filtered, and concentrated. Radial chromatography ($SiO_2$, 2 mm plate, 30% EtOAc-hexane) furnished 84 (0.143 g, 0.163 g theoretical, 89%) as a white solid: mp 134–135° C.; $^1H$ NMR 400 MHz, $CDCl_3$) major rotamer δ 8.40 (d, 8.2 Hz, 1H), 8.13 (d, J=8.6 Hz, 1H), 7.60–7.35 (m, 7H), 6.63 (s, 1H), 5.26 (d, J=11.7 Hz, 1H), 5.17 (d, J=11.6 Hz, 1H), 4.49–4.44 (m, 2H), 4.38–4.30 (m, 2H), 2.69–2.64 (m, 4H), 2.26–2.05 (m, 2H), 1.73–1.70 (m, 2H), 1.32 (s, 9H); $^{13}C$ NMR (100 MHz, $CDCl_3$) major rotamer δ 153.8, 153.6, 140.5, 136.7, 133.0, 128.8 (2C), 128.6, 128.1 (2C), 127.7, 127.6, 127.1, 125.2, 123.3, 122.8, 107.1, 80.8, 71.4, 70.2, 47.7, 37.1, 36.1, 28.3 (3C), 26.5, 24.4; IR (film) $v_{max}$ 3056, 2974, 2933, 2862, 1692, 1615, 1590 $cm^{-1}$; FABHRMS (NBA-NaI) m/z 534.1914 ($M+Na^+$, $C_{28}H_{33}NO_6S$ requires 534.1926).

Anal. Calcd for $C_{28}H_{33}NO_6S$: C, 65.73; H, 6.51; N, 2.74; S, 6.25. Found: C, 65.68; H, 6.59; N, 2.55; S, 6.31.

A solution of 84 (0.055 g) in 50% i-PrOH-hexane was resolved on a semipreparative Diacel Chiracel OD column (10 μm, 2×25 cm) using 10% i-PrOH-hexane as eluent (7 mL/min). The effluent was monitored at 254 nm and the enantiomers eluted with retention times of 38.0 and 45.0 min, respectively (α=1.18). The fractions were collected and concentrated to afford ent-(+)-(1S)-84 ($t_R$=38.0 min, 0.0251 g) and (−)-(1R)-77 ($t_R$=45.0 min, 0.0248 g) with a 91% recovery (>99.9% ee).

(−)-(1R)-84: $[\alpha]_D^{25}$−41 (c 0.12, $CHCl_3$).

ent-(+)-(1S)-84: $[\alpha]_D^{25}$+46 (c 0.13, $CHCl_3$).

5-(tert-Butyloxycarbonyl)-7-hydroxy-1-[((methanesulfonyl)oxy)methyl]-1,2,3,4-tetrahydro-5H-naphtho[1,2-b]azepine (85).

A solution of 84 (0.096 g, 0.188 mmol, 1 equiv) in THF (3.0 mL) was treated with 10% Pd—C (0.042 g, 0.04 mmol, 0.2 equiv) followed by aqueous $HCO_2NH_4$ (1.0 mL, 25% w/v, 21 equiv) and the resulting mixture was stirred at 25° C. for 2.5 h. The mixture was filtered through Celite to afford a biphasic filtrate which was partitioned. The aqueous phase was extracted with EtOAc (2×2 mL) and the combined organic portions were dried ($MgSO_4$), filtered, and concentrated to give 85 as an analytically pure white solid (0.072 g, 0.079 g theoretical, 91%): mp 141–142° C.; $^1$H NMR 400 MHz, DMF-$d_7$) major rotamer δ 8.29 (d, J=8.2 Hz, 1H), 8.26 (d, J=8.7 Hz, 1H), 7.62–7.59 (m, 1H), 7.54–7.50 (m, 1H), 6.82 (s, 1H), 4.59–4.47 (m, 1H), 4.43–4.25 (m, 3H), 3.02 (s, 3H), 2.98–2.76 (m, 1H), 2.35–2.20 (m, 1H), 2.13–1.95 (m, 1H), 1.71–1.67 (m, 2H), 1.39 (s, 9H); $^{13}$C NMR (100 MHz, DMF-$d_7$)major rotamer δ 154.0, 153.5, 141.8, 134.0, 127.7, 125.2, 125.1, 124.3, 123.3, 123.0, 110.3, 80.4, 71.4, 48.2, 36.8, 36.4, 28.2 (3C), 27.2, 25.0; IR (film) $v_{max}$ 3262, 2974, 2933, 2872, 1692, 1662, 1594 $cm^{-1}$; FABHRMS (NBA-NaI) m/z 444.1468 (M+$Na^+$, $C_{21}H_{27}NO_6S$ requires 444.1457).

(−)-(1R)-85: $[\alpha]_D^{25}$−63 (c 0.084, THF).

ent-(+)-(1S)-85: $[\alpha]_D^{25}$+58 (c 0.084, THF).

7-(Benzyloxy)-5-(tert-butyloxycarbonyl)-1-(chloromethyl)-1,2,3,4-tetrahydro-5H-naphtho[1,2-b]azepine (86).

A solution of 83 (0.105 g, 0.24 mmol, 1 equiv) in $CH_2Cl_2$ (2 mL) was treated with $CCl_4$ (0.225 mL, 2.33 mmol, 9.7 equiv) followed by $Ph_3P$ (0.212 g, 0.81 mmol, 3.3 equiv) and the mixture was stirred at 25° C. for 2.5 h. The crude reaction solution was passed through a plug of silica gel and concentrated. Radial chromatography ($SiO_2$, 1 mm plate, 5% EtOAc-hexane) provided 86 as a pale yellow oil (0.048 g, 0.108 g theoretical, 44%): $^1$H NMR (250 MHz, $CDCl_3$) major rotamer δ 8.44–8.36 (m, 1H), 8.15–7.12 (m, 1H), 7.62–7.33 (m, 7H), 6.64 (s, 1H), 5.31–5.15 (m, 2H), 4.46–4.41 (m, 1H), 4.17–4.08 (m, 1H), 3.92–3.81 (m, 1H), 3.74–3.63 (m, 1H), 2.78–2.69 (m, 1H), 2.41–2.35 (m, 1H), 2.17–2.05 (m, 1H), 1.72–1.67 (m, 2H), 1.30 (s, 9H); IR (film) $v_{max}$ 2971, 2930, 2859, 1693, 1617, 1592 $cm^{-1}$; FABHRMS (NBA-NaI) m/z 451.1933 ($M^+$, $C_{27}H_{30}ClNO_3$ requires 451.1914).

5-(tert-Butyloxycarbonyl)-1-(chloromethyl)-7-hydroxy-1,2,3,4-tetrahydro-5H-naphtho[1,2-b]azepine (87).

A solution of 86 (0.043 g, 0.095 mmol, 1 equiv) in THF (1.5 mL) was treated with 10% Pd—C (0.020 g, 0.019 mmol, 0.2 equiv) followed by aqueous $HCO_2NH_4$ (0.5 mL, 25% w/v, 1.98 mmol, 21 equiv) and the resulting black suspension was stirred rapidly at 25° C. for 2.5 h. The crude mixture was filtered through a plug of Celite to afford a biphasic filtrate which was partitioned. The aqueous portion was extracted with EtOAc (2×1 mL) and the combined organic portions were dried ($MgSO_4$), filtered, and concentrated to provide 87 as an analytically pure white solid (0.032 g, 0.034 g theoretical, 94%). Recrystallization from 10% EtOAc-hexane gave colorless plates suitable for X-ray analysis:[24] mp 157–159° C.; $^1$H NMR (400 MHz, $CDCl_3$) major rotamer δ 7.98–7.94 (m, 1H), 7.37–7.32 (m, 1H), 7.22–7.19 (m, 1H), 6.96–6.90 (m, 1H), 6.47 (s, 1H), 4.41–4.26 (m, 1H), 4.19–4.07 (m, 1H), 3.89–3.81 (m, 2H), 2.88–2.78 (m, 1H), 2.51–2.46 (m, 1H), 2.18–2.05 (m, 1H), 1.71–1.67 (m. 2H), 1.40 (s, 9H); $^1$H NMR 400 MHz, acetone-$d_6$) major rotamer δ 9.17 (s, 1H), 8.27 (d, J=8.1 Hz, 1H), 8.19–8.17 (m, 1H), 7.59–7.54 (m, 1H), 7.50–7.46 (m, 1H), 6.75 (s, 1H), 4.39–4.36 (m, 1H), 4.19–4.15 (m, 1H), 3.92–3.87 (m, 1H), 3.75–3.63 (m, 1H), 2.75–2.68 (m, 1H), 2.37–2.33 (m, 1H), 2.06–2.04 (m, 1H), 1.69–1.67 (m, 2H), 1.40 (s, 9H); $^{13}$C NMR(100 MHz, $CDCl_3$)major rotamer δ 155.8, 152.9, 151.6, 139.3, 132.3, 126.5, 124.9, 124.7, 123.5, 122.4, 109.4, 81.5, 48.9, 44.6, 38.6, 28.4 (3C), 26.3, 24.2; IR (film) $v_{max}$ 3287, 2965, 2915, 2844, 1693, 1663 $cm^{-1}$; FABHRMS (NBA-NaI) m/z 384.1352 (M+$Na^+$, $C_{20}H_{24}ClNO_3$ requires 384.1342).

A solution of 87 (0.0096 g) in 50% i-PrOH-hexane was resolved on a semipreparative Diacel Chiracel OD column (10 μm, 2×25 cm) using 6% i-PrOH-hexane as eluent (6 mL/min). The effluent was monitored at 254 nm and the enantiomers eluted with retention times of 22.6 and 26.8 min, respectively (α=1.19). The fractions were collected and concentrated to afford (−)-(1R)-87 ($t_R$=22.6 min, 0.0033 g) and ent-(+)-(1S)-87 ($t_R$=26.8 min, 0.0031 g) with a 67% recovery (>99.9% ee). The absolute configuration of (−)-(1R)-80 was established by X-ray analysis.[24]

(−)-(1R)-87: $[\alpha]_D^{25}$−67 (c 0.017, THF).

ent-(+)-(1S)-87: $[\alpha]_D^{25}$+67 (c 0.016, THF).

N-(tert-Butyloxycarbonyl)-1,2,3,4,11,11a-hexahydrocyclopropa[c]naphtho[2,1-b]azepin-6-one (N—BOC-CNA, 78).

A sample of 85 (0.025 g, 0.059 mmol, 1 equiv) was suspended in $CH_3CN$ (1.0 mL) and treated with DBU (0.027 mL, 0.178 mmol, 3 equiv) at 25° C. to instantly afforded a homogeneous pale yellow solution. The solvent was removed with a gentle stream of $N_2$ after 5 min. Flash chromatography ($SiO_2$, 1×7 cm, 30% EtOAc-hexane with 5% $Et_3N$) firmished 78 as a colorless oil (0.017 g, 0.019 g theoretical, 87%): $^1$H NMR (400 MHz, $CD_3CN$) δ 8.12 (dd, J=7.9, 1.5 Hz, 1H), 7.61 (ddd, J=8.3, 7.1, 1.5 Hz, 1H), 7.41 (ddd, J=8.0, 7.2, 1.0 Hz, 1H), 7.14 (d, J=8.1 Hz, 1H), 6.48 (s, 1H), 4.09–4.02 (m, 1H), 2.69–2.54 (m, 1H), 2.28–2.22 (m, 1H), 2.10–2.07 (m, 2H), 1.95–1.91 (m, 2H overlapping with solvent), 1.75–1.72 (m, 1H), 1.62–1.57 (m, 1H), 1.26 (broad s, 9H); $^{13}$C NMR (100 MHz, $CD_3CN$) δ 186.4, 162.1, 146.8, 133.7, 132.8, 129.3, 126.8, 126.6, 123.3, 81.0, 47.8, 40.2, 33.8, 28.4,28.3, 26.8 (3C), 26.0, 25.9; IR (film) $v_{max}$ 2923, 2852, 1698, 1647, 1596 $cm^{31\ 1}$; UV (THF) $\lambda_{max}$ 304 (ε 8600), 258 (ε 11100), 220 (ε 15500) nm; FABHRMS (NBA-NaI) m/z 326.1766 (M+$H^+$, $C_{20}H_{24}NO_3$ requires 326.1756).

(+)-78: $[\alpha]_D^{25}$+36 (c 0.009, EtOAc).

ent-(−)-78: $[\alpha]_D^{25}$−36 (c 0.016, EtOAc).

1,2,3,4,11,11a-Hexahydrocyclopropa[c]naphtho[2,1-b]azepin-6-one (CNA, 79).

A sample of 85 (0.030 g, 0.07 mmol, 1 equiv) was suspended in 3.9 M HCl-EtOAc (1.5 mL). After 40 min, the volatiles were removed with a gentle stream of $N_2$ followed by high vacuum. The resulting white foam was dissolved in $CH_3CN$ containing DBU (0.105 mL, 0.70 mmol, 10 equiv in 1 mL of $CH_3CN$). The solvent was removed with a gentle stream of $N_2$ after 5 min. Radial chromatography ($SiO_2$, 1 mm plate, 95% $CH_2Cl_2$—$CH_3OH$) furnished 79 as a pale yellow solid (0.012 g, 0.016 g theoretical, 77%). Recrystallization from 10% $CH_3OH$—$CH_3CN$ gave pale yellow plates suitable for X-ray analysis:[24] mp 180–183° C. with decomposition; $^1$H NMR 400 MHz, $CD_3OD$) δ 8.07 (dd, J=7.8, 1.5 Hz, 1H), 7.50 (ddd, J=8.7, 7.2, 1.6 Hz, 1H), 7.33

(ddd, J=8.0, 7.2, 1.0 Hz, 1H), 7.13 (d, J=8.1 Hz, 1H), 6.00 (s, 1H), 3.54–3.48 (m, 1H), 3.00–2.90 (m, 1H), 2.78–2.74 (m, 1H), 2.50 (dd, J=8.7, 5.0 Hz, 1H), 2.41–2.36 (m, 1H), 2.24–2.15 (m, 1H), 1.92–1.79 (m, 3H); $^{13}$C NMR (150 MHz, CD$_3$OD) δ 184.6, 175.0, 146.3, 133.0, 132.7, 126.6, 126.1, 122.4, 107.9, 45.4, 38.2, 31.0 (2C), 26.4, 26.1; IR (film) $v_{max}$ 3285, 2924, 2855, 1608, 1584 cm$^{31}$ $^1$; UV (CH$_3$OH) $\lambda_{max}$ 342 (ε 11900), 308 (ε 8300), 245 (ε 17100) nm; FABHRMS (NBA-NaI) m/z 226.1238 (M+H$^+$, C$_{15}$H$_{16}$NO requires 226.1232).

7-(Benzyloxy)-1-methylidene-1,2,3,4-tetrahydro-5H-naphthol[1,2-b]azepine Hydrochloride (88).

A solution of 82 (0.226 g, 0.55 mmol, 1 equiv) was dissolved in 3.9 M HCl-EtOAc (7.0 mL). After 40 min, the volatiles were removed with a gentle stream of N$_2$ followed by high vacuum. The resulting crude pale green solid was used directly for the synthesis of 89 and 90 without further characterization.

7-(Benzyloxy)-5-(methoxycarbonyl)-1-methylidene-1,2,3,4-tetrahydro-5H-naphtho-[1,2-b]azepine (89).

A solution of 88 (0.049 g, 0.14 mmol, 1 equiv) in THF (1.5 mL) was treated with NaHCO$_3$ (0.026 g, 0.31 mmol, 2.2 equiv) followed by methyl chloroformate (0.022 ml, 0.28 mmol, 2.0 equiv) and the mixture was stirred at 25° C. for 5 h. The reaction was quenched with the addition of saturated aqueous NaHCO$_3$ (0.5 mL) and the resulting layers were separated. The aqueous portion was extracted with EtOAc (2×2 mL) and the combined organic portions were dried (MgSO$_4$), filtered, and concentrated. Trituration with 10% EtOAc-hexane furnished 89 as a white solid (0.049 g, 0.052 g theoretical, 94%): mp 99–100° C.; $^1$H NMR (500 MHz, CDCl$_3$) major rotamer δ 8.38–8.36 (m, 1H), 8.14–8.13 (m, 1H), 7.54–7.36 (m, 7H), 6.73 (s, 1H), 5.56 (s, 1H), 5.25 (s, 2H), 4.99 (s, 1H), 4.50–4.20 (m, 1H), 3.59 (s, 3H), 3.10–2.35 (m 1H), 2.22–1.70 (m, 4H); $^{13}$C NMR (125 MHz, CDCl$_3$) major rotamer δ 155.5, 153.4, 144.7, 136.8, 136.2, 132.2, 129.9, 128.6 (2C), 127.9, 127.3 (2C), 126.8, 126.1, 125.2 (2C), 122.2, 118.0, 105.8, 70.2, 52.8, 48.1, 35.0, 29.7; IR (film) $v_{max}$ 3067, 2923, 2862, 1703, 1590, 1508 cm$^{-1}$; FABHRMS (NBA-NaI) m/z 373.1688 (M$^+$, C$_{24}$H$_{23}$NO$_3$ requires 373.1678).

7-(Benzyloxy)-1-(hydroxymethyl)-5-(methoxycarbonyl)-1,2,3,4-tetrahydro-5H-naphtho[1,2-b]azepine (91).

Following the general procedure detailed for 83, 89 (0.049 g, 0.013 mmol, 1 equiv) was treated with BH$_3$•SMe$_2$ (0.039 mL, 10 M, 3(9) equiv), quenched with H$_2$O (0.16 mL), and oxidized with aqueous 2.5 M NaOH (0.16 mL, 0.39 mmol, 3 equiv) and 30% aqueous H$_2$O$_2$ (0.134 mL, 9 equiv). Radial chromatography (SiO$_2$, 1 mm plate, 50% EtOAc-hexane) provided 91 as a white solid (0.033 g, 0.051g theoretical, 64%): mp 9–92° C.; $^1$H NMR (500 MHz, CDCl$_3$) major rotamer δ 8.41 (d, J=8.5 Hz, 1H), 8.18 (d, J=8.5 Hz, 1H), 7.57–7.35 (m, 7H), 6.63 (s, 1H), 5.25–5.17 (m, 2H), 4.46–4.43 (m, 1H), 4.09–4.07 (m, 1H), 3.87–3.76 (m, 2H), 3.59 (s, 3H), 2.93–2.83 (m, 1H), 2.21–2.08 (m, 2H), 1.70–1.64 (m, 1H); $^{13}$C NMR (125 MHz, CDCl$_3$) major rotamer δ 155.6, 153.4, 139.0, 136.7, 133.5, 128.6 (2C), 128.0 (2C), 127.6, 127.3 (3C), 125.2, 123.7, 122.8, 106.9, 70.1, 63.4, 52.9, 48.3, 39.1, 26.4, 24.1; IR (film) $v_{max}$ 3453, 3063, 3032, 2940, 2868, 1696, 1593 cm$^{-1}$; FABHRMS (NBA-NaI) m/z 392.1871 (M+H$^+$, C$_{24}$H$_{25}$NO$_4$ requires 392.1862).

7-(Benzyloxy)-1-[((methanesulfonyl)oxy)methyl]-5-(methoxycarbonyl)-1,2,3,4-tetrahydro-5H-naphtho[1,2-b]azepine (93).

Following the general procedure detailed for 84, 91 (0.029 g, 0.074 mmol, 1 equiv) was treated with Et$_3$N (0.052 mL, 0.371 mmol, 5 equiv) and CH$_3$SO$_2$Cl (0.017 mL, 0.148 mmol, 2 equiv). Radial chromatography (SiO$_2$, 1 mm plate, 50% EtOAc-hexane) furnished 93 (0.032 g, 0.035 g theoretical, 91%) as a white solid: mp 130–132° C.; $^1$H NMR (500 MHz, CDCl$_3$) major rotamer δ 8.40 (d, J=8.5 Hz, 1H), 8.13 (d, J=8.5 Hz, 1H), 7.61–7.35 (m, 7H), 6.63 (s, 1H), 5.27–5.17 (m, 2H), 4.51–4.33 (m, 4H), 3.60 (s, 3H), 2.86–2.81 (m, 1H), 2.54 (s, 3H), 2.32–2.23 (m, 1H), 2.07–2.04 (m, 1H), 1.76–1.70 (m, 2H); $^{13}$C NMR (125 MHz, CDCl$_3$) major rotamer δ 155.3, 153.7, 139.5, 136.6, 133.1, 128.6 (2C), 128.0 (2C), 127.7, 127.6, 127.3, 125.4, 124.3, 123.4, 122.8, 106.9, 71.1, 70.1, 53.0, 48.3, 36.8, 36.2, 26.7, 24.5; IR (film) $v_{max}$ 3063, 3022, 2938, 2858, 1701, 1593 cm$^{-1}$; FABHRMS (NBA) m/z 470.1648 (M+H$^+$, C$_{25}$H$_{27}$NO$_6$S requires 470.1637).

7-Hydroxy-1-[((methanesulfonyl)oxy)methyl]-5-(methoxycarbonyl)-1,2,3,4-tetrahydro-5H-naphtho[1,2-b]azepine (95).

Following the general procedure detailed for 85, 93 (0.028 g, 0.060 mmol, 1 equiv) was treated with 10% Pd—C (0.010 g, 0.009 mmol, 0.16 equiv) followed by aqueous HCO$_2$NH$_4$ (0.265 mL, 25% w/v, 18 equiv). Filtration and concentration gave 95 as an analytically pure white solid (0.0204 g, 0.0225 g theoretical, 91%): mp 113–115° C.; $^1$H NMR (500 MHz, CD$_3$OD) major rotamer δ 8.25 (d, J=7.5 Hz, 1H), 8.14 (d, J=8.5 Hz, 1H), 7.55–7.45 (m, 2H), 6.60 (s, 1H), 4.41–4.33 (m, 4H), 3.66 (s, 3H), 2.85–2.79 (m, 1H), 2.64 (s, 3H), 2.35–2.20 (m, 1H), 2.13–1.95 (m, 1H), 1.71–1.67 (m, 2H); $^{13}$C NMR (125 MHz, CD$_3$OD) major rotamer δ 157.2, 154.4, 140.9, 134.8, 128.3, 126.2, 125.8 (2C), 124.5, 124.3, 123.9, 72.5, 53.6, 49.9, 37.3, 36.9, 27.9, 25.5; IR (film) $v_{max}$ 3283, 2938, 2857, 1672, 1621, 1591 cm$^{31}$ ; FABHRMS (NBA-NaI) m/z 379.1081 (M$^+$, C$_{18}$H$_{21}$NO$_6$S requires 379.1090).

N-(Methoxycarbonyl)-1,2,3,4,11,11a-hexahydrocyclopropa[c]naphtho[2,1-b]azepin-6-one (N—CO$_2$Me-CNA, 97).

Following the general procedure detailed for 78, 95 (0.0071 g, 0.019 mmol, 1 equiv) was treated with DBU (0.008 mL, 0.057 mmol, 3 equiv). Flash chromatography (SiO$_2$, 1×7 cm, 50% EtOAc-hexane with 5% Et$_3$N) furnished 97 as a colorless oil (0.0048 g, 0.0052 g theoretical, 90%). Recrystallization from 10% EtOAc-hexane gave colorless plates suitable for X-ray analysis:[24] mp 259–261° C.; $^1$H NMR (500 MHz, acetone-d$_6$) δ 8.13 (dd, J=8.0, 1.5 Hz, 1H), 7.63 (ddd, J=8.5, 7.5, 1.5 Hz, 1H), 7.42 (ddd, J=8.0, 7.2, 1.5 Hz, 1H), 7.20 (d, J=8.5 Hz, 1H), 6.52 (s, 1H), 4.26–4.15 (m, 1H), 3.61 (s, 3H), 2.79–2.73 (m, 1H), 2.32–2.28 (m, 1H), 2.18–2.09 (m, 3H), 1.96–1.94 (m, 1H), 1.80–1.78 (m, 1H), 1.69–1.65 (m, 1H); $^{13}$C NMR (125 MHz, acetone-d$_6$) δ 185.6, 155.2, 146.5 (2C), 133.6, 132.9, 129.7, 126.7, 126.5, 123.2, 53.1, 48.6, 39.8, 33.5, 26.8, 25.8, 25.5; IR (film) $v_{max}$ 3067, 2923, 2851, 1708, 1646, 1600, 1446 cm$^{-1}$; FABHRMS (NBA-NaI) m/z 284.1281 (M+H$^+$, C$_{17}$H$_{17}$NO$_3$ requires 284.1287).

7-(Benzyloxy)-5-[(5,6,7-trimethoxyindol-2-yl)carbonyl]-1-methylidene-1,2,3,4-tetrahydro-5H-naphtho[1,2-b]azepine (90).

A solution of 88 (0.142 g, 0.405 mmol, 1 equiv) in DMF (3 mL) was treated with [[3-(dimethylamino)propyl]ethyl] carbodiimide hydrochloride (EDCI, 0.233 g, 1.22 mmol, 3 equiv) followed by 5,6,7-trimethoxyindole-2-carboxylic acid (0.122 g, 0.486 mmol, 1.2 equiv) and the reaction mixture was stirred at 25° C. for 4.5 h. The crude reaction mixture was diluted with EtOAc (4 mL) and extracted with H$_2$O (2 mL). The aqueous portion was extracted with EtOAc (2×1 mL). The combined organic portions were dried (MgSO$_4$), filtered, and concentrated. Radial chromatography (SiO$_2$, 2 mm plate, 50% EtOAc-hexane) furnished 90 (0.177 g, 0.222 g theoretical, 80%) as a pale yellow solid: mp 88–90° C.; $^1$H NMR (500 MHz, CDCl$_3$) major rotamer δ 9.30 (s, 1H), 8.47–8.44 (m, 1H), 7.98–7.97 (m, 1H), 7.63–7.57 (m, 2H), 7.39–7.36 (m, 2H), 7.26–7.18 (m, 3H), 6.72 (s, 1H), 6.46 (s, 1H), 6.23–6.18 (m, 1H), 5.31–5.27 (m, 1H), 5.19–5.14 (m, 1H), 5.09–5.04 (m, 1H), 4.94–4.89 (m, 1H), 4.02 (s, 3H), 3.88 (s, 3H), 3.75 (s, 3H), 3.67–3.61 (m, 1H), 3.00–2.91 (m, 1H), 2.18–2.10 (m, 4H); $^{13}$C NMR (125 MHz, CDCl$_3$) major rotamer δ 162.1, 154.5, 149.4, 144.3, 139.8, 138.6, 137.3, 136.5, 136.4, 136.3, 132.0, 129.5, 128.4 (2C), 127.9, 127.1 (2C), 126.9, 126.3, 125.7, 123.4, 122.9, 118.2, 107.3, 106.9, 97.8, 70.2, 61.4, 56.0, 54.7, 47.3, 34.7, 25.2, 22.9; IR (film) $ν_{max}$ 3448, 3235, 3062, 2930, 1607, 1581, 1495 cm$^{-1}$; FABHRMS (NBA-CsI) m/z 681.1378 (M+Cs$^+$, C$_{34}$H$_{32}$N$_2$O$_5$ requires 681.1366).

7-(Benzyloxy)-1-(hydroxymethyl)-5-[(5,6,7-trimethoxyindol-2-yl)carbonyl]-1,2,3,4-tetrahydro-5H-naphtho[1,2-b]azepine (92).

Following the general procedure detailed for 83, 90 (0.200 g, 0.365 mmol, 1 equiv) was treated with BH$_3$·SMe$_2$ (0.110 mL, 10 M, 9 equiv), quenched with H$_2$O (0.44 mL), and oxidized with aqueous 2.5 M NaOH (0.44 mL, 1.10 mmol, 3 equiv) and 30% aqueous H$_2$O$_2$ (0.373 mL, 9 equiv). Radial chromatography (SiO$_2$, 2 mm plate, 70% EtOAc-hexane) provided 92 (0.107 g, 0.207 g theoretical, 52%) as an amber oil. Recrystallization from EtOAc gave a white microcrystalline solid: mp 178–180° C. with decomposition; $^1$H NMR (500 MHz, CDCl$_3$) major rotamer δ 9.26 (s, 1H), 8.48 (d, J=10.4 Hz, 1H), 8.28 (d, J=10.8 Hz, 1H), 7.68–7.65 (m, 1H), 7.60–7.57 (m, 1H), 7.35–7.33 (m, 2H), 7.22–7.13 (m, 3H), 6.66 (s, 1H), 6.43 (s, 1H), 5.23–5.21 (m, 1H), 5.13–5.10 (m, 1H), 5.03–4.99 (m, 1H), 4.95–4.90 (m, 1H), 4.24–4.21 (m, 2H), 4.03 (s, 3H), 3.87 (s, 3H), 3.73 (s, 3H), 3.26–3.20 (m, 1H), 2.46–2.40 (m, 1H), 1.95–1.92 (m, 1H), 1.30–1.23 (m, 3H); $^{13}$C NMR (125 MHz, CDCl$_3$) major rotamer δ 160.7, 153.9, 149.5, 140.0, 139.8, 138.6, 136.3, 134.3, 129.0, 128.4 (2C), 127.8, 127.7, 127.1 (2C), 126.2, 125.9, 125.6, 124.8, 123.7, 123.3, 123.2, 108.4, 107.6, 97.9, 70.6, 70.2, 61.4, 61.1, 56.1, 41.3, 38.8, 31.8, 17.3; IR(film) 3446, 3290, 3062, 2927, 1732, 1608, 1587 cm$^{-1}$; FABHRMS (NBA-CsI) m/z 699.1482 (M+Cs$^+$, C$_{34}$H$_{34}$N$_2$O$_6$ requires 699.1471).

A solution of 92 (0.025 g) in 50% i-PrOH-hexane was resolved on a semipreparative Diacel Chiracel OD column (10 μm, 2×25 cm) using 30% i-PrOH-hexane as eluent (8 mL/min). The effluent was monitored at 254 nm and the enantiomers eluted with retention times of 20.9 and 24.0 min, respectively (α=1.15). The fractions were collected and concentrated to afford (+)-(1R)-92 (t$_R$=20.9 min, 0.0088 g) and ent-(-)-(1S)-92 (t$_R$=45 min, 0.0093 g) with a 72% recovery (>99.9% ee).

(+)-(1R)-92: $[α]_D^{25}$+58 (c 0.044, EtOAc).$^{38}$
ent-(-)-(1S)-92: $[α]_D^{25}$ $^{-56}$ (c 0.047, EtOAc).

7-(Benzyloxy)-1-[((methanesulfonyl)oxy)methyl]-5-[(5,6,7-trimethoxyindol-2-yl)carbonyl]-1,2,3,4-tetrahydro-5H-naphtho[1,2-b]azepine (94).

Following the general procedure detailed for 84, 92 (0.040 g, 0.071 mmol, 1 equiv) was treated with Et$_3$N (0.049 mL, 0.354 mmol, 5 equiv) and CH$_3$SO$_2$Cl (0.011 mL, 0.141 mmol, 2 equiv). Radial chromatography (SiO$_2$, 1 mm plate, 70% EtOAc-hexane) firnished 94 (0.034 g, 0.046 g theoretical, 75%) as a white solid: mp 175–177° C. with decomposition; $^1$H NMR (500 MHz, CDCl$_3$) major rotamer δ 9.30 (s, 1H), 8.49 (dd, J=8.0, 1.0 Hz, 1H), 8.25 (d, J=9.0 Hz, 1H), 7.68 (ddd, J=8.0, 6.5, 1.0 Hz 1H), 7.61–7.58 (m, 1H), 7.36–7.34 (m, 2H), 7.22–7.16 (m, 3H), 6.69 (s, 1H), 6.43 (s, 1H), 5.28 (d, J=2.0 Hz, 1H), 5.27–5.26 (m, 1H), 5.14 (d, J=11.5 Hz, 1H), 5.03–4.99 (m, 2H), 4.52–4.49 (m, 1H), 4.04 (s, 3H), 3.88 (s, 3H), 3.74 (s, 3H), 3.21–3.17 (m, 1H), 2.78 (s, 3H), 2.60–2.59 (m, 1H), 2.20–2.18 (m, 1H), 1.34–1.32 (m, 3H); $^{13}$C NMR (125 MHz, CDCl$_3$) major rotamer δ 160.7, 154.0, 149.6, 140.1, 139.9, 138.6, 136.2, 133.8, 128.7, 128.4 (2C), 127.9, 127.8, 127.1 (2C), 125.9, 125.7, 125.1, 124.9, 123.5, 123.3, 123.2, 108.6, 107.4, 97.8, 79.9, 70.2, 61.4, 61.1, 56.0, 41.4, 38.4, 36.7, 30.5, 16.9; IR (film) $ν_{max}$ 3453, 3299, 3001, 2929, 2827, 1608, 1588 cm$^{-1}$; FABHRMS (NBA-CsI) m/z 777.1267 (M+Cs$^+$, C$_{35}$H$_{36}$N$_2$O$_6$ requires 777.1247).

(+)-(1R)-94: $[α]_D^{25}$+26 (c 0.044, EtOAc).$^{38}$
ent-(-)-(1S)-94: $[α]_D^{25}$-28 (c 0.042, EtOAc).

7-Hydroxy-1-[((methanesulfonyl)oxy)methyl]-5-[(5,6,7-trimethoxyindol-2-yl)carbonyl]-1,2,3,4-tetrahydro-5H-naphtho[1,2-b]azepine (96).

Following the general procedure detailed for 85, 94 (0.024 g, 0.037 mmol, 1 equiv) was treated 10% Pd—C (0.006 g, 0.15 equiv) followed by aqueous HCO$_2$NH$_4$ (0.165 mL, 25% w/v, 18 equiv). Filtration and concentration gave 96 as an analytically pure colorless oil in quantitative yield (0.020 g, 0.020 g theoretical): $^1$H NMR (500 MHz, acetone-d$_6$) major rotamer δ 10.17 (s, 1H), 9.20 (s, 1H), 8.37–8.34 (m, 2H), 7.68–7.56 (m, 2H), 6.66 (s, 1H), 6.51 (s, 1H), 5.42 (s, 1H), 5.23–5.22 (m, 1H), 4.95–4.92 (m, 1H), 4.60–4.59 (m, 1H), 3.98 (s, 3H), 3.79 (s, 3H), 3.68 (s, 3H), 3.21–3.13 (m, 1H), 3.05 (s, 3H), 2.55–2.43 (m, 1H), 2.19–2.16 (m, 1H), 1.40–1.37 (m, 3H); $^{13}$C NMR (125 MHz, acetone-d$_6$) major rotamer δ 161.1, 153.4, 150.8, 141.3, 141.1, 139.8, 135.1, 130.6, 128.3, 126.0, 125.8 (2C), 125.0, 124.6, 124.3, 123.8, 110.7, 108.8, 98.7, 81.6, 61.4, 61.3, 56.3, 41.8, 38.1, 37.5, 31.2, 17.4; IR (film) $ν_{max}$ 3313, 2936, 2836, 1731, 1592, 1584 cm$^{31\ 1}$; FABHRMS (NBA-CsI) m/z 687.0751 (M+Cs$^+$, C$_{28}$H$_{30}$N$_2$O$_8$S requires 687.0774).

(+)-(1R)-96: $[α]_D^{25}$+143 (c 0.036, THF).$^{38}$
ent-(-)-(1S)-96: $[α]_D^{25}$-147 (c 0.036, THF).

N-[(5,6,7-Trimethoxyindol-2-yl)carbonyl]-1,2,3,4,11,11a-hexahydrocyclopropa-[c]naphtho[2,1-b]azepin-6-one (98, CNA-TMI).

Following the general procedure detailed for 78, 97 (0.0054 g, 0.001 mmol, 1 equiv) was treated with DBU (0.004 mL, 0.030 mmol, 3 equiv). Flash chromatography (SiO$_2$, 1×7 cm, 50% EtOAc-hexane with 5% Et$_3$N) funished 98 as a yellow solid (0.0022 g, 0.0046 g theoretical, 48%). Recrystallization from EtOAc gave yellow needles: mp 222–227° C.; $^1$H NMR (CD$_3$CN, 400 MHz) major rotamer δ 9.67 (br s, 1H), 8.15 (dd, J=7.8, 1.3 Hz, 1H), 7.65–7.61 (m, 1H), 7.49–7.31 (m, 1H), 7.32 (d, J=8.1 Hz, 1H), 6.77 (s, 1H), 6.63 (s, 1H), 6.12 (s, 1H), 4.29 (ddd, J=12.0, 6.3, 5.3 Hz, 1H), 3.99 (s, 3H), 3.83 (s, 3H), 3.76 (s, 3H), 3.37 (ddd, J=13.0, 8.5, 7.0 Hz, 1H), 2.86–2.83 (m, 1H), 2.54–2.48 (m, 1H), 2.32–2.27 (m, 2H), 1.31–1.26 (m, 3H); IR (film) $ν_{max}$ 3292, 2923, 2841, 1626, 1600, 1523, 1456 cm$^{31\ 1}$; FABHRMS (NBA-CsI) m/z 459.1934 (M+H$^+$, C$_{27}$H$_{26}$N$_2$O$_5$ requires 459.1920).

(-)-98: $[α]_D^{25}$-146 (c 0.004, THF).$^{38}$
ent-(+)-98: $[α]_D^{25}$+146 (c 0.004, THF).

Acid-Catalyzed Addition of H$_2$O to 10: 6-(tert-Butyloxycarbonyl)-2,8-dihydroxy-1,2,3,4,5-pentahydro-6H-naphtho[1,2-b]azocine (99).

A solution of 78 (0.0074 g, 0.022 mmol, 1 equiv) in THF (0.75 mL) was treated with H$_2$O (0.25 mL) followed by CF$_3$SO$_3$H (0.027 mL, 0.1 M in THF, 0.12 equiv) at 25° C. and the mixture was stirred for 5 min. The reaction mixture was treated with NaHCO$_3$ (0.01 g) followed by H$_2$O (1.0 mL). The aqueous portion was extracted with EtOAc (2×1 mL) and the combined organic portions were dried (MgSO$_4$), filtered, and concentrated to a colorless oil. $^1$H NMR analysis of the crude mixture and comparison with 101 indicated the presence of the ring expansion solvolysis product exclusively ($\geqq$40–20:1). Radial chromatography (SiO$_2$, 1 mm plate, 50% EtOAc-hexane) provided 99 as a colorless oil (0.0077 g, 0.0078 g theoretical, 99%) which slowly crystallized upon storage: mp 235–237° C.; $^1$H NMR 400 MHz, acetone-d$_6$) major rotamer δ 9.08 (s, 1H), 8.26 (d, J=8.3 Hz, 1H), 8.11 (d, J=8.5 Hz, 1H), 7.57–7.54 (m, 1H), 7.49–7.44 (m, 1H), 6.68 (s, 1H), 4.38–4.35 (m, 1H), 4.07–3.95 (m, 1H), 3.40–3.35 (m, 1H), 3.02–2.80 (m, 2H), 2.01–1.93 (m, 1H), 1.71–1.63 (m, 1H), 1.52–1.44 (m, 1H), 1.28 (s, 9H), 1.20–1.17 (m, 2H); IR (film) $v_{max}$ 3309, 2977, 2927, 2867, 1689, 1664, 1619, 1589 cm$^{-1}$; FABHRMS (NBA-CsI) m/z 476.0848 (M+Cs$^+$, C$_{20}$H$_{25}$NO$_4$ requires 476.0838).

Acid-Catalyzed Addition of H$_2$O to (+)-78: (−)-6-(tert-Butyloxycarbonyl)-2,8-dihydroxy-1,2,3,4,5-pentahydro-6H-naphtho[1,2-b]azocine (99).

A solution of (+)-78 (0.0030 g, 0.009 mmol, 1 equiv) in THF (0.38 mL) was treated with H$_2$O (0.13 mL) followed by CF$_3$SO$_3$H (0.011 mL, 0.1 M in THF, 0.12 equiv) at 25° C. and the mixture was stirred for 5 min. Workup as described for racemic 99 and radial chromatography (SiO$_2$, 1 mm plate, 50% EtOAc-hexane) provided (−)-99 as a colorless oil (0.0032 g, 0.0032 g theoretical, 99%) which slowly crystallized upon storage. This material was identical with racemic 99 in all respects. The solvolysis of (+)-78 provided a single enantiomer established by chiral phase HPLC separation on a ChiralCel OG column (10 μm, 0.46×25 cm, 5% i-PrOH-hexane, 1 mL/min).

(−)-(2R)-99: $[α]_D^{25}$ −9 (c 0.009, THF).

5-(tert-Butyloxycarbonyl)-7-hydroxy-1-(hydroxymethyl)-1,2,3,4-tetrahydro-5H-naphtho[1,2-b]azepine (101).

Following the general procedure detailed for 86, 84 (0.015 g, 0.035 mmol, 1 equiv) was treated with 10% Pd—C (0.001 g, 0.3 equiv) followed by aqueous HCO$_2$NH$_4$ (0.2 mL, 25% w/v, 23 equiv). Filtration and concentration gave 101 as an analytically pure colorless oil in quantitative yield (0.012 g, 0.012 g theoretical) which crystallized upon storage: mp 202–203° C.; $^1$H NMR 400 MHz, CDCl$_3$) major rotamer δ 9.19 (s, 1H), 8.07–8.05 (m, 1H), 7.26–7.22 (m, 1H), 6.81–6.75 (m, 2H), 6.50 (s, 1H), 4.28–4.24 (m, 1H), 4.18–4.08 (m, 2H), 3.89–3.86 (m, 1H), 2.85–2.79 (m, 1H), 2.11–2.07 (m, 1H), 1.94–1.91 (m, 1H), 1.70–1.67 (m, 2H), 1.62 (s, 9H); $^1$H NMR 400 MHz, acetone-d$_6$) major rotamer 9.03 (s, 1H), 8.26 (d, J=8.2 Hz, 1H), 8.07 (d, J=8.6 Hz, 1H), 7.55–7.51 (m, 1H), 7.46–7.43 (m, 1H), 6.74 (s, 1H), 4.37–4.33 (m, 1H), 4.03–3.99 (m, 1H), 3.91–3.80 (m, 1H), 3.61–3.52 (m, 2H), 2.73–2.66 (m, 1H), 2.36–2.32 (m, 1H), 2.20–2.10 (m, 1H), 1.60–1.55 (m, 1H), 1.33 (s, 9H); IR (film) $v_{max}$ 3272, 2976, 2925, 1662, 1621, 1596 cm$^{-1}$; FABHRMS (NBA-NaI) m/z 344.1855 (M+H$^+$, C$_{20}$H$_{25}$NO$_4$ requires 344.1862).

Acid-Catalyzed Addition of CH$_3$OH to 78: 6-(tert-Butyloxycarbonyl)-8-hydroxy-2-methoxy-1,2,3,4,5-pentahydro-6H-naphtho[1,2-b]azocine (100).

A solution of 78 (0.0069 g, 0.021 mmol, 1 equiv) in freshly distilled CH$_3$OH (1.0 mL) was treated with CF$_3$SO$_3$H (0.027 mL, 0.1 M in CH$_3$OH, 0.12 equiv) at 25° C. for 5 min. Workup as described for 101 and radial chromatography (SiO$_2$, 1 mm plate, 50% EtOAc-hexane) provided 100 as a colorless oil (0.0070 g, 0.0076 g theoretical, 92%) which slowly crystallized upon storage: mp 199–200° C. with decomposition; $^1$H NMR (500 MHz, acetone-d$_6$) major rotamer δ 9.09 (s, 1H), 8.27 (d, J=8.5 Hz, 1H), 8.11 (d, J=8.5 Hz, 1H), 7.59–7.56 (m, 1H), 7.49–7.47 (m, 1H), 6.69 (s, 1H), 4.37–4.29 (m, 1H), 3.57–3.56 (m, 1H), 3.49–3.46 (m, 1H), 3.43 (s, 3H), 2.85–2.79 (m, 2H), 1.99–1.90 (m, 1H), 1.81–1.75 (m, 1H), 1.28 (s, 9H overlapping with m, 2H); IR (film) $v_{max}$ 3268, 2971, 2868, 1695, 1664, 1587 cm$^{-1}$; FABHRMS (NBA-CsI) mz 357.1951 (M+Cs$^+$, C$_{21}$H$_{27}$NO$_4$ requires 357.1940).

Addition of HCl to 78: 6-(tert-Butyloxycarbonyl)-2-chloro-8-hydroxy-1,2,3,4,5-pentahydro-6H-naphthol[1,2-b]azocine (102).

A solution of 78 (0.0031 g, 0.0095 mmol, 1 equiv) in THF (0.31 mL) was treated with 3.3 M HCl—THF (0.0043 mL, 1.5 equiv) at −78° C. for 5 min. Evaporation of the volatiles and chromatography (SiO$_2$ 1×7 cm, 30% EtOAc-hexane) furnished 102 as a pure white foam (0.0034 g, 0.0034 g theoretical, 100%): $^1$H NMR 400 MHz, acetone-d$_6$) major rotamer δ 9.27 (br s, 1H), 8.27 (d, J=8.5 Hz, 1H), 8.06 (d, J=8.5 Hz, 1H), 7.63–7.59 (m, 1H), 7.57–7.49 (m, 1H), 6.72 (s, 1H), 4.49–4.43 (m, 1H), 3.67–3.63 (m, 1H), 3.24–3.21 (m, 1H), 2.88–2.82 (m, 2H), 2.02–1.90 (m, 1H), 1.81–1.75 (m, 1H), 1.68–1.67 (m, 1H), 1.43–1.41 (m, 1H), 1.29 (s, 9H); IR (film) $v_{max}$ 3251, 2974, 2933, 1692, 1662, 1621, 1585 cm$^{-1}$; FABHRMS (NBA-NaI) m/z 384.1333 (M+Na$^+$, C$_{20}$H$_{24}$ClNO$_3$ requires 384.1342).

4-(Benzyloxy)-1-bromo-N-(tert-butyloxycarbonyl)-N-(4-penten-1-yl)naphthylamine (103).

A solution of the carbamate 102 (500 mg, 1.17 mmol) in benzene (25 mL) was added to a mixture of 50% aqueous NaOH (5 g) and benzyltributylammonium chloride (720 mg, 2.30 mmol, 2 equiv). The mixture was stirred vigorously for 15 min and 1-((methanesulfonyl)oxy)-4-pentene (1.91 g, 11.6 mmol, 10 equiv) was added. The mixture was stirred vigorously for 24 h at 25° C. Ice-cold H$_2$O (200 mL), and EtOAc (50 mL) were added. The aqueous layer was extracted with EtOAc (50 mL), the combined organic layers were dried (Na$_2$SO$_4$) and the solvent was removed under vacuum. Chromatography (SiO$_2$, 4×20 cm, 15% EtOAc-hexane gradient elution) afforded 103 (272 mg, 581 mg theoretical, 47%) as an oil: $^1$H NMR (CDCl$_3$, 400 MHz) δ 8.34 (d, J=8.3 Hz, 1H), 8.27 (d, J=8.6 Hz, 1H), 7.63 (t, J=7.3 Hz, 1H), 7.55–7.49 (m, 3H), 7.42–7.33 (m, 3H), 6.77 and 6.68 (two s, 1H), 5.85 (m, 1H), 5.32–5.25 (m, 2H), 5.92 (m, 2H), 3.78 (m, 1H), 3.48 (m, 1H), 2.03 (m, 2H), 2.85–1.54 (m, 2H), 1.31 (s, 9H); IR (film) $v_{max}$ 2975, 2947, 1717, 1701, 1624, 1486 cm$^{-1}$; FABHRMS (NBA-CsI) m/z 628.0439 (M+Cs$^+$, C$_{27}$H$_{30}$BrNO$_3$ requires 628.0463).

Anal. Calcd for C$_{27}$H$_{30}$BrNO$_3$: C, 65.32; H, 6.09; N, 2.82. Found: C, 65.42; H, 5.90; N, 2.97.

5-((tert-Butyldimethylsilyl)oxy)-1-((tetrahydropyranyl)oxy)-1-pentene (105).

A suspension of triphenyl[(2-tetrahydropyranyloxy)methyl]phosphonium chloride (6.12 g, 14.8 mmol, 3 equiv) in THF (50 mL) at −78° C. was treated dropwise with a solution of n-BuLi (5.7 mL, 2.5 M in hexane, 14.3 mmol, 2.9 equiv). The reaction mixture was stirred for 5 min at −78° C., the cooling bath was removed and the mixture allowed to warm until it reached 0° C. The mixture was recooled to −78° C., and HMPA (21.5 mL, 123 mmol, 24.9 equiv) and 104 (1 g, 4.9 mmol) were added sequentially. The reaction mixture was stirred for 1.5 h at −78° C. and 24 h at 25° C. before it was quenched by the addition of phosphate buffer (500 mL, pH 7). The mixture was extracted with EtOAc (3×100 mL), and the combined organic phase was dried (Na$_2$SO$_4$) and the solvent removed under vacuum. Chromatography (SiO$_2$, 4×25 cm, 10% EtOAc-hexane containing 1% Et$_3$N) afforded 105 (1.37 g, 1.48 g theoretical, 92%) as a colorless oil as a mixture of E- and Z-olefin isomers (50:50): $^1$H NMR (CDCl$_3$, 400 MHz) δ 6.24 (dt, J=12.3, 1.3 Hz, 0.5H), 6.14 (dt, J=6.3, 1.4 Hz, 0.5H), 5.09 (dt, J=12.3, 7.5 Hz, 0.5H), 4.88 and 4.85 (two t, J=3.1, 3.4 Hz, 1H), 4.47 (m, 0.5H), 3.83 and 3.54 (two m, 2H), 3.62 and 3.59 (two t, J=6.4 Hz, 6.6 Hz, 2H), 2.17 and 1.98 (two m, 2H), 1.85–1.49 (m, 8H), 0.883 and 0.877 (two s, 9H), 0.04 and 0.03 (two s, 6H); IR (film) ν$_{max}$ 2929, 2856, 1673, 1472 cm$^{-1}$; FABMS (NBA-NaI) m/z 301 (M+H$^+$).

Anal. Calcd for C$_{16}$H$_{32}$O$_3$Si: C, 63.95; H, 10.73. Found: C, 64.02; H, 10.43.

1-((Tetrahydropyranyl)oxy)-1-penten-5-ol (106).

A solution of 105 (900 mg, 3 mmol) in THF (20 mL) was treated with Bu$_4$NF (1 M in THF, 3 mL, 3 mmol, 1 equiv) at 0° C. The reaction mixture was stirred at 0° C. for 1 h and at 25° C. for 2 h. Phosphate buffer (100 mL, pH 7) was added and the mixture was extracted with EtOAc-hexane (2:1, 3×30 mL). The combined organic phase was dried (Na$_2$SO$_4$) and the solvent removed under vacuum. Chromatography (SiO$_2$, 4×25 cm, 30% EtOAc-hexane containing 2% Et$_3$N) afforded 106 (445 mg, 557 mg theoretical, 80%) as a colorless oil as a mixture of E- and Z-olefin isomers (50:50). Careful rechromatography of this material (SiO$_2$, 4×25 cm, 10–30% EtOAc-hexane containing 2% Et$_3$N gradient elution) enabled the partial separation of the two isomers.

E-isomer: $^1$H NMR (CDCl$_3$, 400 MHz) δ 6.26 (m, 1H), 5.07 (dt, J=12.3, 7.5 Hz, 1H), 4.86 (t, J=3.1 Hz, 1H), 3.83 and 3.54 (two m, 2H), 3.62 (t, J=6.4 Hz, 2H), 2.01 (m, 2H), 1.89–1.50 (m, 8H); IR (film) ν$_{max}$ 3395, 2938, 2853, 1674, 1202 cm$^{-1}$.

Anal. Calcd for C$_{10}$H$_{18}$O$_3$: C, 64.49; H, 9.74. Found: C, 64.76; H, 9.58.

Z-isomer: $^1$H NMR (CDCl$_3$, 400 MHz) δ 6.17 (dt, J=6.3, 1.2 Hz, 1H), 4.84 (t, J=3.3 Hz, 1H), 4.45 (dt, J=6.3, 7.6 Hz, 1H), 3.79 and 3.52 (two m, 2H), 3.59 (t, J=6.3 Hz, 1H), 2.23 (br s, 1H), 2.18 (m, 2H), 1.85–1.46 (m, 8H); IR (film) ν$_{max}$ 3404, 2941, 2870, 1669, 1356, 1254 cm$^{-1}$.

5-((Methanesulfonyl)oxy)-1-((tetrahydropyranyl)oxy)-1-pentene (107).

The alcohol 106 (147 mg, 0.791 mmol) was added to a suspension of NaH (60% in oil, 38 mg, 0.95 mmol, 1.2 equiv) in THF (5 mL). The resulting mixture was stirred at 25° C. for 30 min and cooled to 0° C. before CH$_3$SO$_2$Cl was added dropwise. The reaction mixture was stirred 15 min at 0° C. and 15 min at 25° C. Phosphate buffer (100 mL, pH 7) was added and the mixture extracted with CH$_2$Cl$_2$ (2×50 mL). The combined organic phase was dried (Na$_2$SO$_4$) and the solvent was removed under vacuum. Chromatography (SiO$_2$, 2×25 cm, 30% EtOAc-hexane containing 2% Et$_3$N) afforded 107 (205 mg, 208 mg theoretical, 98%) as a colorless oil as a mixture of E- and Z-olefin isomers (50:50): $^1$H NMR (CDCl$_3$, 400 MHz) δ 6.24 (dt, J=12.3, 1.3 Hz, 0.5 H), 6.14 (dt, J=6.3, 1.4 Hz, 0.5H), 5.05 (dt, J=12.3, 7.5 Hz, 0.5H), 4.88 and 4.85 (two t, J=3.1, 3.4 Hz, 1H), 4.43 (m, 0.5H), 4.15 (m, 1H), 3.83 and 3.54 (two m, 2H), 3.05 (s, 3H), 2.17 and 1.98 (two m, 2H), 1.85–1.49 (m, 8H).

4-(Benzyloxy)-N-(tert-butyloxycarbonyl)-1-iodo-N-[5-((tetrahydropyranyl)oxy)-4-penten-1-yl]naphthylamine (108).

A solution of 80 (53 mg, 112 μmol) in benzene (5 mL) was added to a mixture of 50% aqueous NaOH (0.5 g) and benzyltributylammonium chloride (70 mg, 224 μmol, 2 equiv). The mixture was stirred vigorously for 15 min and 100 (147 mg, 556 μmol, 5 equiv) was added. The mixture was stirred vigorously for 12 h at 25° C. Ice-cold H$_2$O (50 mL), and EtOAc (10 mL) were added. The aqueous layer was extracted with EtOAc (10 mL), the combined organic layers were dried (Na$_2$SO$_4$) and the solvent was removed under vacuum. Chromatography (SiO$_2$, 2×20 cm, 10–25% EtOAc-hexane gradient elution) afforded 108 (58 mg, 72 mg theoretical, 80%) as an oil: $^1$H NMR (CDCl$_3$, 400 MHz) δ 8.31 and 8.27 (two d, J=8.3, 8.8 Hz, 1H), 8.21 (d, J=8.2 Hz, 1H), 7.61–7.49 (m, 4H), 7.42–7.33 (m, 3H), 6.82–6.69 (m, 1H), 6.21 (m, 0.5H), 6.13 (d, 0.5H), 5.32–5.17 (m, 2H), 5.01 (dt, J=12.2, 7.5 Hz, 0.5H), 4.86 and 4.82 (two m, 1H), 4.41 (m, 0.5H), 3.81 (m, 2H), 3.51 (m, 1H), 3.36–3.21 (m, 1H), 2.12 and 1.92 (two m, 2H), 1.83–1.49 (m, 8H), 1.29 (s, 9H); IR (film) ν$_{max}$ 2940, 1699, 1591, 1407, 1366, 1338, 1158, 1099, 1037 cm$^{-1}$.

4-(Benzyloxy)-1-bromo-N-(tert-butyloxycarbonyl)-N-[5-((tetrahydropyranyl)oxy)-4-penten-1-yl]naphthylamine (109).

A solution of 102 (37 mg, 86 μmol) in benzene (2 mL) was added to a mixture of 50% aqueous NaOH (0.5 g) and benzyltributylammonium chloride (54 mg, 172 μmol, 2 equiv). The mixture was stirred vigorously for 15 min and 107 (122 mg, 461 μmol, 7.7 equiv) was added. The mixture was stirred vigorously for 12 h at 25° C. Ice-cold H$_2$O (50 mL), and EtOAc (10 mL) were added. The aqueous layer was extracted with EtOAc (10 mL), the combined organic layers were dried (Na$_2$SO$_4$), and the solvent was removed under vacuum. Chromatography (SiO$_2$, 2×20 cm, 10–25% EtOAc-hexane gradient elution) afforded 109 (40 mg, 51 mg theoretical, 80%) as an oil: $^1$H NMR (CDCl$_3$, 400 MHz) δ 8.34 (d, J=8.3 Hz, 1H), 8.27 (d, J=8.6 Hz, 1H), 7.62 (t, J=7.3 Hz, 1H), 7.55–7.49 (m, 3H), 7.42–7.33 (m, 3H), 6.80–6.68 (m, 1H), 6.18 (d, J=12.0 Hz, 0.5H), 6.12 (d, J=6.3 Hz, 0.5H), 5.30–5.16 (m, 2H), 5.00 (dt, J=12.2, 7.4 Hz, 0.5H), 4.84 and 4.80 (two m, 1H), 4.40 (m, 0.5H), 3.83–3.72 and 3.51–3.31 (two m, 4H), 2.12 and 1.91 (two m, 2H), 1.82–1.49 (m, 8H), 1.29 (s, 9H), IR (film) ν$_{max}$ 2945, 2937, 1703, 1591, 1405, 1370, 1163, 1100 cm$^{-1}$.

4-(Benzyloxy)-N-(tert-butyloxycarbonyl)-1-iodo-N-(4-oxobut-1-yl)naphthylamine (110).

A solution of 81 (44 mg, 81 μmol) in THF (3 mL) was treated sequentially with a solution of NaIO$_4$ (35 mg, 162 μmol, 2 equiv) in 0.5 mL H$_2$O and a solution of OsO$_4$ (7.5 mM in THF, 0.53 mL, 4 μmol, 0.05 equiv). The reaction mixture was stirred for 6 h at 25° C. EtOAc (20 mL) was added and the organic layer was dried (Na$_2$SO$_4$), filtered through Celite, and the solvent removed under vacuum. Chromatography (SiO$_2$, 1×15 cm, 15% EtOAc-hexane) afforded 110 (35 mg, 80%) as an oil: $^1$H NMR (CDCl$_3$, 400 MHz) δ 9.73 (t, J=1.3 Hz, 1H), 8.32 (d, J=8.2 Hz, 1H), 8.20 (d, J=8.4 Hz, 1H), 7.61–7.49 (m, 4H), 7.42–7.32 (m, 3H), 6.77 and 6.72 (two s, 1H), 5.32–5.25 (m, 2H), 3.86 (ddd, J=14.0, 8.6, 6.7 Hz, 1H), 3.47 (m, 1H), 2.48 (m, 2H), 1.93–1.75 (m, 2H), 1.29 and 1.23 (two s, 9H); IR (film) ν$_{max}$ 3064, 3032, 2975, 2930, 2722, 1638, 1616, 1590, 1407, 1160 cm$^{31\ 1}$; FABHRMS (NBA-CsI) m/z 678.0095 (M+Cs$^+$, C$_{26}$H$_{28}$INO$_4$ requires 678.0117).

4-(Benzyloxy)-1-bromo-N-(tert-butyloxycarbonyl)-N-(4-oxobut-1-yl)naphthylamine (111).

A solution of 102 (115 mg, 0.23 mmol) in THF (8 mL) was treated sequentially with a solution of NaIO$_4$ (110 mg, 514 μmol, 2 equiv) in 1.5 mL H$_2$O and a solution of OsO$_4$ (7.5 mM in THF, 1.5 mL, 11.2 μmol, 0.05 equiv). The reaction mixture was stirred for 6 h at 25° C. EtOAc (20 mL) was added and the organic layer was dried (Na$_2$SO$_4$), filtered through Celite, and the solvent removed under vacuum. Chromatography (Si02, 2×15 cm, 15% EtOAc-hexane) afforded 111 (75 mg, 65%) as an oil: $^1$H NMR (CDCl$_3$, 400 MHz) δ 9.73 (t, J=1.3 Hz, 1H), 8.35 (d, J=8.2 Hz, 1H), 8.27 (d, J=8.4 Hz, 1H), 7.62 (t, J=7.3 Hz, 1H), 7.56–7.49 (m, 3H), 7.42–7.32 (m, 3H), 6.75 and 6.70 (two s, 1H), 5.33–5.23 (m, 2H), 3.87 (m, 1H), 3.48 (m, 1H), 2.48 (2H), 1.92–1.77 (m, 2H), 1.29 and 1.23 (two s, 9H); IR (film) $v_{max}$ 3064, 3032, 2975, 2930, 2722, 1638, 1616, 1590, 1407, 1160 cm$^{-1}$; FABHRMS (NBA-CsI) m/z 630.0262 (M+Cs$^+$, $C_{26}H_{28}BrNO_4$ requires 630.0253).

(E)-4-(Benzyloxy)-N-(tert-butyloxycarbonyl)-1-iodo-N-[5-(methoxycarbonyl)-4-penten-1-yl]naphthylamine (112).

A solution of 110 (13.3 mg, 24.4 μmol) in THF (0.3 mL) was treated with methyl (triphenylphosphoranylidene) acetate (23.9 mg, 71.5 μmol, 3 equiv). The reaction mixture was stirred for 48 h at 25° C. and the solvent removed under vacuum. Chromatography (SiO$_2$, 10–25% EtOAc-hexane gradient elution) afforded 112 (9 mg, 14 mg theoretical, 63%) as an oil: $^1$H NMR (CDCl$_3$, 400 MHz) δ 8.32 (d, J=8.2 Hz, 1H), 8.20 (d, J=8.2 Hz, 1H), 7.61–7.48 (m, 5H), 7.42–7.32 (m, 2H), 6.91 (m, 1H), 6.74 and 6.64 (two s, 1H), 5.79 (d, J=15.5 Hz, 1H), 5.31–5.23 (m, 2H), 3.81 (ddd, J=14.0, 9.6, 3.6 Hz, 1H), 3.70 (s, 3H), 3.35 (m, 1H), 2.18 (m, 2H), 1.75–1.55 (m, 2H), 1.29 and 1.24 (two s, 9H); IR (film) $v_{max}$ 2975, 2947, 1702, 1658, 1471, 1391, 1366, 1307, 1272, 1162 cm$^{-1}$.

(E)-4-(Benzyloxy)-1-bromo-N-(tert-butyloxycarbonyl)-N-[5-(methoxyearbonyl)-4-penten-1-yl]naphthylamine (113).

A solution of 111 (50.0 mg, 100 μmol) in THF (3 mL) was treated by methyl (triphenylphosphoranylidene)acetate (100 mg, 301 μmol, 3 equiv). The reaction mixture was stirred for 48 h at 25° C. and the solvent removed under vacuum. Chromatography (SiO$_2$, 10–40% EtOAc-hexane gradient elution) afforded 113 (52 mg, 55 mg theoretical, 94%) as an oil: $^1$H NMR (CDCl$_3$, 400 MHz) δ 8.35 (d, J=8.2 Hz, 1H), 8.27 (d, J=8.2 Hz, 1H), 7.64–7.48 (m, 5H), 7.42–7.35 (m, 2H), 6.90 (m, 1H), 6.74 and 6.65 (two s, 1H), 5.81 (d, J=15.5 Hz, 1H), 5.32–5.16 (m, 2H), 3.81–3.65 (m, 1H, partially obscured), 3.69 (s, 3H), 3.48 (m, 1H), 2.19 (m, 2H), 1.75–1.55 (m, 2H), 1.29 and 1.24 (two s, 9H); IR (film) $v_{max}$ 2976, 2945, 1698, 1657, 1394, 1367, 1311, 1272, 1163 cm$^{-1}$.

Anal. Calcd for $C_{29}H_{32}BrNO_5$: C, 62.82; H, 5.82; N, 2.53. Found: C, 62.80; H, 5.60; N, 2.52.

114. A sample of 112 (31.5 mg, 0.05 mmol) in a thick-walled reaction vessel and (Ph$_3$P)$_4$Pd (2 mg, 0.001 mmol) was placed under Ar. To the reaction vessel was added CH$_3$CN (1.14 mL) and Et$_3$N (16 μL, 0.1 mmol). The mixture was heated at 115° C. for 24 h. The reaction mixture was cooled and was concentrated under a stream of N$_2$. Chromatography (SiO$_2$ 20% EtOAc-hexane) gave 24.3 mg (90%) of 112 as a yellow oil: $^1$H NMR (CDCl$_3$, 400 MHz) δ 6.80 (br s, 1H), 7.88 (d, J=6.8 Hz, 1H), 7.52–7.32 (m, 7H), 6.68 (s, 1H), 5.78 (s, 1H), 5.22 (br s, 2H), 4.26 (br s, 1H), 3.82 (br s, 1H), 3.74 (s, 3H), 1.55–1.39 (m, 4H), 1.23 (br s, 9H); $^{13}$C NMR δ 166.5, 158.5, 154.0, 136.7, 136.2, 131.1, 128.6, 128.0, 127.3, 127.1, 125.2, 122.3, 120.7, 120.4, 106.3, 105.8, 70.2, 51.1, 48.8, 47.3, 30.4, 30.1, 28.2, 27.2; IR $v_{max}$ 3070, 2975, 1715, 1694 cm$^{31}$ $^1$; FABHRMS m/z 606.1257 (M+Cs$^+$, $C_{29}H_{31}NO_5$ requires 606.1283).

What is claimed is:

1. A compound selected from the group consisting of:

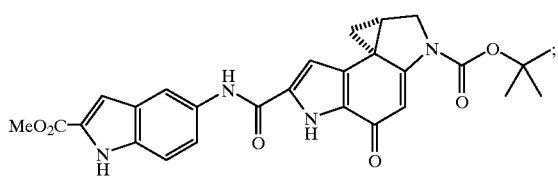

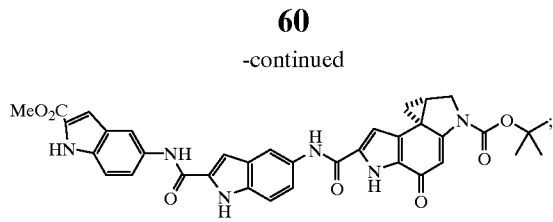

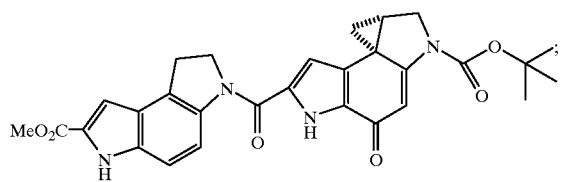

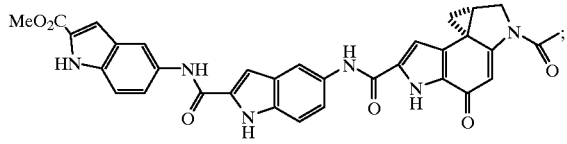

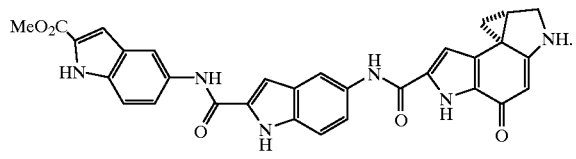

and

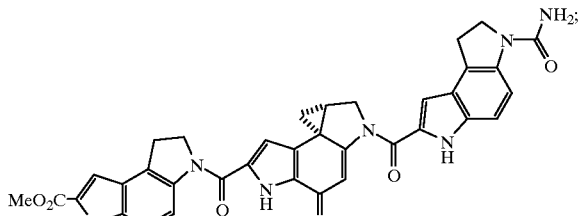

2. A compound selected from the group consisting of:

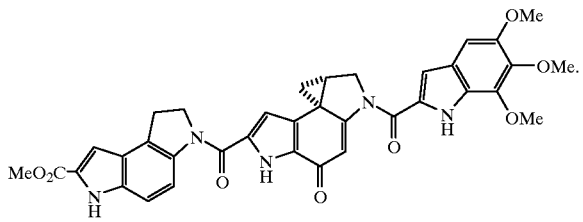

and

3. A compound selected from the group consisting of:

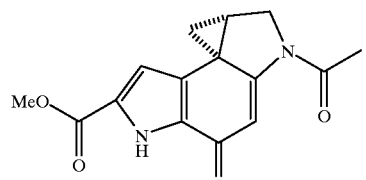

and

-continued
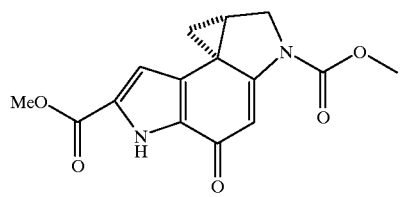
4. A compound selected from the group consisting of:
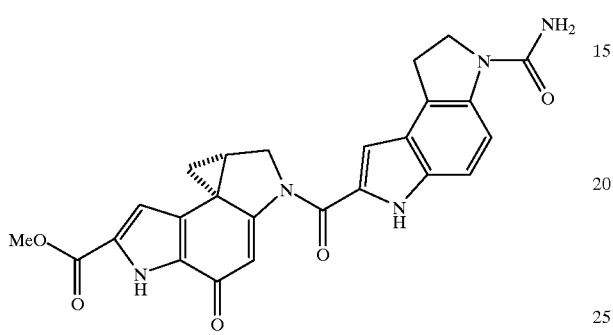
and
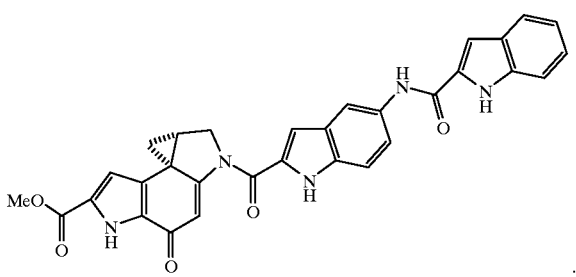
.
5. A compound selected from the group consisting of:
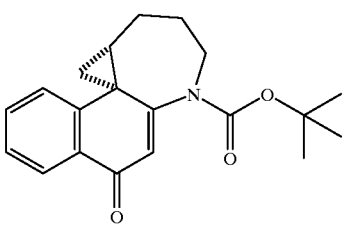
;
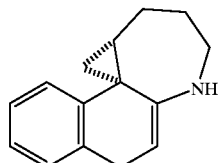
;
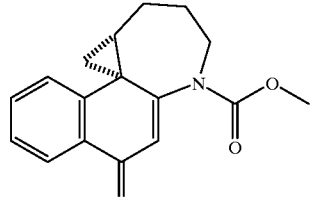
; and
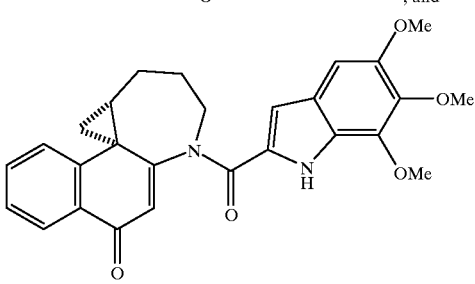
.
* * * * *